(12) United States Patent
Kato et al.

(10) Patent No.: US 9,221,928 B2
(45) Date of Patent: Dec. 29, 2015

(54) FLUORINE-CONTAINING SULFONATE RESIN, FLUORINE-CONTAINING N-SULFONYLOXYIMIDE RESIN, RESIST COMPOSITION AND PATTERN FORMATION METHOD

(75) Inventors: Misugi Kato, Kawagoe (JP); Yoshimi Isono, Kawagoe (JP); Satoru Narizuka, Kawagoe (JP); Ryozo Takihana, Kawagoe (JP); Kazunori Mori, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 13/524,627

(22) Filed: Jun. 15, 2012

(65) Prior Publication Data

US 2012/0328985 A1 Dec. 27, 2012

Related U.S. Application Data

(63) Continuation-in-part of application No. 13/333,322, filed on Dec. 21, 2011, now abandoned.

(30) Foreign Application Priority Data

Jun. 20, 2011 (JP) ................................ 2011-136028
Mar. 28, 2012 (JP) ................................ 2012-074109
Jun. 6, 2012 (JP) ................................ 2012-128859

(51) Int. Cl.
| | | |
|---|---|---|
| *C08F 20/38* | (2006.01) | |
| *C08F 22/24* | (2006.01) | |
| *C08F 28/02* | (2006.01) | |
| *C07C 309/12* | (2006.01) | |
| *G03F 7/028* | (2006.01) | |
| *G03F 7/004* | (2006.01) | |
| *G03F 7/038* | (2006.01) | |
| *G03F 7/039* | (2006.01) | |
| *C07C 381/12* | (2006.01) | |
| *C07C 25/18* | (2006.01) | |
| *C07D 333/08* | (2006.01) | |
| *C07D 333/76* | (2006.01) | |
| *C07D 207/46* | (2006.01) | |
| *C07D 209/48* | (2006.01) | |

(52) U.S. Cl.
CPC .............. *C08F 20/38* (2013.01); *C07C 25/18* (2013.01); *C07C 309/12* (2013.01); *C07C 381/12* (2013.01); *C08F 22/24* (2013.01); *C08F 28/02* (2013.01); *G03F 7/0045* (2013.01); *G03F 7/0382* (2013.01); *G03F 7/0397* (2013.01); *C07D 207/46* (2013.01); *C07D 209/48* (2013.01); *C07D 333/08* (2013.01); *C07D 333/76* (2013.01); *G03F 7/0046* (2013.01)

(58) Field of Classification Search
None
See application file for complete search history.

(56) References Cited

U.S. PATENT DOCUMENTS

| | | | |
|---|---|---|---|
| 5,945,250 | A | 8/1999 | Aoai et al. |
| 7,632,965 | B2 | 12/2009 | Nozawa et al. |
| 7,812,105 | B2 | 10/2010 | Nagai et al. |
| 7,956,142 | B2 | 6/2011 | Nagai et al. |
| 2010/0035185 | A1 | 2/2010 | Hagiwara et al. |
| 2010/0304303 | A1* | 12/2010 | Maeda et al. ............... 430/286.1 |
| 2011/0015431 | A1 | 1/2011 | Jodry et al. |
| 2011/0034721 | A1 | 2/2011 | Hagiwara et al. |
| 2011/0112306 | A1 | 5/2011 | Nagamori et al. |
| 2011/0177453 | A1* | 7/2011 | Masubuchi et al. ......... 430/270.1 |
| 2011/0189607 | A1* | 8/2011 | Ohashi et al. ............... 430/270.1 |

FOREIGN PATENT DOCUMENTS

| | | | |
|---|---|---|---|
| CA | 2049772 | A1 | 2/1992 |
| JP | 4-230645 | A | 8/1992 |
| JP | 3613491 | B2 | 11/2004 |
| JP | 2005-84365 | A | 3/2005 |
| JP | 2006-178317 | A | 7/2006 |
| JP | 2006-232797 | A | 9/2006 |
| JP | 2006-291188 | A | 10/2006 |
| JP | 2007-197718 | A | 8/2007 |
| JP | 2008-133448 | A | 6/2008 |

(Continued)

*Primary Examiner* — Cynthia H Kelly
*Assistant Examiner* — Anna Malloy
(74) *Attorney, Agent, or Firm* — Crowell & Moring LLP

(57) ABSTRACT

A fluorine-containing sulfonate salt resin or fluorine-containing sulfonate ester resin having a structure of the following general formula (A) and a fluorine-containing N-sulfonyloxyimide resin having a repeating unit of the general formula (17).

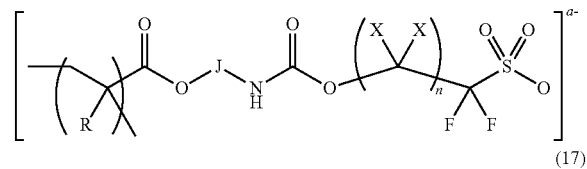

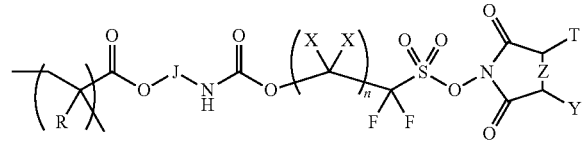

And a resist composition using the above resin such that the resist composition can attain high resolution, wide DOF, small LER and high sensitivity and form a good pattern shape.

10 Claims, No Drawings

(56) References Cited

FOREIGN PATENT DOCUMENTS

| JP | 2009-7327 A | 1/2009 |
| JP | 2009-91351 A | 4/2009 |
| JP | 2010-18573 A | 1/2010 |
| JP | 2010-95643 A | 4/2010 |
| JP | 2010095643 A * | 4/2010 |
| WO | WO 2006/121096 A1 | 11/2006 |
| WO | WO 2008/056795 A1 | 5/2008 |

* cited by examiner

FLUORINE-CONTAINING SULFONATE RESIN, FLUORINE-CONTAINING N-SULFONYLOXYIMIDE RESIN, RESIST COMPOSITION AND PATTERN FORMATION METHOD

CROSS REFERENCES TO RELATED APPLICATIONS

This application is a continuation-in-part of U.S. application Ser. No. 13/333,322, filed Dec. 21, 2011 now abandoned, which claims priority under 35 U.S.C. §119 to Japanese Application No. 2011-136028, filed Jun. 20, 2011, Japanese Application No. 2012-074109, filed Mar. 28, 2012, and Japanese Application No. 2012-128859, filed Jun. 6, 2012, the entire disclosures of which are herein expressly incorporated by reference.

FIELD OF THE INVENTION

The present invention relates to a fluorine-containing sulfonate resin, a fluorine-containing N-sulfonyloxyimide resin, a resist composition and a pattern formation method using the resist composition. More particularly, the present invention relates to a resist composition suitably usable as a chemically amplified resist material for fine patterning by high energy radiation and a novel fluorine-containing sulfonate resin and fluorine-containing N-sulfonyloxyimide resin each for use in such a resist composition.

BACKGROUND OF THE INVENTION

With the adoption of fine lithographic patterning techniques in semiconductor manufacturing processes, there arises a need to provide resist compositions that can be exposed at shorter wavelengths and show wide depth of focus tolerance (abbreviated as "DOF"), small line edge roughness (abbreviated as "LED"), high resolution, high sensitivity, good substrate adhesion and high etching resistance.

It is reported that the introduction of a fluorine atom or an aliphatic moiety into a resist resin would produce a certain effect on the reduction of the exposure wavelength. Further, it is attempted to use, as an anion moiety of an acid generator, a fluorine-containing sulfonic acid of high acidity in order to attain wide depth of focus tolerance and small pattern line edge roughness. It is also attempted to provide a resist resin whose copolymerization component has an acid generator function for improvements in resist characteristics. As such a resist resin, there have been proposed a resin containing a sulfonic acid onium salt as an acid generator in a side chain thereof with an anion moiety of the acid generator fixed to the resin (see Patent Documents 1 to 7). For example, Patent Documents 6 and 7 disclose resist compositions, each of which uses a resin obtained by polymerization or copolymerization of a methacrylic acid ester containing in a side chain thereof a triphenylsulfonium salt of sulfonic acid having a fluorine atom at its α-position.

[Prior Art Documents]
Patent Document 1: Japanese Patent No. 3613491
Patent Document 2: International Application Publication No. WO 2006/121096
Patent Document 3: Japanese Laid-Open Patent Publication No. 2006-178317
Patent Document 4: Japanese Laid-Open Patent Publication No. 2007-197718
Patent Document 5: Japanese Laid-Open Patent Publication No. 2008-133448
Patent Document 6: Japanese Laid-Open Patent Publication No. 2009-7327
Patent Document 7: Japanese Laid-Open Patent Publication No. 2010-95643

SUMMARY OF THE INVENTION

There have been proposed many resist resins each containing a sulfonic acid onium salt as an acid generator in a side chain thereof with an anion moiety of the acid generator fixed to the resin as mentioned above, so that the resulting resist compositions can attain high resolution, wide DOF, small LER and high sensitivity and form good pattern shapes. However, these resist resins are not yet satisfactory in comprehensive view of DOF, LER, sensitivity and resolution and are in need of further improvements.

As a result of extensive researches made to achieve the above object, the present inventors have found that: when either a polymerizable fluorine-containing sulfonic acid onium salt of specific fluorine-containing sulfonate structure or a polymerizable fluorine-containing N-sulfonyloxyimide compound of specific fluorine-containing N-sulfonyloxyimide structure is subjected to homopolymerization or copolymerization with a monomer for a resist resin, the resulting resin has a side chain formed with the sulfonic acid salt or the fluorine-containing N-sulfonyloxyimide compound so as to function as an acid generator; and the positive or negative resist composition prepared from such a resin can attain high sensitivity, high resolution, wide DOF and small LER and form a good pattern shape. The present invention is based on the above findings.

Namely, the present invention includes the following aspects.

[Inventive Aspect 1]

A fluorine-containing sulfonate salt resin or fluorine-containing sulfonate ester resin comprising a structure of the following general formula (A):

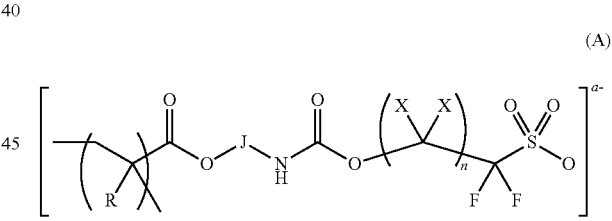

where X each independently represent a hydrogen atom or a fluorine atom; n represents an integer of 1 to 10; R represents a hydrogen atom, a halogen atom or a $C_1$-$C_3$ alkyl or fluorine-containing alkyl group; J represents a divalent linking group; and a represents 0 or 1.

[Inventive Aspect 2]

A fluorine-containing sulfonate resin comprising a repeating unit of the following general formula (3):

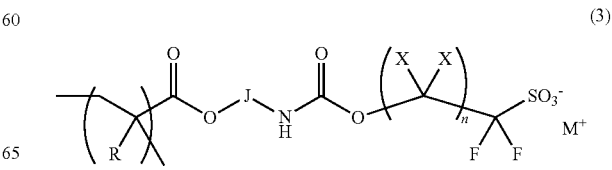

where X each independently represent a hydrogen atom or a fluorine atom; n represents an integer of 1 to 10; R represents a hydrogen atom, a halogen atom or a $C_1$-$C_3$ alkyl or fluorine-containing alkyl group; J represents a divalent linking group; and $M^+$ represents a monovalent cation.

[Inventive Aspect 3]

The fluorine-containing sulfonate resin according to Inventive Aspect 1 or 2, wherein the fluorine-containing sulfonate resin has a repeating unit of the following general formula (4):

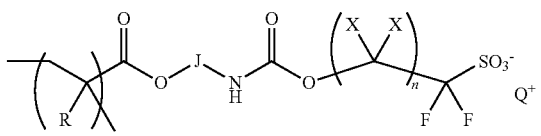

(4)

where X, n, R and J have the same definitions as in the general formula (A) or (3); and $Q^+$ represents either a sulfonium cation of the following general formula (a) or a iodonium cation of the following general formula (b);

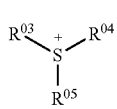

(a)

where $R^{03}$, $R^{04}$ and $R^{05}$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of $R^{03}$, $R^{04}$ and $R^{05}$ may be bonded together to form a ring with a sulfur atom in the formula,

(b)

where $R^{06}$ and $R^{07}$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^{06}$ and $R^{07}$ may be bonded together to form a ring with a iodine atom in the formula.

[Inventive Aspect 4]

A fluorine-containing N-sulfonyloxyimide resin comprising a repeating unit of the following general formula (17):

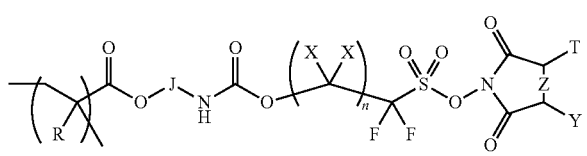

(17)

where X each independently represent a hydrogen atom or a fluorine atom; n represents an integer of 1 to 10; R represents a hydrogen atom, a halogen atom or a $C_1$-$C_3$ alkyl or fluorine-containing alkyl group; J represents a divalent linking group; Z represents a single bond, a double bond, a methylene group or an oxygen atom; T and Y each independently represent a hydrogen atom or a substituted or unsubstituted $C_1$-$C_{10}$ alkyl group and may form an aliphatic cyclic structure, an aromatic ring structure or a heterocyclic structure in combination thereof with carbon atoms to which T and Y are bonded.

[Inventive Aspect 5]

The fluorine-containing sulfonate resin according to Inventive Aspect 1 or 2, wherein the fluorine-containing sulfonate resin has a repeating unit of the following general formula (5):

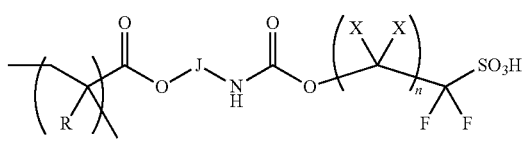

(5)

where X, n, R and J have the same definitions as in the general formula (A) or (3).

[Inventive Aspect 6]

The fluorine-containing sulfonate resin according to any one of Inventive Aspects 1 to 5, further comprising one kind or more kinds selected from the group consisting of repeating units foamed respectively by cleavage of polymerizable double bonds of olefins, fluorine-containing olefins, acrylic acid esters, methacrylic acid esters, fluorine-containing acrylic acid esters, fluorine-containing methacrylic acid esters, norbornene compounds, fluorine-containing norbornene compounds, styrenic compounds, fluorine-containing styrenic compounds, vinyl ethers and fluorine-containing vinyl ethers.

[Inventive Aspect 7]

The fluorine-containing sulfonate resin according to any one of Inventive Aspects 1 to 6, further comprising a repeating unit of the following general formula (6):

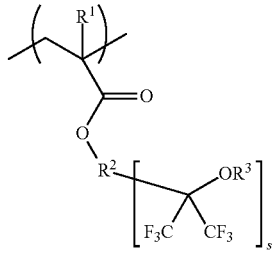

(6)

where $R^1$ represents a hydrogen atom, a halogen atom or a $C_1$-$C_3$ alkyl or fluorine-containing alkyl group; $R^2$ represents a substituted or unsubstituted aliphatic hydrocarbon group, a substituted or unsubstituted aromatic group or a divalent organic group formed by combination of a plurality thereof; any number of hydrogen atoms of $R^2$ may be substituted with a fluorine atom; $R^2$ may contain an ether bond or a carbonyl group; $R^3$ represents a hydrogen atom, a substituted or unsubstituted $C_1$-$C_{25}$ aliphatic hydrocarbon group or a substituted or unsubstituted $C_1$-$C_{25}$ aromatic hydrocarbon group; any number of hydrogen atoms of $R^3$ may be substituted with a fluorine atom; $R^3$ may contain an ether bond or a carbonyl group; and s represents an integer of 2 to 8.

[Inventive Aspect 8]

The fluorine-containing sulfonate resin according to any one of Inventive Aspects 1 to 7, further comprising a repeating unit of the following general formula (7):

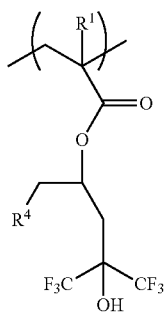

(7)

where $R^1$ represents a hydrogen atom, a halogen atom or a $C_1$-$C_3$ alkyl or fluorine-containing alkyl group; and $R^4$ represents a hydrogen atom or a $C_1$-$C_4$ alkyl or fluorine-containing alkyl group.

[Inventive Aspect 9]

The fluorine-containing sulfonate resin according to any one of Inventive Aspects 1 to 7, further comprising a repeating unit of the following general formula (8):

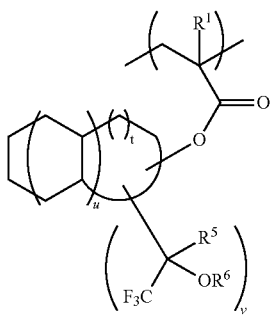

(8)

where $R^1$ represents a hydrogen atom, a halogen atom or a $C_1$-$C_3$ alkyl or fluorine-containing alkyl group; $R^5$ represents a methyl group or a trifluoromethyl group; $R^6$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an ether bond or a carbonyl group; u represents an integer of 0 to 2; t and v represent an integer of 1 to 8 and satisfy a relationship of $v \leq t+2$; and, in the case where v is an integer of 2 to 8, $R^5$ and $R^6$ may be the same or different.

[Inventive Aspect 10]

The fluorine-containing sulfonate resin according to any one of Inventive Aspects 1 to 9, further comprising a repeating unit of the following general formula (9):

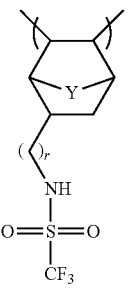

(9)

where Y represents either —$CH_2$—, —O— or —S—; and r represents an integer of 2 to 6.

[Inventive Aspect 11]

The fluorine-containing sulfonate resin according to any one of Inventive Aspects 1 to 10, further comprising a repeating unit of the following general formula (10):

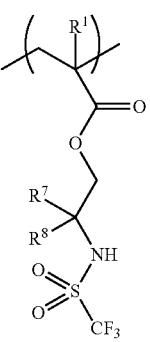

(10)

where $R^1$ represents a hydrogen atom, a halogen atom or a $C_1$-$C_3$ alkyl or fluorine-containing alkyl group; and $R^7$ and $R^8$ each independently represent a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an ether bond or a carbonyl group.

[Inventive Aspect 12]

The fluorine-containing sulfonate resin according to any one of Inventive Aspects 1 to 11, further comprising either a repeating unit of the following general formula (11) or a repeating unit of the following general formula (12):

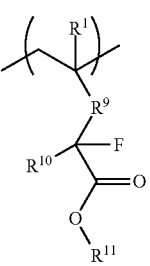

(11)

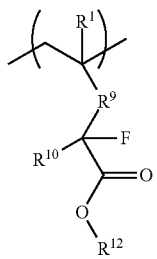

(12)

where $R^1$ represents a hydrogen atom, a halogen atom or a $C_1$-$C_3$ alkyl or fluorine-containing alkyl group; $R^9$ represents a divalent linking group; $R^{10}$ represents a hydrogen atom, a fluorine atom or a fluorine-containing alkyl group; $R^{11}$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an ether bond or a carbonyl group; and $R^{12}$ represents an acid labile group.

[Inventive Aspect 13]

The fluorine-containing sulfonate resin according to any one of Inventive Aspects 1 to 12, further comprising a repeating unit of the following general formula (16):

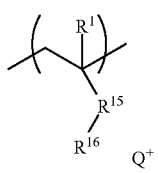

(16)

where $R^1$ represents a hydrogen atom, a halogen atom or a $C_1$-$C_3$ alkyl or fluorine-containing alkyl group; $R^{15}$ represents a divalent linking group; $R^{16}$ represents either —$SO_3^-$, —$CO_2^-$ or —$N^-HSO_3$; and $Q^+$ represents either a sulfonium cation or an iodonium cation.

[Inventive Aspect 14]

A resist composition comprising at least the fluorine-containing sulfonate resin according to any one of Inventive Aspects 1 to 13 and a solvent.

[Inventive Aspect 15]

The resist composition according to Inventive Aspect 14, wherein the fluorine-containing sulfonate resin has an acid labile group so that the resist composition serves as a chemically amplified positive resist composition.

[Inventive Aspect 16]

The resist composition according to Inventive Aspect 14 or 15, further comprising an acid labile group-containing resin.

[Inventive Aspect 17]

A pattern formation method, comprising: applying the resist composition according to any one of Inventive Aspects 14 to 16 to a substrate; heat treating the applied resist composition and exposing the heat treated resist composition to high energy radiation of 300 nm or less wavelength through a photomask; and, after optionally heat treating the exposed resist composition, developing the exposed resist composition with a developer.

[Inventive Aspect 18]

The pattern formation method according to Inventive Aspect 17, wherein said developing is performed by liquid immersion lithography in which water or any liquid medium other than water, having a higher refractive index than air, is inserted between the substrate to which the resist composition has been applied and a projection lens.

[Inventive Aspect 19]

A polymerizable fluorine-containing sulfonate salt or polymerizable fluorine-containing sulfonate ester compound comprising a structure of the following general formula (B):

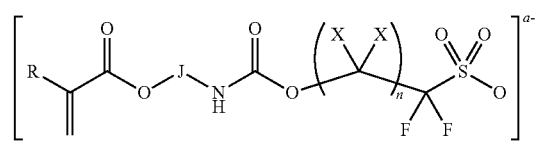

(B)

where X each independently represent a hydrogen atom or a fluorine atom; 71 represents an integer of 1 to 10; R represents a hydrogen atom, a halogen atom or a $C_1$-$C_3$ alkyl or fluorine-containing alkyl group; J represents a divalent linking group; and a represents 0 or 1.

[Inventive Aspect 20]

A polymerizable fluorine-containing sulfonic acid or sulfonate salt having a structure of the following general formula (1-1):

(1-1)

where X each independently represents a hydrogen atom or a fluorine atom; n represents an integer of 1 to 10; R represents a hydrogen atom, a halogen atom or a $C_1$-$C_3$ alkyl or fluorine-containing alkyl group; J represents a divalent linking group; and $M^+$ represents a monovalent cation.

[Inventive Aspect 21]

The polymerizable fluorine-containing sulfonate according to Inventive Aspect 19 or 20, wherein the structure is of the following general formula (2):

(2)

where X, n, R and J have the same definitions as in the general formula (B) or (1-1); and Q' represents either a sulfonium cation of the following general formula (a) or a iodonium cation of the following general formula (b);

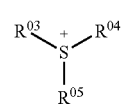

(a)

where $R^{03}$, $R^{04}$ and $R^{05}$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of $R^{03}$, $R^{04}$ and $R^{05}$ may be bonded together to form a ring with a sulfur atom in the formula,

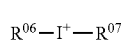

(b)

where $R^{06}$ and $R^{07}$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^{06}$ and $R^{07}$ may be bonded together to form a ring with a iodine atom in the formula.

[Inventive Aspect 22]

A polymerizable fluorine-containing N-sulfonyloxyimide compound having a structure of the following general formula (18):

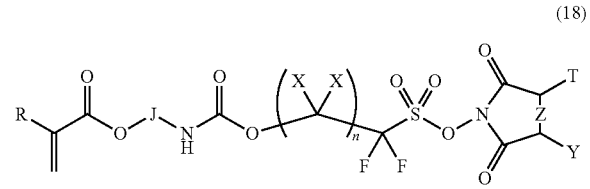

(18)

where X each independently represent a hydrogen atom or a fluorine atom; n represents an integer of 1 to 10; R represents a hydrogen atom, a halogen atom or a $C_1$-$C_3$ alkyl or fluorine-containing alkyl group; J represents a divalent linking group; Z represents a single bond, a double bond, a methylene group or an oxygen atom; T and Y each independently represent a hydrogen atom or a substituted or unsubstituted $C_1$-$C_{10}$ alkyl group and may form an aliphatic cyclic structure, an aromatic ring structure or a heterocyclic structure in combination thereof with carbon atoms to which T and Y are bonded.

The positive or negative resist composition according to the present invention is prepared from the resin having a repeating unit of novel fluorine-containing sulfonate structure or fluorine-containing N-sulfonyloxyimide structure. It is therefore possible that the resist composition can attain high resolution, wide DOF, small LER and high sensitivity and form a good pattern shape.

DETAILED DESCRIPTION

Hereinafter, embodiments of the present invention will be described below in detail. It should be however understood that: the present invention is not limited to the following embodiments; various changes and modifications can be made on the following embodiments as appropriate, without departing from the scope of the present invention, based on the ordinary knowledge of those skilled in the art.

In the present specification, the following terms have the following meanings. The term "base resin" means a resin capable of changing its developer solubility by exposure. The term "positive resist" means a resist whose exposed portion is more soluble in a developer than its unexposed portion, whereas the term "negative resist" means a resist whose exposed portion is less soluble in a developer than its unexposed portion. The term "high energy radiation" means electromagnetic wave generated by excimer laser e.g. KrF excimer laser, ArF excimer laser or $F_2$ excimer laser or by synchrotron radiation, such as near-ultraviolet radiation, far-ultraviolet radiation, extreme-ultraviolet radiation (EUV), soft X-ray, X-ray or γ-ray, or charged particle beam such as electron beam. Unless otherwise specified, the term "salt" means that the cation of the salt can be $H^+$.

A material relationship of the present invention is indicated in Schemes (1) and (3).

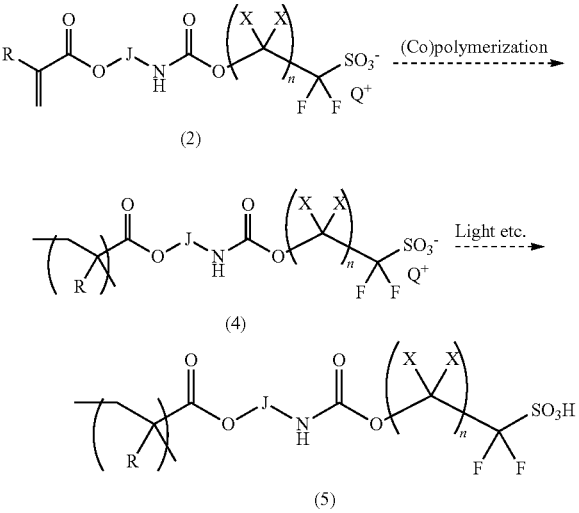

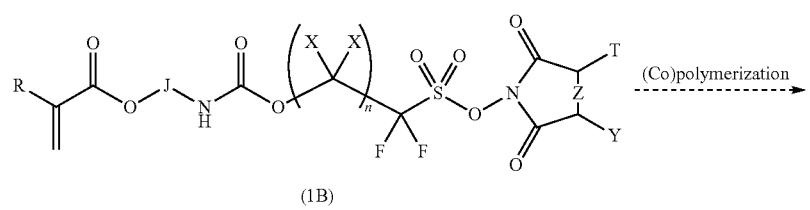

-continued

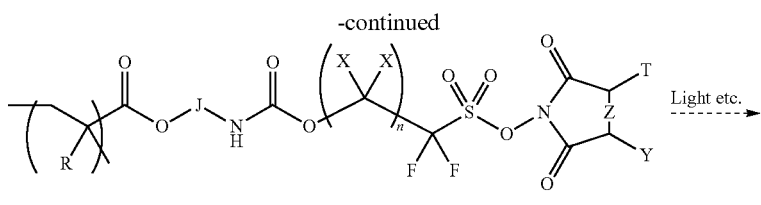

(17)

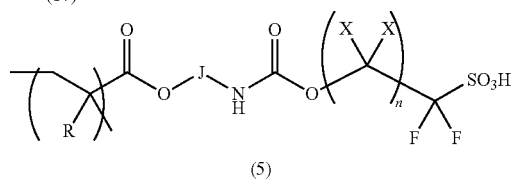

(5)

As shown in Scheme 1, a sulfonate resin having a repeating unit of the general formula (4) is obtained by homopolymerization or copolymerization of a polymerizable fluorine-containing sulfonic acid onium salt of the general formula (2) and is converted to a resin having a repeating unit of the general formula (5) by the action of high energy radiation, heat etc. The thus-generated fluorine-containing sulfonic acid serves as an acid catalyst.

Similarly, a fluorine-containing N-sulfonyloxyimide resin having a repeating unit of the general formula (17) is obtained by homopolymerization or copolymerization of a polymerizable fluorine-containing N-sulfonyloxyimide compound of the general formula (18) and is converted to a fluorine-containing sulfonate resin having a repeating unit of the general formula (5) as shown in Scheme 3. The thus-generated fluorine-containing sulfonic acid also serves as an acid catalyst.

[Polymerizable Fluorine-Containing Sulfonic Acid or Sulfonate]

A polymerizable fluorine-containing sulfonic acid or sulfonate having a structure of the general formula (1) will be first described below.

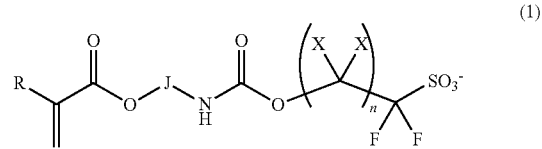

(1)

The polymerizable fluorine-containing sulfonic acid or sulfonate having the structure of the general formula (1) is a polymerizable fluorine-containing sulfonic acid or sulfonate of the general formula (1-1).

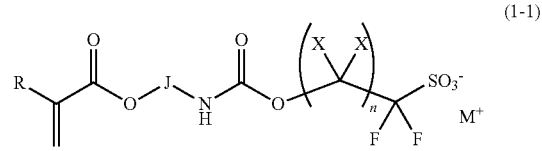

(1-1)

In the general formula (1-1), $M^+$ represents a proton, a metal cation such as lithium ion, sodium ion or potassium ion, or a monovalent cation such as an onium ion, e.g., ammonium ion, sulfonium ion, iodonium ion or phosphonium ion. In the general formula (1) and in the general formula (1-1), X each independently represent a hydrogen atom or a fluorine atom; and n represents an integer of 1 to 10, preferably an integer of 1 to 7, more preferably an integer of 1 to 4. The structure represented by $—(CX_2)_n—$ in the general formula (1) and in the general formula (1-1) is thus a $C_1$-$C_{10}$ straight alkylene group in which any number of hydrogen atoms may be substituted with a fluorine atom. Among others, preferred are those having a structure represented by $—(CH_2)_p—(CF_2)_q—$ where p represents an integer of 0 to 10; and q represents an integer of 0 to 7. It is preferable that p is an integer of 1 to 5 and q is an integer of 0 to 4, respectively. It is more preferable that p is an integer of 1 to 3 and q is 0 or 1. Further, R represents a hydrogen atom, a fluorine atom or a $C_1$-$C_3$ alkyl or fluorine-containing alkyl group; and J represents a divalent linking group in the general formula (1) and in the general formula (1-1).

Examples of the halogen atom as R are fluorine, chlorine, bromine and iodine. Examples of the $C_1$-$C_3$ alkyl group as R are methyl, ethyl, n-propyl and i-propyl. Examples of the $C_1$-$C_3$ fluorine-containing alkyl group as R are fluoromethyl, difluoromethyl, trifluoromethyl, 2-fluoroethyl, 2,2-difluoroethyl, 2,2,2-trifluoroethyl, pentafluoroethyl, 1-methyl-2,2,2-trifluoroethyl, 1-(trifluoromethyl)-2,2,2-trifluoroethyl and 1-(trifluoromethyl)-1,2,2,2-tetrafluoroethyl. Among others, preferred as R are a hydrogen atom, a fluorine atom, a methyl group and a trifluoromethyl group.

Examples of the divalent linking group J are: linking groups such as a substituted or unsubstituted methylene group, a substituted or unsubstituted divalent alicyclic hydrocarbon group, a substituted or unsubstituted divalent aromatic hydrocarbon group and a substituted or unsubstituted heterocyclic group; and divalent linking groups each formed by combination of the above linking group with one or more kinds of linking groups selected from an ether bond, a thio-ether bond, a carbonyl group, an ester group, an oxycarbonyl group, an amide group, a sulfoneamide group, an urethane group and an urea group. Any number of hydrogen atoms bonded to carbon atoms of the divalent linking group may be substituted with a fluorine atom. Any carbon atoms may form a ring with or without a substituent in the divalent linking group.

The substituted methylene group, as the constituent of the divalent linking group J, is represented by the following general formula (13).

$$—CR^{13}R^{14}—$$ (13)

Although there is no particular limitation on the monovalent group $R^{13}$, $R^{14}$ in the substituted methylene group, $R^{13}$ and $R^{14}$ each independently represent a hydrogen atom, a halogen atom, a hydroxy group or a monovalent $C_1$-$C_{30}$ group selected from the group consisting of a substituted or unsubstituted alkyl group, a substituted or unsubstituted aliphatic hydrocarbon group, an alkoxy group, a substituted or unsubstituted aryl group and a substituted or unsubstituted condensed polycyclic aromatic group. Each of these monovalent groups may contain a fluorine atom, an oxygen atom, a sulfur atom, a nitrogen atom or a carbon-carbon double bond. Further, $R^{13}$ and $R^{14}$ may be the same or different and may form a ring structure, preferably an alicyclic hydrocarbon structure, with any atom in the molecule. The monovalent organic group as $R^{13}$, $R^{14}$ is exemplified as follows.

The acyclic alkyl group as $R^{13}$, $R^{14}$ is of 1 to 30 carbon atoms, preferably 1 to 12 carbon atoms. Examples of the acyclic alkyl group as $R^{13}$, $R^{14}$ are methyl, ethyl, n-propyl, i-propyl, n-butyl, 1-methylpropyl, 2-methylpropyl, tert-butyl, n-pentyl, i-pentyl, 1,1-dimethylpropyl, 1-methylbutyl, 1,1-dimethylbutyl, n-hexyl, n-heptyl, i-hexyl, n-octyl, i-octyl, 2-ethylhexyl, n-nonyl, n-decyl, n-undecyl and n-dodecyl. Among others, lower alkyl groups are preferred. Particularly preferred are methyl, ethyl, n-propyl and i-propyl. In the present specification, the term "lower" means that the group to which the term is attached has 1 to 4 carbon atoms and, in the case where the group is cyclic, has 3 to 7 carbon atoms.

The acyclic substituted alkyl group as $R^{13}$, $R^{14}$ is that obtained by substitution of one hydrogen atom or two or more hydrogen atoms of the above alkyl group with a $C_1$-$C_4$ alkoxy group, a halogen atom, an acyl group, an acyloxy group, a cyano group, a hydroxy group, a carboxy group, an alkoxycarbonyl group, a nitro group or the like, and is preferably a fluorine-substituted alkyl group, i.e., fluoroalkyl group. Examples of the acyclic substituted alkyl group as $R^{13}$, $R^{14}$ are lower fluoroalkyl groups such as trifluoromethyl, pentafluoroethyl, 2,2,2-trifluoroethyl, n-heptafluoropropyl, 2,2,3,3,3-pentafluoropropyl, 3,3,3-trifluoropropyl and hexafluoropropyl.

The alicyclic hydrocarbon group as $R^{13}$, $R^{14}$ or the alicyclic hydrocarbon group formed by $R^{13}$ and $R^{14}$ together with the carbon atom bonded thereto may be monocyclic or polycyclic. Examples of the alicyclic hydrocarbon group are those having a monocyclo, bicyclo, tricycle or tetracyclo structure of 3 or more carbon atoms, preferably 3 to 30 carbon atoms, more preferably 3 to 25 carbon atoms. The alicyclic hydrocarbon group may have a substituent.

As the monocyclic hydrocarbon group, there can preferably be used those having 3 to 12 ring carbon atoms, more preferably 3 to 7 ring carbon atoms. Examples of such a monocyclic hydrocarbon group are cyclopropyl, cyclobutyl, cyclopentyl, cyclohexyl, cycloheptyl, cyclooctyl, cyclodecanyl, cyclododecanyl, and 4-tert-butylcyclohexyl. As the polycyclic hydrocarbon group, there can preferably be used those having 7 to 15 ring carbon atoms. Examples of such a polycyclic hydrocarbon group are adamantyl, noradamantyl, decalin residue, tricyclodecanyl, tetracyclododecanyl, norbornyl and cedrol. The alicyclic hydrocarbon group can be a Spiro ring preferably having 3 to 6 carbon atoms. Preferred examples of such a spiro ring are adamantyl, decalin residue, norbornyl, cedrol, cyclohexyl, cycloheptyl, cyclooctyl, cyclodecanyl, cyclododecanyl and tricyclodecanyl. One or two or more hydrogen atoms on the ring carbons of the above organic group, or one or two or more hydrogen atoms of the above linking group, may be each independently substituted with a substituent such as $C_1$-$C_{30}$ alkyl or substituted alkyl group, hydroxy group, alkoxy group, carboxyl group or alkoxycarbonyl group. One or two or more hydrogen atoms of the substituent may further be substituted with fluorine or trifluoromethyl.

Herein, the $C_1$-$C_{30}$ alkyl group is preferably a lower alkyl group, more preferably an alkyl group selected from the group consisting of methyl, ethyl, propyl and isopropyl. As the substituent of the substituted alkyl group, there can be used a hydroxy group, a halogen atom, an alkoxy group and the like. The alkoxy group is, for example, of 1 to 4 carbon atoms, as exemplified by methoxy, ethoxy, propoxy and butoxy. The alkoxy carbonyl group is, for example, exemplified by methoxycarbonyl, ethoxycarbonyl and isopropoxycarbonyl.

Examples of the alkoxy group as $R^{13}$, $R^{14}$ are those of 1 to 4 carbon atoms, such as methoxy, ethoxy, propoxy and butoxy.

The substituted or unsubstituted aryl group as $R^{13}$, $R^{14}$ is of 1 to 30 carbon atoms. It is preferable that, when the aryl group is monocyclic, the monocyclic aryl group has 3 to 12 ring carbon atoms, more preferably 3 to 6 ring carbon atoms. Examples of the substituted or unsubstituted aryl group as $R^{13}$, $R^{14}$ are phenyl, biphenyl, terphenyl, o-tolyl, m-tolyl, p-tolyl, p-hydroxyphenyl, p-methoxyphenyl, mesityl, o-cumenyl, 2,3-xylyl, 2,4-xylyl, 2,5-xylyl, 2,6-xylyl, 3,4-xylyl, 3,5-xylyl, o-fluorophenyl, m-fluorophenyl, p-fluorophenyl, o-trifluoromethylphenyl, m-trifluoromethylphenyl, p-trifluoromethylphenyl, 2,3-bistrifluoromethylphenyl, 2,4-bistrifluoromethylphenyl, 2,5-bistrifluoromethylphenyl, 2,6-bistrifluoromethylphenyl, 3,4-bistrifluoromethylphenyl, 3,5-bistrifluoromethylphenyl, p-chlorophenyl, p-bromophenyl and p-iodophenyl.

Examples of the substituted or unsubstituted $C_1$-$C_{30}$ condensed polycyclic aromatic group are monovalent organic groups obtained by elimination of one hydrogen atom from pentalene, indene, naphthalene, azulene, heptalene, biphenylene, indacene, acenaphthylene, fluorine, phenalene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene and the like, in each of which one hydrogen atom or two or more hydrogen atoms may preferably be substituted with a fluorine atom or a $C_1$-$C_4$ alkyl or fluorine-containing alkyl group.

Examples of the monocyclic or polycyclic heterocyclic group are those of 3 to 25 ring carbon atoms, such as pyridyl, furyl, thienyl, pyranyl, pyrrolyl, thianthrenyl, pyrazolyl, isothiazolyl, isoxazolyl, pyrazinyl, pyrimidinyl, pyridazinyl, tetrahydropyranyl, tetrahydrofuranyl, tetrahydrothiopyranyl, tetrahydrothiofuranyl and 3-tetrahydrothiophene-1,1-dioxide. One hydrogen atom or two or more hydrogen atoms on the ring structure of the above heterocyclic group may be each independently substituted with an alkyl group, an alicyclic hydrocarbon group, an aryl group or a heterocyclic group. Among others, preferred are those having a monocyclic or polycyclic ether ring or lactone ring as exemplified as follows.

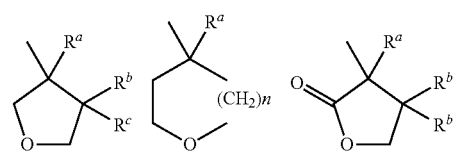

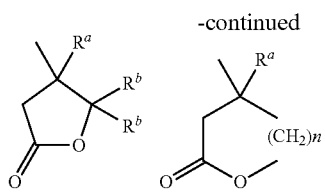

In the above formulas, $R^a$ and $R^b$ each independently represent a hydrogen atom or a $C_1$-$C_4$ alkyl group; and n represents an integer of 2 to 4.

The divalent alicyclic hydrocarbon group, constituting the main skeleton of the linking group J, can be either monocyclic or polycyclic. More specifically, the divalent alicyclic hydrocarbon group can be any of those having a monocyclo, bicycle, tricycle or tetracyclo structure of 3 or more carbon atoms, preferably 3 to 30 carbon atoms, more preferably 3 to 25 carbon atoms. The divalent alicyclic hydrocarbon group may have a substituent.

The alicyclic hydrocarbon group, when it is monocyclic, preferably has 3 to 12 ring carbon atoms, more preferably 3 to 7 ring carbon atoms. Examples of the monocyclic alicyclic hydrocarbon group are cyclopropylene, cyclobutylene, cyclopentylene, cyclohexylene, cycloheptylene, cyclooctylene, cyclodecanylene, cyclododecanylene and 4-tert-butylcyclohexylene. The alicyclic hydrocarbon group, when it is polycyclic, has e.g. 7 to 15 ring carbon atoms. Examples of the polycyclic alicyclic hydrocarbon group are adamantylene, noradamantylene, divalent decalin residue, tricyclodecanylene, tetracyclododecanylene, norbornylene and divalent cedrol residue. The alicyclic hydrocarbon group may be a spiro ring preferably of 3 to 6 carbon atoms. One hydrogen atom or two or more hydrogen atoms on the linking group or the ring carbon(s) of the organic group may be each independently substituted with a substituent such as $C_1$-$C_{30}$ alkyl group or substituted alkyl group, hydroxy group, alkoxyl group, carboxyl group or alkoxycarbonyl group.

The $C_1$-$C_{30}$ alkyl group is preferably a lower alkyl group, more preferably an alkyl group selected from the group consisting of methyl, ethyl, propyl and isopropyl. As the substituent of the substituted alkyl group, there can be used a hydroxy group, a halogen atom, an alkoxyl group and the like. The alkoxyl group is, for example, of 1 to 4 carbon atoms, as exemplified by methoxy, ethoxy, propoxy and butoxy. The alkoxycarbonyl group is, for example, exemplified by methoxycarbonyl, ethoxycarbonyl and isopropoxycarbony.

The divalent aromatic hydrocarbon group, constituting the main skeleton of the linking group J, can be in the form of a monocyclic or condensed polycyclic aromatic ring structure of 1 to 30 carbon atoms. The aromatic hydrocarbon group, when it is monocyclic, preferably has 3 to 12 ring carbon atoms, more preferably 3 to 6 ring carbon atoms. Examples of the monocyclic aromatic hydrocarbon group are divalent groups obtained by elimination of two hydrogen atoms from benzene, biphenyl, terphenyl, toluene, phenol, anisole, mesitylene, cumene, 2,3-xylylene, 2,4-xylene, 2,5-xylene, 2,6-xylene, 3,4-xylene, 3,5-xylene, fluorobenzene, trifluoromethylbenzene, o-bistrifluoromethylbenzene, m-bistrifluoromethylbenzene, p-bistrifluoromethylbenzene, chlorobenzene, bromobenzene, iodobenzene and the like.

The condensed polycyclic aromatic group can be substituted or unsubstituted and preferably has 1 to 30 carbon atoms. Examples of the condensed polycyclic aromatic group are divalent organic groups obtained by elimination of two hydrogen atoms from pentalene, indene, naphthalene, azulene, heptalene, biphenylene, indacene, acenaphthylene, fluorene, phenalene, phenanthrene, anthracene, fluoranthene, acephenanthrylene, aceanthrylene, triphenylene, pyrene, chrysene, naphthacene, picene, perylene, pentaphene, pentacene, tetraphenylene, hexaphene, hexacene, rubicene, coronene, trinaphthylene, heptaphene, heptacene, pyranthrene, ovalene etc. One hydrogen atom or two or more hydrogen atoms of the above divalent organic group may be each independently substituted with a fluorine atom or a $C_1$-$C_4$ alkyl group or fluorine-containing alkyl group.

The heterocyclic group, constituting the main skeleton of the linking group J, can be in the form of a monocyclic or polycyclic ring structure of 3 to 25 ring carbon atoms. The ring structure may be aromatic or nonaromatic. Examples of the monocyclic or polycyclic heterocyclic group are divalent organic groups obtained by elimination of two hydrogen atoms from pyridine, furan, thienine, pyranine, pyrroline, thianthrene, pyrazon, isothiazone, isooxazone, pyrazine, pyrimidine, pyridazine, tetrahydropyranine, tetrahydrofuranine, tetrahydrothiopyranine, tetrahydrothiofuranine and the like. One hydrogen atom or two or more hydrogen atoms on the ring atom of the above divalent organic group may be each independently substituted with an alkyl group (preferably, a lower alkyl group), an alicyclic hydrocarbon group, an aryl group or a heterocyclic group. Among others, preferred are monocyclic or polycyclic ether rings as exemplified below. In the respective formulas, open-ended lines indicate uncombined hands.

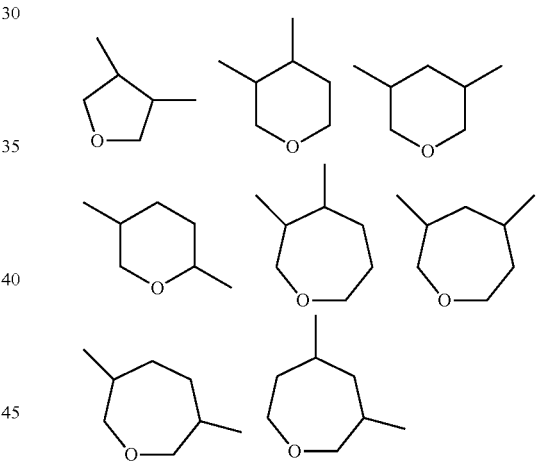

As mentioned above, the divalent linking group J may be a divalent linking group formed by combination of any of the divalent groups explained above by the general formulas or specifically exemplified above with one or more kinds of linking groups selected from an ether bond, a thioether bond, a carbonyl group, an ester group, an oxycarbonyl group, an amide group, a sulfoneamide group, an urethane group and an urea group.

The resin containing a sulfonic acid onium salt as a chemically amplified photoacid generator in a side chain thereof characteristically show wide DOF and small LER due to the substantially limited diffusion length of the acid. It is however feasible to adjust the ease of diffusion and diffusion length of the acid by applying the above structure to the linking group between the acid moiety and main chain of the resin.

The structure of the general formula (1) is thus exemplified as follows. The fluorine-containing sulfonic acid or sulfonate of the general formula (1-1) corresponds to that in which a cation $M^+$ is bonded to any of the following anion structures.

The fluorine-containing sulfonic acid onium salt of the general formula (2) corresponds to that in which a cation $Q^+$ is bonded to any of the following anion structures.
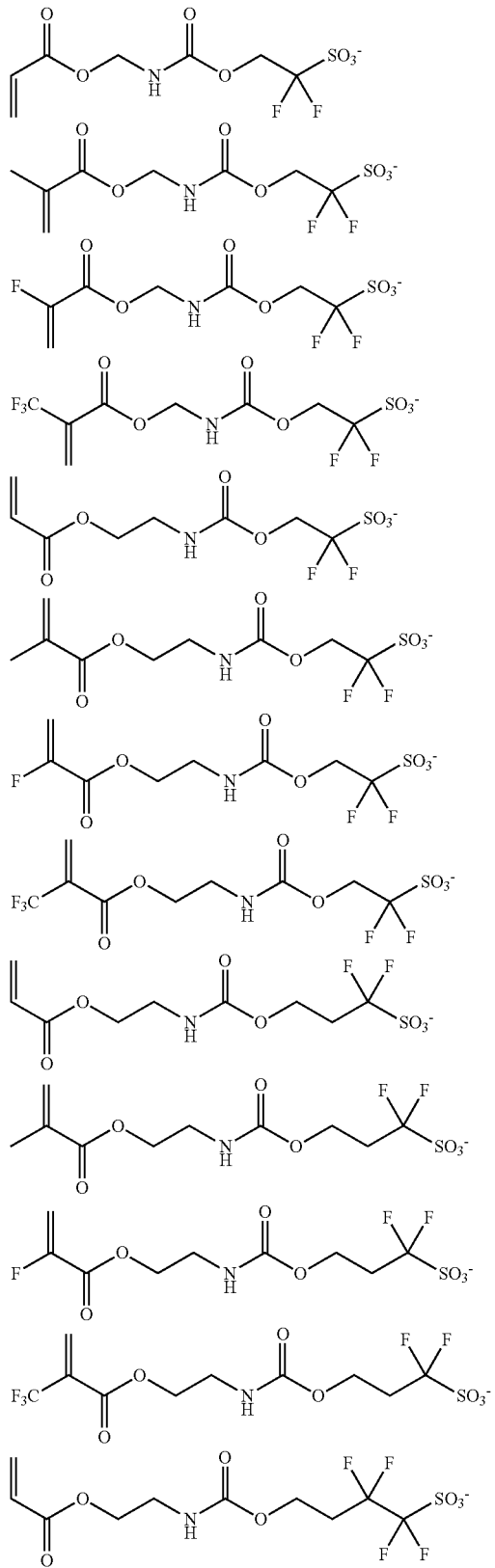
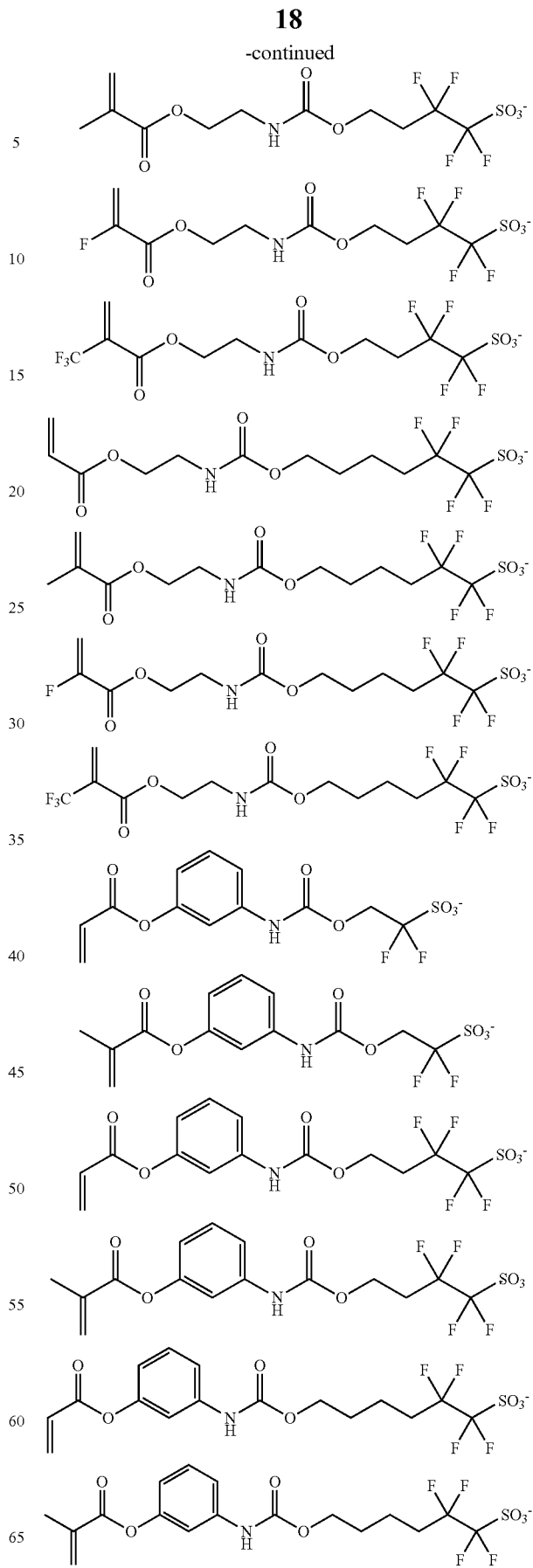

-continued

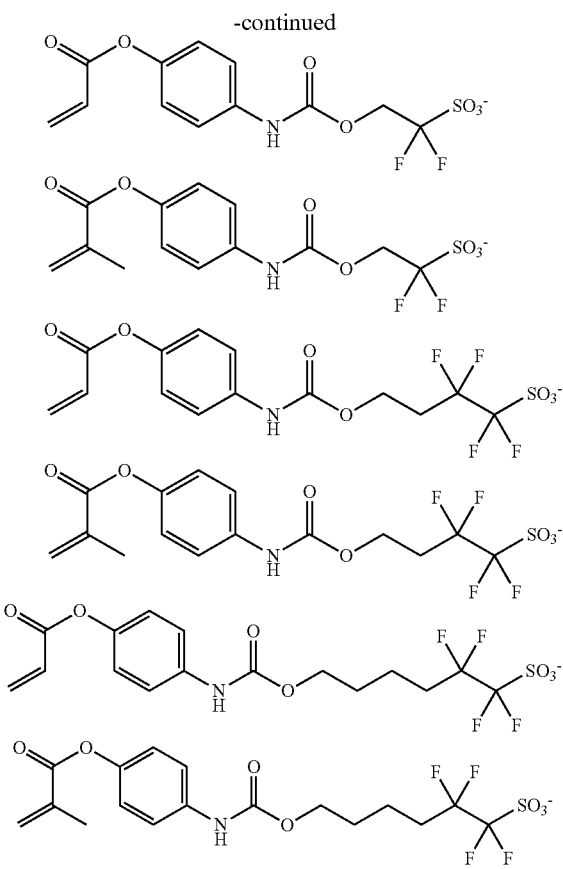

[Polymerizable Fluorine-containing Sulfonic Acid Onium Salt]

The polymerizable fluorine-containing sulfonic acid onium salt of the general formula (2) is one preferred example of the polymerizable fluorine-containing sulfonate having the structure of the general formula (1) according to the present invention. The polymerizable fluorine-containing sulfonic acid onium salt, in the form of either a monomer or a resin obtained by homopolymerization or copolymerization thereof, is capable of sensing high energy radiation and thereby generating a fluorine-containing sulfonic acid of high acidity. The polymerizable fluorine-containing sulfonic acid onium salt or the resin obtained therefrom can be thus suitably used a photoacid generator. Further, the polymerizable fluorine-containing sulfonic acid onium salt is copolymerizable with a monomer having an acid labile group or cross-linking site and thus can be also suitably used as a monomer for preparation of a base resin of a high-energy radiation resist composition.

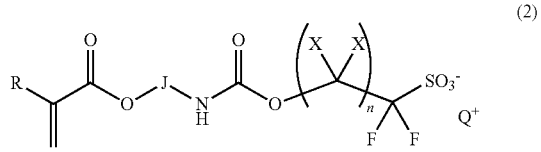

(2)

In the general formula (2), X, n, R and J have the same definitions as in the general formula (1); and $Q^+$ represents either a sulfonium cation of the following general formula (a) or a iodonium cation of the following general formula (b).

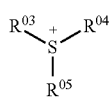

(a)

In the general formula (a), $R^{03}$, $R^{04}$ and $R^{05}$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and two or more of $R^{03}$, $R^{04}$ and $R^{05}$ may be bonded together to form a ring with a sulfur atom in the formula.

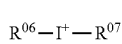

(b)

In the general formula (b), $R^{06}$ and $R^{07}$ each independently represent a substituted or unsubstituted $C_1$-$C_{20}$ alkyl, alkenyl or oxoalkyl group or a substituted or unsubstituted $C_6$-$C_{18}$ aryl, aralkyl or aryloxoalkyl group; and $R^{06}$ and $R^{07}$ may be bonded together to foam a ring with a iodine atom in the formula.

As specific structural examples of $Q^+$, the sulfonium cation of the general formula (a) and the iodonium cation of the general formula (b) will be described below in detail.

[Sulfonium Cation of General Formula (a)]

In the general formula (a), $R^{03}$, $R^{04}$ and $R^{05}$ are exemplified as follows. The substituted or unsubstituted $C_1$-$C_{20}$ alkyl group may be straight, branched or cyclic and may have a substituent. Examples of the substituted or unsubstituted $C_1$-$C_{20}$ alkyl group are methyl, ethyl, n-propyl, isopropyl, cyclopropyl, n-butyl, sec-butyl, isobutyl, tert-butyl, n-pentyl, cyclopentyl, n-hexyl, n-heptyl, 2-ethylhexyl, cyclohexyl, cycloheptyl, 4-methylcyclohexyl, cyclohexylmethyl, n-octyl, n-decyl, 1-adamantyl, 2-adamantyl, bicyclo[2.2.1]heptene-2-yl, 1-adamantanemethyl and 2-adamantanemethyl. The substituted or unsubstituted $C_1$-$C_{20}$ alkneyl group may be straight, branched or cyclic and may have a substituent. Examples of the substituted or unsubstituted $C_1$-$C_{20}$ alkenyl group are vinyl, allyl, propenyl, butenyl, hexenyl and cyclohexenyl. The substituted or unsubstituted $C_1$-$C_{20}$ oxoalkyl group may be straight, branched or cyclic and may have a substituent. Examples of the substituted or unsubstituted $C_1$-$C_{20}$ oxoalkyl group are 2-oxocyclopentyl, 2-oxocyclohexyl, 2-oxopropyl, 2-oxoethyl, 2-cyclopentyl-2-oxoethyl, 2-cyclohexyl-2-oxoethyl and 2-(4-methylcyclohexyl)-2-oxoethyl. Further, examples of the substituted or unsubstituted $C_6$-$C_{18}$ aryl group are: phenyl; naphthyl; thienyl; alkoxylphenyl groups such as p-methoxyphenyl, m-methoxyphenyl, o-methoxyphenyl, p-ethoxypenyl, p-tert-butoxyphenyl and m-tert-butoxyphenyl; alkylphenyl groups such as 2-methylphenyl, 3-methylphenyl, 4-methylphenyl and ethylphenyl; alkylnaphthyl groups such as methylnaphthyl and ethylnaphthyl; dialkylnaphthyl groups such as diethylnaphthyl; and dialkoxynaphthyl groups such as dimethoxynaphthyl and diethoxynaphthyl. Examples of the substituted or unsubstituted $C_6$-$C_{18}$ aralkyl group are benzyl, 1-phenylethyl and 2-phenylethyl. Examples of the substituted or unsubstituted $C_6$-$C_{18}$ aryloxoalkyl group are 2-aryl-2-oxoethyl groups such as 2-phenyl-2-oxoethyl, 2-(1-naphthyl)-2-oxoethyl and 2-(2-naphthyl)-2-oxoethyl. In the case where two or more of $R^{03}$, $R^{04}$ and $R^{05}$ are bonded to each other to form a ring with the sulfur atom, there can be used divalent groups such as 1,4-butylene and 3-oxa-1,5-penthylene. There can also be used aryl groups with polymerizable substituents such as acryloyloxy and methacryloyloxy. Examples of the aryl groups with the polymerizable substituents are 4-(acryloyloxy)phenyl, 4-(methacryloyloxy)phenyl, 4-vinyloxyphenyl and 4-vinylphenyl.

Specific examples of the sulfonium cation of the general foil mla (a) are triphenylsulfonium, (4-tert-butylphenyl)diphenylsulfonium, bis(4-tert-butylphenyl)phenylsulfonium, tris(4-tert-butylphenyl)sulfonium, (3-tert-butylphenyl)diphenylsulfonium, bis(3-tert-butylphenyl)phenylsulfonium, tris(3-tert-butylphenyl)sulfonium, (3,4-di-tert-butylphenyl)diphenylsulfonium, bis(3,4-di-tert-butylphenyl)phenylsulfonium, tris(3,4-di-tert-butylphenyl)sulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)diphenylsulfonium, (4-tert-butoxyphenyl)bis(4-dimethylaminophenyl)sulfonium, tris(4-dimethylaminophenyl)sulfonium, 2-naphthyldiphenylsulfonium, dimethyl(2-naphthyl)sulfonium, (4-hydroxyphenyl)dimethylsulfonium, (4-methoxyphenyl)dimethylsulfonium, trimethylsulfonium, (2-oxocyclohexyl)cyclohexylmethylsulfonium, trinaphthylsulfonium, tribenzylsulfonium, diphenylmethylsulfonium, dimethylphenylsulfonium, 2-oxo-2-phenylethylthiacyclopentanium, diphenyl 2-thienylsulfonium, 4-n-butoxynaphthyl-1-thiacyclopentanium, 2-n-butoxynaphthyl-1-thiacyclopentanium, 4-methoxynaphthyl-1-thiacyclopentanium, 2-methoxynaphthyl-1-thiacyclopentanium, 5-phenyldibenzothiophenium, 5-(4-methylphenyl)dibenzothiophenium, 5-(4-methoxyphenyl)dibenzothiophenium, 5-(3-methoxyphenyl)dibenzothiophenium, 5-(2-methoxyphenyl)dibenzothiophenium, 5-(4-fluorophenyl)dibenzothiophenium, 5-(4-chlorophenyl)dibenzothiophenium, 5-(4-hydroxyphenyl)dibenzothiophenium, 5-(4-hydroxy-3,5-dimethylphenyl)benzothiophenium, 2-methoxy-5-phenyldibenzothiophenium, tolyldiphenylsulfonium and (4-tert-butylphenyl)tetramethylene sulfide. Among others, preferred are triphenylsulfonium, (4-tert-butylphenyl)diphenylsulfonium, (4-tert-butoxyphenyl)diphenylsulfonium, tris(4-tert-butylphenyl)sulfonium, (4-tert-butoxycarbonylmethyloxyphenyl)diphenylsulfonium, 5-phenyldibenzothiophenium, 5-(4-methylphenyl)dibenzothiophenium, 5-(4-methoxyphenyl)dibenzothiophenium, 5-(4-fluorophenyl)dibenzothiophenium, tolyldiphenylsulfonium and (4-tert-butylphenyl)tetramethylene sulfide.

Further, 4-(methacryloyloxy)phenyldiphenylsulfonium, 4-(acryloyloxy)phenyldiphenylsulfonium, 4-(methacryloyloxy)phenyldimethylsulfonium and 4-(acryloyloxy)phenyldimethylsulfonium are also specific examples of the sulfonium cation of the general formula (a). There can also be used polymerizable sulfonium cations disclosed in Japanese Laid-Open Patent Publication No. 4-230645 and Japanese Laid-Open Patent Publication No. 2005-84365.

[Iodonium Cation of General Formula (b)]

Examples of $R^{06}$ and $R^{07}$ in the general formula (b) are the same as those of $R^{03}$, $R^{04}$ and $R^{05}$ in the general formula (a).

Specific examples of the iodonium cation of the general formula (b) are bis(4-methylphenyl)iodonium, bis(4-ethylphenyl)iodonium, bis(4-tert-butylphenyl)iodonium, bis(4-(1,1-dimethylpropyl)phenyl)iodonium, (4-methoxyphenyl)phenyliodonium, (4-tert-butoxyphenyl)phenyliodonium, (4-acryloyloxy)phenylphenyliodonium and (4-methacryloyloxy)phenylphenyliodonium. Among others, bis(4-tert-butylphenyl)iodonium is preferred.

More specifically, the polymerizable fluorine-containing sulfonic acid onium salt of the general formula (2) can be exemplified by the combination of the forementioned polymerizable fluorine-containing sulfonate having the structure of the general formula (1) with either the sulfonium cation of the general formula (a) or the iodonium cation of the general formula (b) mentioned above.

The following are particularly preferred examples of the polymerizable fluorine-containing sulfonic acid onium salt.

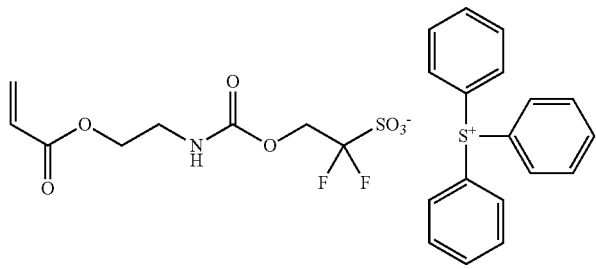

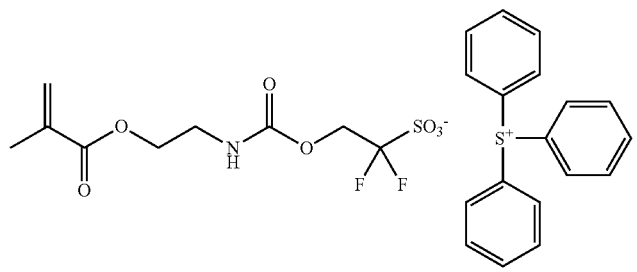

-continued
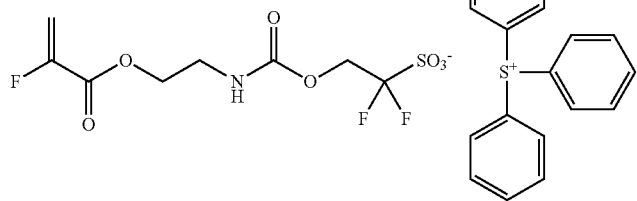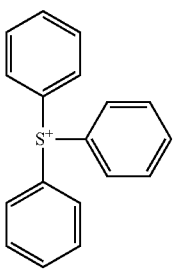
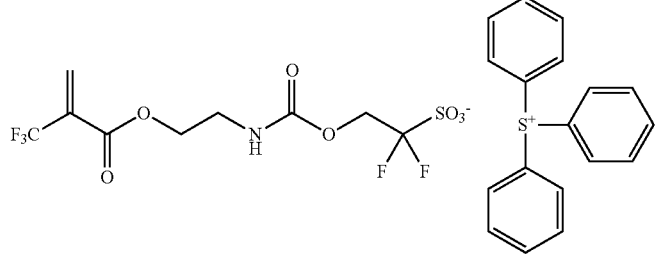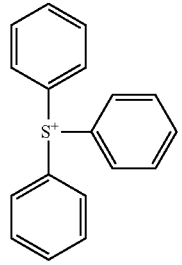
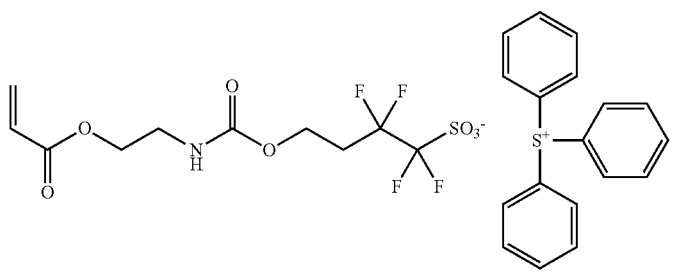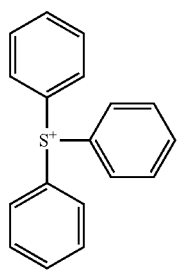
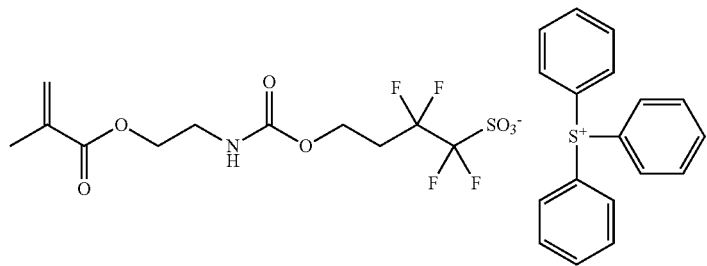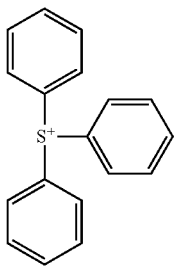
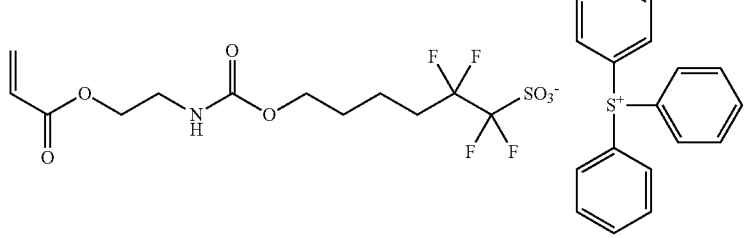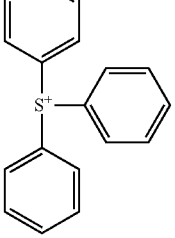
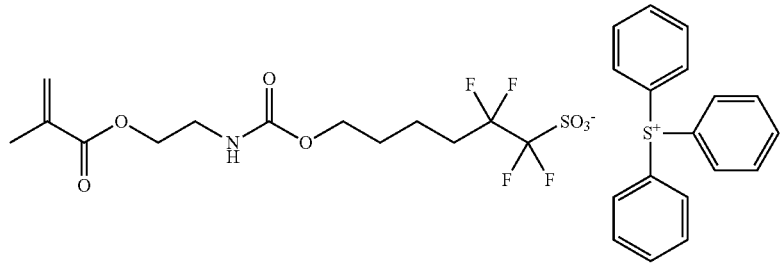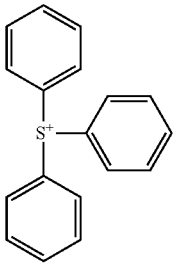

-continued
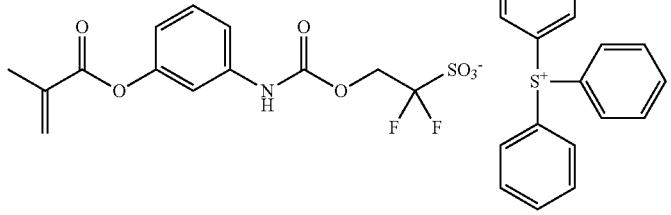
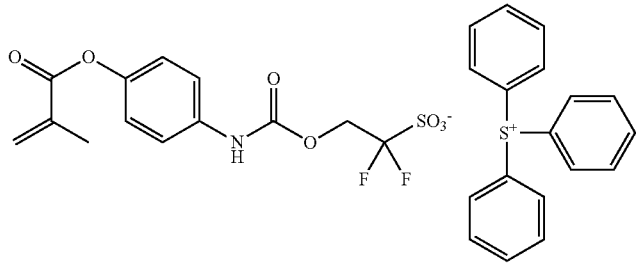
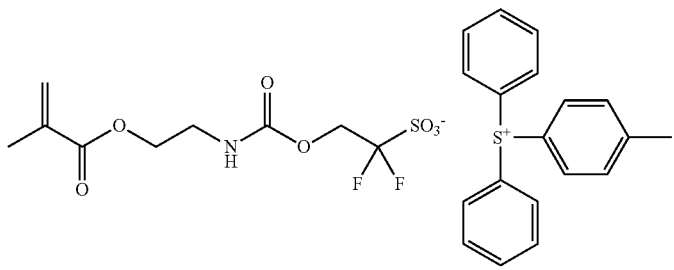
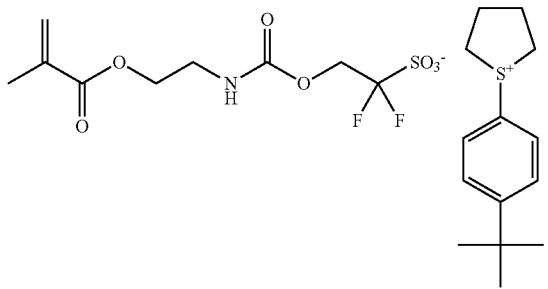
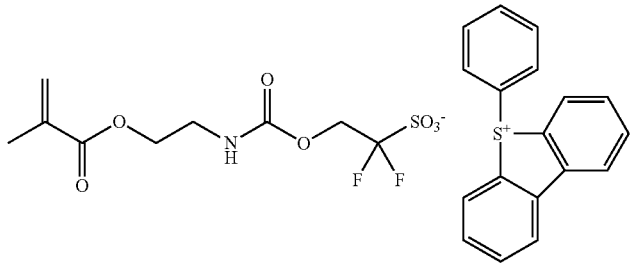
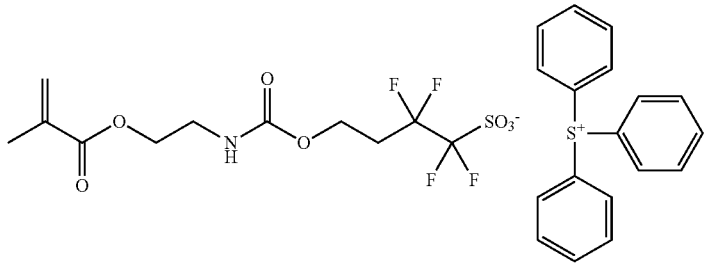

-continued
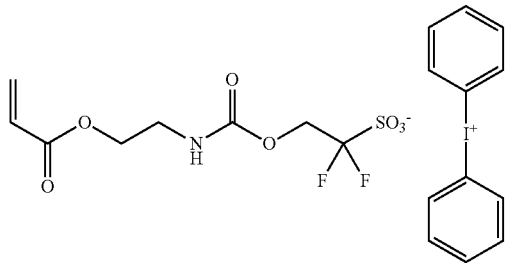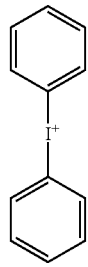
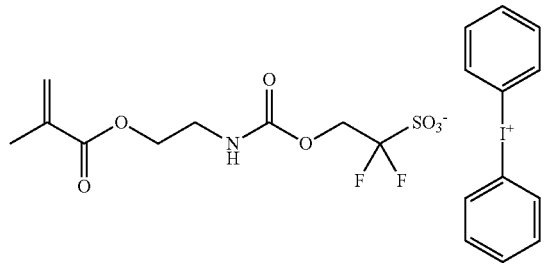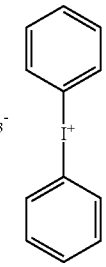
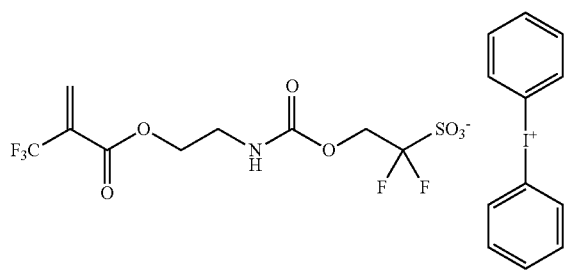
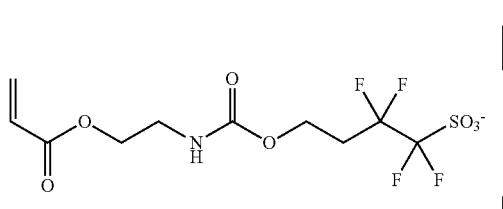
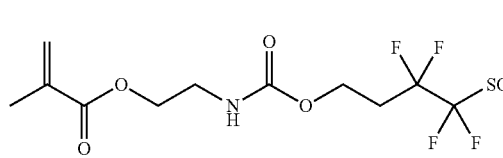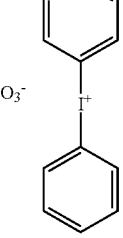
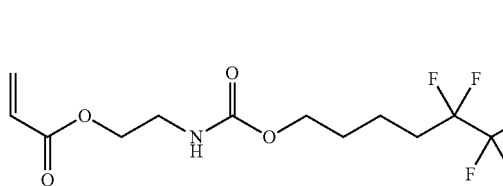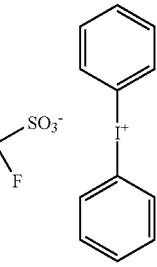

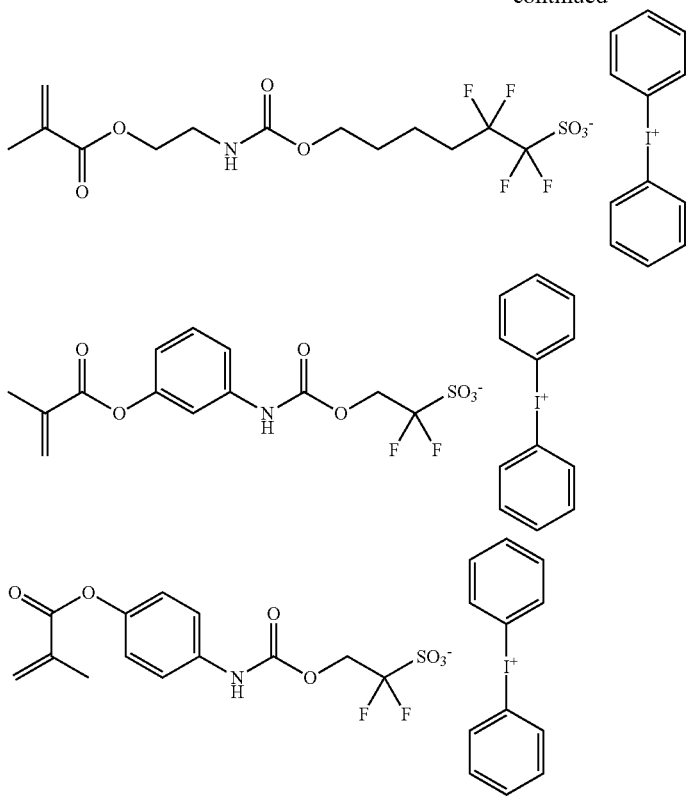

[Production Method of Polymerizable Fluorine-Containing Sulfonate]

Next, a production method of the above-mentioned polymerizable fluorine-containing sulfonate of the general formula (1) will be described below. It is feasible to produce the polymerizable fluorine-containing sulfonate of the general formula (1) in the same manner as the polymerizable fluorine-containing sulfonic acid onium salt of the general formula (2). In this case, $Q^+$ is read as $M^+$ in the following explanations.

The polymerizable fluorine-containing sulfonic acid onium salt of the general formula (2) is produced in one step from a compound of the general formula (14) and a compound of the general formula (15) as indicated in Scheme (2).

Scheme (2)

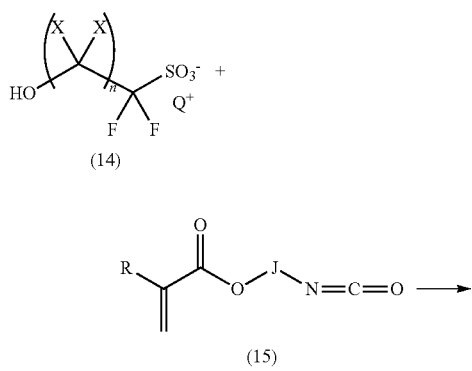

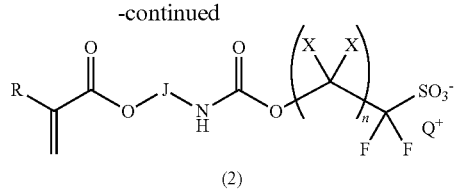

In Scheme (2), X, n, R, J and $Q^+$ have the same definitions as in the general formula (2).

The compound of the general formula (14) is a hydroxyfluoroalkanesulfonic acid onium salt. Herein, X represents a hydrogen atom or a fluorine atom; n represents an integer of 1 to 10; and $Q^+$ represents a sulfonium cation or a iodonium cation. Specific examples of the cation are the same as those in the explanation of the general formula (2).

As the hydroxyfluoroalkanesulfonic acid onium salt of the general formula (14), there can be used 2-hydroxy-1,1-difluoroethanesulfonic acid triphenylsulfonium, 4-hydroxy-1,1,2,2-tetrafluorobutanesulfonic acid triphenylsulfonium, 5-hydroxy-1,1,2,2-tetrafluoropentanesulfonic acid triphenylsulfonium and 6-hydroxy-1,1,2,2-tetrafluorohexanesulfonic acid triphenylsulfonium. These compounds can be produced by methods as disclosed in Japanese Laid-Open Patent Publication No. 2009-91351, International Application Publication No. WO 2008/56795, International Application Publication No. WO 2006/121096 and Japanese Laid-Open Patent Publication No. 2010-18573.

The compound of the general formula (15) is a polymerizable isocyanate derivative. Herein, R represents a hydrogen atom, a halogen atom or a $C_1$-$C_3$ alkyl or fluorine-containing alkyl group. Specific examples of R are the same as those in the explanation of the general formula (1). Further, J represents a divalent linking group. Specific examples of J are the same as those in the explanation of the general formula (1).

As the polymerizable isocyanate derivative of the general formula (15), there can be used 2-acryloyloxyethylisocyanate, 2-methacryloyloxyethylisocyanate, 2-acryloyloxypropylisocyanate, 3-acryloyloxyphenylisocyanate, 4-acryloyloxyphenylisocyanate, 3-methacryloyloxyphenylisocyanate and 4-methacryloyloxyphenylisocyanate. The compound of the general formula (15) can be commercially available and used as it is or can be prepared by known methods as disclosed in Japanese Laid-Open Patent Publication No. 2006-232797 and Japanese Laid-Open Patent Publication No. 2006-291188.

The reaction will be next explained below. In the reaction, a urethane bond is formed by addition of the hydroxyfluoroalkanesulfonic acid onium salt of the general formula (14) to the polymerizable isocyanate derivative of the general formula (15). This addition reaction can be performed by reacting the hydroxyfluoroalkanesulfonic acid onium salt of the general formula (14) with the polymerizable isocyanate derivative of the general formula (15) in the presence or absence of a catalyst.

There is no particular limitation on the amount of the polymerizable isocyanate derivative reacted with the hydroxyfluoroalkanesulfonic acid onium salt of the general formula (14). The amount of the polymerizable isocyanate derivative is generally 0.1 to 5 mol, preferably 0.2 to 3 mol, more preferably 0.5 to 2 mol, most preferably 0.8 to 1.5 mol, per 1 mol of the hydroxyfluoroalkanesulfonic acid onium salt.

The addition reaction can be performed in the presence or absence of a solvent. In general, it is preferable to perform the addition reaction with the use of an aprotic solvent. Examples of the aprotic solvent are diisopropyl ether, dichloroethane, chloroform, toluene, ethylbenzene, monochlorobenzene, acetonitrile and N,N-dimethylfoimamide. These solvents can be used solely or in combination of two or more kinds thereof. As the reaction is interfered with by the presence of water, it is preferable to dehydrate the solvent before use. In particular, the amount of water in the solvent is preferably 0.005 mass % or less, more preferably 0.002 mass % or less.

There is no particular limitation on the reaction temperature. The reaction temperature is generally 0 to 100° C., preferably 10 to 80° C. It is preferable to perform the reaction with stirring.

The reaction time is set depending on the reaction temperature and is generally several minutes to 100 hours, preferably 30 minutes to 50 hours, more preferably 1 to 20 hours. It is preferable to determine the time at which the polymerizable isocyanate derivative as the raw material has been consumed as the end of the reaction while monitoring the progress of the reaction by any analytical means such as nuclear magnetic resonance (NMR).

Although the reaction can be performed in the presence of no catalyst, the use of the catalyst leads to shortening of the reaction time and improvement of the reaction yield. Examples of the catalyst are: electron-donating amine compounds such as N,N-dimethyl-4-aminopyridine, 4-diethylaminopyridine, 4-aminopyridine, 2-aminopyridine, 2-hydroxypyridine, 2-methoxypyridine, 4-methoxypyridine, 4-hydroxypyridine, 2-dimethylaminoimidazole, 2-methoxyimidazole, 2-mercaptoimidazole, aminoquinoline, imidazole, 2-methylimidazole, 4-methylimidazole and diazabicyclooctane (DABCO); and organic tin compounds such as dibutyl tin dilaurate and dibutyl tin oxide. The amount of the catalyst used is generally 0.1 to 20 mol %, preferably 1 to 5 mol %, based on the hydroxyfluoroalkanesulfonic acid onium salt.

After the reaction, the target fluorine-containing sulfonic acid onium salt of the general formula (2) can be obtained by removing the solvent under a reduced pressure.

Further, the fluorine-containing sulfonic acid onium salt of the general formula (2) can be purified by ordinary means such as extraction or recrystallization after the reaction.

[Polymerizable Fluorine-containing N-Sulfonyloxyimide Compound]

A polymerizable fluorine-containing N-sulfonyloxyimide compound of the general formula (18) will be next described below.

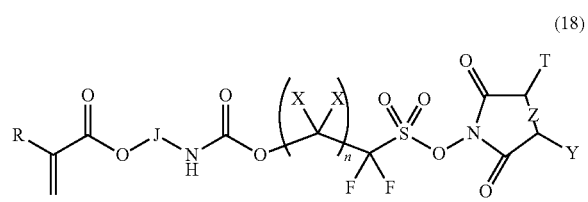

(18)

In the general formula (18), X, n, R and J have the same definitions as in the general formula (1); Z represents a single bond, a double bond, a methylene group or an oxygen atom; T and Y each independently represent a hydrogen atom or a substituted or unsubstituted $C_1$-$C_{10}$ alkyl group and may form an aliphatic cyclic structure, an aromatic ring structure or a heterocyclic structure in combination thereof with carbon atoms to which T and Y are bonded.

Examples of the unsubstituted $C_1$-$C_{10}$ alkyl group as T, Y are methyl, ethyl, n-propyl, i-propyl, n-butyl, t-butyl, n-pentyl, n-hexyl, n-heptyl, n-octyl, n-nonyl and n-decyl. Examples of the substituted alkyl group as T, Y are those obtained by substitution of a part or all of hydrogen atoms of the above unsubstituted alkyl groups with a hydroxyl group or carboxyl group or those having a keto group obtained by substitution of two hydrogen atoms on the same carbon atom of the above unsubstituted alkyl groups with an oxygen atom.

Examples of the aliphatic cyclic structure, aromatic ring structure or heterocyclic structure formed by T and Y in combination with the carbon atoms bonded thereto (the right side structure of the general formula (18)) are those exemplified below.

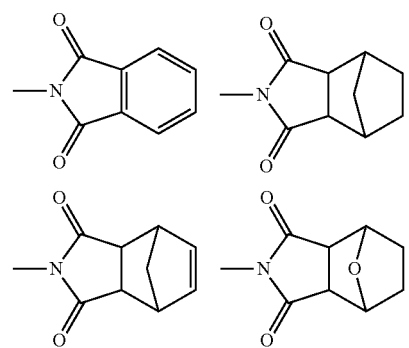

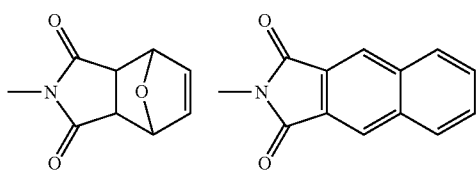

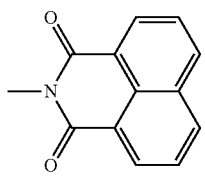

[Production Method of Polymerizable Fluorine-Containing N-Sulfonyloxyimide Compound]

Next, a production method of the polymerizable fluorine-containing N-sulfonyloxyimide compound of the general formula (18) will be described below. As indicated in Scheme (4), a hydroxyfluoroalkane N-sulfonyloxyimide compound of the general formula (22) is first produced from a sulfonyl chloride of the general formula (20) and a N-hydroxydicarboimide of the general formula (21) in a first step; and the polymerizable fluorine-containing N-sulfonyloxyimide compound of the general formula (18) is then produced by reaction of the hydroxyfluoroalkane N-sulfonyloxyimide compound of the general formula (22) with a polymerizable isocyanate derivative of the general formula (15) in a second step. It is herein noted that: this process is merely one example; and the production method of the polymerizable fluorine-containing N-sulfonyloxyimide compound is not limited to this process.

Scheme (4)

First step

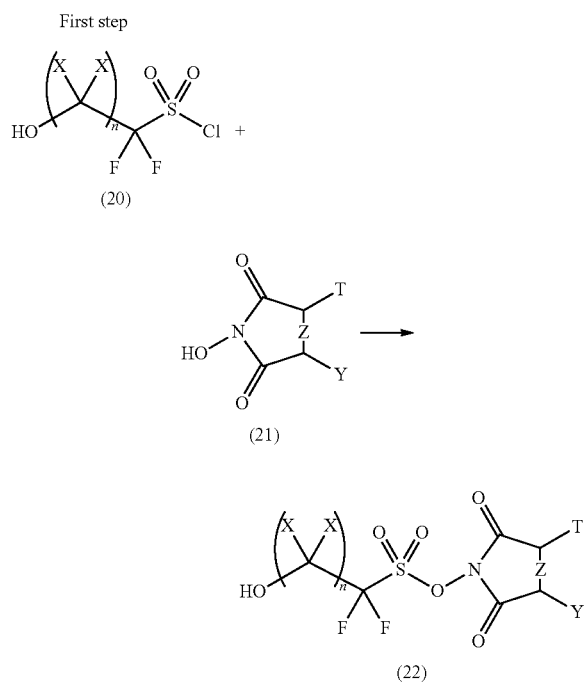

Second step

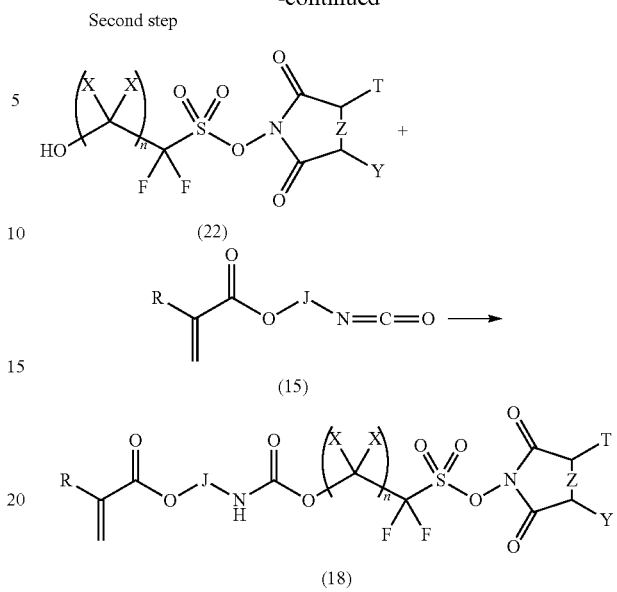

In Scheme (4), X, n, R and J have the same definitions as in the general formula (1); Z represents a single bond, a double bond, a methylene group or an oxygen atom; T and Y each independently represent a hydrogen atom or a substituted or unsubstituted $C_1$-$C_{10}$ alkyl group and may form an aliphatic cyclic structure, an aromatic ring structure or a heterocyclic structure in combination thereof with carbon atoms to which T and Y are bonded.

In the sulfonyl chloride of the general formula (20), X represents a hydrogen atom or a fluorine atom; and n represents an integer of 1 to 10.

As the sulfonyl chloride of the general formula (20), there can be used 1,1-difluoro-2-hydroxyethanesulfonyl chloride, 1,1,2,2-tetrafluoro-4-hydroxybutanesulfonyl chloride, 1,1,2,2-tetrafluoro-5-hydroxypentanesulfonyl chloride, 1,1,2,2-tetrafluoro-6-hydroxyhexanesulfonyl chloride and the like. These compounds can be produced by methods as disclosed in Japanese Laid-Open Patent Publication No. 2009-91351, International Application Publication No. WO 2008/56795, International Application Publication No. WO 2006/121096 and Japanese Laid-Open Patent Publication No. 2010-18573. The N-hydroxydicarboimide of the general formula (21) can be commercially available and used as it is, or can be prepared from a corresponding dicarboxylic acid and hydroxylamine. In the general formula (21), Z represents a single bond, a double bond, a methylene group or an oxygen atom; T and Y each independently represent a hydrogen atom or a substituted or unsubstituted $C_1$-$C_{10}$ alkyl group or may form an aliphatic cyclic structure, an aromatic ring structure or a heterocyclic structure in combination thereof with carbon atoms to which T and Y are bonded. Specific examples of T and Y are those exemplified in the explanation of the general formula (18).

As the polymerizable isocyanate derivative of the general formula (15), there can be used those exemplified above in the explanation of Scheme (2).

The respective production steps will be explained below.

In the first step, there is no particular limitation on the amount of the N-hydroxydicarboxylmide of the general formula (21) reacted with the sulfonyl chloride of the general formula (20). The amount of the N-hydroxydicarboxylmide is generally 0.1 to 5 mol, preferably 0.2 to 3 mol, more preferably 0.5 to 2 mol, most preferably 0.8 to 1.5 mol, per 1 mol of the sulfonyl chloride.

The reaction can be performed in the absence of a solvent or in the presence of an inert solvent. There is no particular limitation on the kind of the solvent as long as the solvent is inert in the reaction. Preferred examples of such an inert solvent are: ketone solvents such as acetone, methyl ethyl ketone and methyl isobutyl ketone; ester solvents such as ethyl acetate and butyl acetate; ether solvents such as diethyl ether, diethylene glycol dimethyl ether, tetrahydrofuran and dioxane; halogenated solvents such as dichloromethane, chloroform, carbon tetrachloride, 1,2-dichloroethane, tetrachloroethylene, chlorobenzene and oxochlorobenzene; and polar solvents such as acetonitrile, N,N-dimethylformamide, N,N-dimethylimidazolidinone, dimethyl sulfoxide and sulfolane. These solvents can be used solely or in combination of two or more kinds thereof.

There is no particular limitation on the reaction temperature. The reaction temperature is generally −78 to 150° C., preferably −20 to 120° C., more preferably 0 to 100° C.

The reaction time is set depending on the reaction temperature and is generally several minutes to 100 hours, preferably 30 minutes to 50 hours, more preferably 1 to 20 hours. It is preferable to determine the time at which the sulfonyl chloride of the general formula (20) as the raw material has been consumed as the end of the reaction while monitoring the progress of the reaction by any analytical means such as nuclear magnetic resonance (NMR).

In general, the reaction is preformed with the use of a base catalyst. Preferred examples of the base catalyst are: organic bases such as trimethylamine, triethylamine, tripropylamine, tributylamine; and inorganic bases such as sodium hydroxide, potassium hydroxide, lithium hydroxide and sodium hydrogencarbonate. There is no particular limitation on the amount of the base catalyst used. The amount of the base catalyst used is generally 0.0001 to 10 mol, preferably 0.001 to 5 mol, more preferably 0.01 to 1.5 mol, per 1 mol of the sulfonyl chloride of the general formula (20).

After the reaction, the hydroxyfluoroalkane N-sulfonyloxyimide compound of the general formula (22) can be obtained by ordinary means such as extraction, crystallization or recrystallization and can be purified by recrystallization etc. as needed.

The second step will be next explained below.

In the second step, a urethane bond is formed by addition of the hydroxyfluoroalkane N-sulfonyloxyimide compound of the general foimula (22) to the polymerizable isocyanate derivative of the general formula (15). This addition reaction can be performed by reacting the hydroxyfluoroalkane N-sulfonyloxyimide compound of the general formula (22) with the polymerizable isocyanate derivative of the general formula (15) in the presence or absence of a catalyst.

There is no particular limitation on the amount of the polymerizable isocyanate derivative reacted with the hydroxyfluoroalkane N-sulfonyloxyimide compound of the general formula (22). The amount of the polymerizable isocyanate derivative is generally 0.1 to 5 mol, preferably 0.2 to 3 mol, more preferably 0.5 to 2 mol, most preferably 0.8 to 1.5 mol, per 1 mol of the hydroxyfluoroalkane N-sulfonyloxyimide compound.

The addition reaction can be performed in the presence or absence of a solvent. In general, it is preferable to perform the addition reaction with the use of an aprotic solvent. Examples of the aprotic solvent are diisopropyl ether, dichloroethane, chloroform, toluene, ethylbenzene, monochlorobenzene, acetonitrile and N,N-dimethylformamide. These solvents can be used solely or in combination of two or more kinds thereof. As the reaction is interfered with by the presence of water, it is preferable to dehydrate the solvent before use. In particular, the amount of water in the solvent is preferably 0.005 mass % or less, more preferably 0.002 mass % or less.

There is no particular limitation on the reaction temperature. The reaction temperature is generally 0 to 100° C., preferably 10 to 80° C. It is preferable to perform the reaction with stirring.

The reaction time is set depending on the reaction temperature and is generally several minutes to 100 hours, preferably 30 minutes to 50 hours, more preferably 1 to 20 hours. It is preferable to determine the time at which the polymerizable isocyanate derivative as the raw material has been consumed as the end of the reaction while monitoring the progress of the reaction by any analytical means such as nuclear magnetic resonance (NMR).

Although the reaction can be performed in the presence of no catalyst, the use of the catalyst leads to shortening of the reaction time and improvement of the reaction yield. Examples of the catalyst are: electron-donating amine compounds such as N,N-dimethyl-4-aminopyridine, 4-diethylaminopyridine, 4-aminopyridine, 2-aminopyridine, 2-hydroxypyridine, 2-methoxypyridine, 4-methoxypyridine, 4-hydroxypyridine, 2-dimethylaminoimidazole, 2-methoxyimidazole, 2-mercaptoimidazole, aminoquinoline, imidazole, 2-methylimidazole, 4-methylimidazole and diazabicyclooctane (DABCO); and organic tin compounds such as dibutyl tin dilaurate and dibutyl tin oxide. The amount of the catalyst used is generally 0.1 to 20 mol %, preferably 1 to 5 mol %, based on the N-sulfonyloxyimide compound.

After the reaction, the target polymerizable fluorine-containing N-sulfonyloxyimide compound of the general formula (18) can be obtained by removing the solvent under a reduced pressure.

Further, the polymerizable fluorine-containing N-sulfonyloxyimide compound of the general formula (18) can be purified by ordinary means such as extraction or recrystallization after the reaction.

[Fluorine-Containing Sulfonate Resin and Fluorine-Containing N-Sulfonyloxyimide Resin]

A resin having a repeating unit of the following general formula (3) (occasionally referred to as "fluorine-containing sulfonate resin" in the present specification) is formed by cleavage of a polymerizable double bond of the fluorine-containing sulfonate of the general formula (1-1). In the polymerization reaction, the original structure of any part of the fluorine-containing sulfonate, other than the polymerizable double bond, can be maintained with no structural changes.

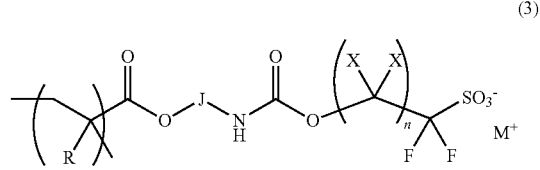

(3)

In the general formula (3), X, n, R and J have the same definitions as in the general formula (1); and $M^+$ represents a monovalent cation.

It is preferable to use the onium cation $Q^+$ as the cation $M^+$. In this case, a resin having a repeating unit of the following general formula (4) is formed by cleavage of a polymerizable double bond of the polymerizable fluorine-containing sulfonic acid onium salt of the general formula (2).

(4)

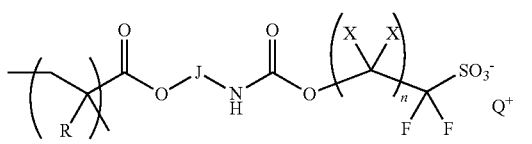

In the general formula (4), X, n, R and J have the same definitions as in the general formula (1); and $Q^+$ has the same definition as in the general formula (2).

On the other hand, a resin having a repeating unit of the following general formula (17) (occasionally referred to as "fluorine-containing N-sulfonyloxyimide resin" in the present specification) is formed by cleavage of a polymerizable double bond of the polymerizable fluorine-containing N-sulfonyloxyimide compound of the general formula (18). In the polymerization reaction, the original structure of any part of the fluorine-containing N-sulfonyloxyimide compound, other than the polymerizable double bond, can be maintained with no structural changes.

(17)

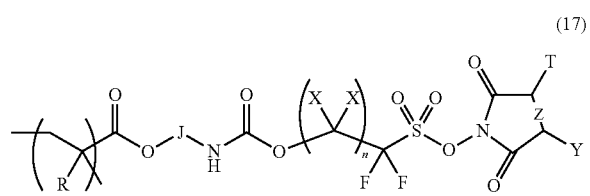

In the general formula (17), X, n, R and J have the same definitions as in the general formula (1); Z represents a single bond, a double bond, a methylene group or an oxygen atom; T and Y each independently represent a hydrogen atom or a substituted or unsubstituted $C_1$-$C_{10}$ alkyl group or may form an aliphatic cyclic structure, an aromatic ring structure or a heterocyclic structure in combination thereof with carbon atoms to which T and Y are bonded.

The resin having the repeating unit of the general formula (4) or (17) is converted to the resin having the repeating unit of the following general formula (5) by exposure to high energy radiation.

(5)

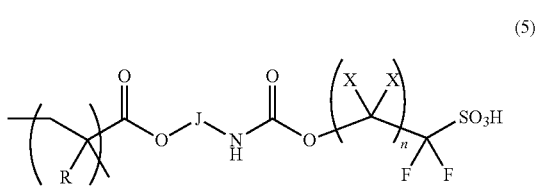

In the general formula (5), X, n, R and J have the same definitions as in the general formula (1).

There is no particular limitation on the high energy radiation. It is effective to use high energy radiation of 300 nm or less wavelength, such as near-ultraviolet radiation (wavelength: 380 to 200 nm), far-ultraviolet radiation (VUV, wavelength: 200 to 10 nm), extreme-ultraviolet radiation (EUV, wavelength: 10 nm or less), soft X-ray, X-ray or γ-ray generated by excimer laser e.g. KrF excimer laser, ArF excimer laser or $F_2$ excimer laser or by synchrotron radiation, in the case of using the resin for fine patterning.

After the elimination of the cation $Q^+$ of the general formula (4) or the dicarboxylmide group of the general formula (17), the repeating unit has a difluorosulfonic acid at an end thereof that shows high acidity and functions as a photoacid generator for a chemically amplified resist composition. A composition containing the resin (fluorine-containing sulfonate resin) having at least the repeating unit of the general formula (4) or the resin (fluorine-containing N-sulfonyloxyimide resin) having at least the repeating unit of the general formula (17) in addition to a base resin and a solvent can be thus suitably used as a resist composition.

Depending on the purpose of use of the fluorine-containing sulfonate resin, the fluorine-containing sulfonate resin has the repeating unit of the general formula (4) in combination with or without a repeating unit containing an acid labile group or a cross-linking site. In either case, the fluorine-containing sulfonate resin may have any other repeating unit (referred to as "auxiliary repeating unit" in the present specification). The term "auxiliary repeating unit" means a repeating unit that does not correspond to the repeating unit of the general formula (4) and does not correspond to the repeating unit containing the acid labile group or cross-linking site. The term "auxiliary monomer" means a monomer capable of foaming an auxiliary repeating unit by cleavage of a polymerizable double bond thereof.

Similarly, the fluorine-containing N-sulfonyloxyimide resin consists of the repeating unit of the general formula (17) in combination with or without a repeating unit containing an acid labile group or a cross-linking site depending on the purpose of use of the fluorine-containing N-sulfonyloxyimide resin. In either case, the fluorine-containing N-sulfonyloxyimide resin may have any other repeating unit (referred to as "auxiliary repeating unit" in the present specification). The term "auxiliary repeating unit" means a repeating unit that does not correspond to the repeating unit of the general formula (17) and does not correspond to the repeating unit containing the acid labile group or cross-linking site. The term "auxiliary monomer" means a monomer capable of forming an auxiliary repeating unit by cleavage of a polymerizable double bond thereof.

In other words, the fluorine-containing sulfonate resin can be in the form of a homopolymer consisting of the repeating unit of the general formula (4) as obtained by homopolymerization of the polymerizable fluorine-containing sulfonic acid onium salt of the general formula (2) or in the form of a copolymer having the auxiliary repeating unit in addition to the repeating unit of the general formula (4). The fluorine-containing N-sulfonyloxyimide resin can be in the form of a homopolymer consisting of the repeating unit of the general formula (17) as obtained by homopolymerization of the fluorine-containing N-sulfonyloxyimide compound of the general formula (18) or in the form of a copolymer having the auxiliary repeating unit in addition to the repeating unit of the general formula (17). In these cases, the fluorine-containing sulfonate resin and the fluorine-containing N-sulfonyloxyimide resin themselves cannot be used as a positive or negative resist resin but can be used as a photoacid generator to form a resist composition with a base resin. For such use, the fluorine-containing sulfonate resin contains 0.1 to 100 mol %, preferably 1 to 100 mol %, more preferably 2 to 100 mol %, of the repeating unit of the general formula (4); and the fluorine-containing N-sulfonyloxyimide resin contains 0.1 to 100 mol %, preferably 1 to 100 mol %, more preferably 2 to 100 mol %, of the repeating unit of the general formula (17). In each of the fluorine-containing sulfonate resin and the fluorine-containing N-sulfonyloxyimide resin, the balance is the auxiliary repeating unit. If the amount of the repeating unit of the general formula (4) or (17) is less than 0.1 mol %, it is unfavorably necessary to use a large amount of another photoacid generator in the resist composition in order for the resist composition to maintain sufficient photosensitivity to high energy radiation.

Alternatively, the fluorine-containing sulfonate resin can consist of the repeating unit of the general formula (4) and the repeating unit containing the acid labile group or cross-linking site. In this case, the fluorine-containing sulfonate resin contains 0.1 to 90 mol %, preferably 0.5 to 50 mol %, more preferably 1 to 30 mol %, of the repeating unit of the general formula (4), with the balance being the repeating unit containing the acid labile group or cross-linking site. The fluorine-containing N-sulfonyloxyimide resin can also alternatively consist of the repeating unit of the general formula (17) and the repeating unit containing the acid labile group or cross-linking group. In this case, the fluorine-containing N-sulfonyloxyimide resin contains 0.1 to 90 mol %, preferably 0.5 to 50 mol %, more preferably 1 to 30 mol % of the repeating unit of the general formula (17), with the balance being the repeating unit containing the acid labile group or cross-linking site. If the amount of the repeating unit of the general formula (4) or (17) is less than 0.1 mol %, the fluorine-containing sulfonate resin or fluorine-containing N-sulfonyloxyimide resin does not show sufficient photosensitivity as the photoacid generator so that it is unfavorably necessary to use another photoacid generator and is not possible to make sufficient use of the high performance of the resin. If the amount of the repeating unit of the general formula (4) or (17) exceeds 90 mol %, the fluorine-containing sulfonate resin or fluorine-containing N-sulfonyloxyimide resin can adequately function as the photoacid generator. It is not however possible to take advantage of adding the repeating unit containing the acid labile group or cross-linking site in the resin. In the case where the fluorine-containing sulfonate resin or fluorine-containing N-sulfonyloxyimide resin has the repeating unit containing the acid labile group or cross-linking site, the repeating unit of the general formula (4) or (17) and the auxiliary repeating unit, the fluorine-containing sulfonate resin or fluorine-containing N-sulfonyloxyimide resin contains 0.1 to 70 mol %, preferably 1 to 60 mol %, more preferably 10 to 50 mol %, of the auxiliary repeating unit, with the balance being the repeating unit containing the acid labile group or cross-linking site and the repeating unit of the general formula (4) or (17).

If the amount of the auxiliary repeating unit is less than 0.1 mol %, it is unfavorably difficult to control the substrate adhesion and etching resistance of the resist resin. If the amount of the auxiliary repeating unit exceeds 70 mol %, it is unfavorably difficult to make sufficient use of the function of the fluorine-containing sulfonate resin or fluorine-containing N-sulfonyloxyimide resin as the photoacid generator or the positive or negative resist resin in the present invention.

More specifically, the fluorine-containing sulfonate resin contains 1 to 60 mol % of the repeating unit of the general formula (4) and 10 to 85 mol % of the repeating unit containing the acid labile group or cross-linking site, with the balance being the auxiliary repeating unit, when the fluorine-containing sulfonate resin functions not only as the photoacid generator but as the positive or negative resist resin. It is preferable that the fluorine-containing sulfonate resin contains 2 to 40 mol % of the repeating unit of the general formula (4) and 10 to 70% of the repeating unit containing the acid labile group or cross-linking site, more preferably 4 to 30 mol % of the repeating unit of the general formula (4) and 15 to 60% of the repeating unit containing the acid labile group or cross-linking site, with the balance being the auxiliary repeating unit. The composition of the fluorine-containing sulfonate resin is not however limited to the above range as mentioned above. Similarly, the fluorine-containing N-sulfonyloxyimide resin contains 1 to 60 mol % of the repeating unit of the general formula (17) and 10 to 85 mol % of the repeating unit containing the acid labile group or cross-linking site, with the balance being the auxiliary repeating unit, when the fluorine-containing N-sulfonyloxyimide resin functions not only as the photoacid generator but as the positive or negative resist resin. It is preferable that the fluorine-containing N-sulfonyloxyimide resin contains 2 to 40 mol % of the repeating unit of the general formula (17) and 10 to 70% of the repeating unit containing the acid labile group or cross-linking site, more preferably 4 to 30 mol % of the repeating unit of the general formula (17) and 15 to 60% of the repeating unit containing the acid labile group or cross-linking site, with the balance being the auxiliary repeating unit. The composition of the fluorine-containing N-sulfonyloxyimide resin is not however limited to the above range as mentioned above.

In the present invention, the fluorine-containing sulfonate resin or fluorine-containing N-sulfonyloxyimide resin generally has a mass-average molecular weight of 1,000 to 1,000,000, preferably 2,000 to 500,000, as measured by gel permeation chromatography (GPC) in the case where the fluorine-containing sulfonate resin or fluorine-containing N-sulfonyloxyimide resin also functions as the base resin. In the case of using any base resin in combination with the fluorine-containing sulfonate resin or the fluorine-containing N-sulfonyloxyimide resin for preparation of the resist composition, the fluorine-containing sulfonate resin or fluorine-containing N-sulfonyloxyimide resin generally has a mass-average molecular weight of 1,000 to 100,000, preferably 2,000 to 50,000. If the mass-average molecular weight of the fluorine-containing sulfonate resin or fluorine-containing N-sulfonyloxyimide resin is less than 1,000, the fluorine-containing sulfonate resin or fluorine-containing N-sulfonyloxyimide resin may diffuse and migrate in the resulting resist film and reach the unexposed portion of the resist film during heat treatment after pattern exposure. This leads to deterioration in pattern resolution so that the effect of use of the fluorine-containing sulfonate resin or fluorine-containing N-sulfonyloxyimide resin becomes low. If the mass-average molecular weight of the fluorine-containing sulfonate resin or fluorine-containing N-sulfonyloxyimide resin exceeds 1,000,000, the solubility of the resin in the solvent may become lowered so that it is unfavorably difficult to form a smooth resist film. The molecular weight distribution (Mw/Mn) of the fluorine-containing sulfonate resin or fluorine-containing N-sulfonyloxyimide resin is preferably in the range of 1.01 to 5.00, more preferably 1.01 to 4.00, still more preferably 1.01 to 3.00, most preferably 1.10 to 2.50.

As mentioned above, each of the fluorine-containing sulfonate resin and the fluorine-containing N-sulfonyloxyimide resin can be in the form of a homopolymer or in the form of a copolymer with the other monomer in the present invention. When the acid labile group-containing monomer is used as the other monomer, the fluorine-containing sulfonate resin or fluorine-containing N-sulfonyloxyimide resin attains a photosensitive solubility-changing function for use in a positive resist composition. When the cross-linking site-containing monomer is used as the other monomer, the fluorine-containing sulfonate resin or fluorine-containing N-sulfonyloxyimide resin attains a photosensitive solubility-changing function for use in a negative resist composition. The copolymerization monomer used is not limited to the acid labile group-containing monomer or the cross-linking site-containing monomer. Various kinds of auxiliary monomers can be copolymerized in the fluorine-containing sulfonate resin or fluorine-containing N-sulfonyloxyimide resin for control of dry etching resistance, standard developer compatibility, substrate adhesion, resist profile and other generally required resist characteristics such as resolution, heat resistance and sensitivity.

[Repeating Unit with Positive/Negative Photosensitive Solubility-Changing Function]

The fluorine-containing sulfonate resin or fluorine-containing N-sulfonyloxyimide resin having the repeating unit with the positive or negative photosensitive solubility-changing function can be obtained by copolymerization of any monomer having a positive or negative photosensitive solubility-changing function with the polymerizable fluorine-containing sulfonic acid onium salt of the general formula (2) or the polymerizable fluorine-containing N-sulfonyloxyimide compound of the general formula (18).

In the case where the fluorine-containing sulfonate resin or fluorine-containing N-sulfonyloxyimide resin performs its photosensitive solubility-changing function as a positive resist resin, the fluorine-containing sulfonate resin or fluorine-containing N-sulfonyloxyimide resin has a leaving site such as a carboxyl or hydroxyl group protected by an acid labile group on a side chain thereof and has a main chain structure of repeating unit formed by cleavage of a polymerizable double bond group such as vinyl group, 1-methylvinyl group, 1-fluorovinyl group, 1-trifluoromethylvinyl group, 1-cyanovinyl group or norbornenyl group. The leaving site is bonded to the main chain via a linking group W. In this case, the linking group W refers to a linking group W' capable of providing a link as represented by (main chain) —W$^1$—O— (acid labile group) or (main chain) —W$^1$—C(=O)— (acid labile group) where the main chain structure is denoted as "main chain"; and the acid labile group in the leaving site is denoted as "acid labile group". The acid labile group refers to a group capable of leaving from the resin so as to serve as an acid by the action of an acid generated from the photoacid generator etc. and thereby increase the dissolution rate of the acid labile group-containing resin into an alkaline developer. The moiety containing such an acid labile group e.g. ester moiety (—C(=O)OR', alkoxycarbonyl group) or ether moiety (—O—R', alkoxy group) (where R' represents an acid labile group) is occasionally called "acid-decomposable site" or "leaving site".

In the case where the fluorine-containing sulfonate resin or fluorine-containing N-sulfonyloxyimide resin performs its photosensitive solubility-changing function as a negative resist resin, the fluorine-containing sulfonate resin or fluorine-containing N-sulfonyloxyimide resin has a cross-linking site such as a hydroxy or carboxyl group on a side chain thereof and has a main chain structure of repeating unit formed by cleavage of a polymerizable double bond group such as vinyl group, 1-methylvinyl group, 1-fluorovinyl group, 1-trifluoromethylvinyl group, 1-cyanovinyl group or norbornenyl group. The cross-linking site is bonded to the main chain via a linking group W. In this case, the linking group W refers to a linking group W$^2$ capable of providing a link as represented by (main chain) —W$^2$—(OH) or (main chain) —W$^2$—C(=O)—(OH) where the main chain structure is denoted as "main chain"; and the OH group in the cross-linking site is denoted as "OH". The hydroxyl group refers to a substantially neutral alcoholic hydroxyl group that is not generally involved in the dissolution of the resin into an alkaline solution but is cross-linked with the after-mentioned cross-linking agent by hydroxyl-related reaction e.g. ester bonding, ether bonding, ureide bonding etc. so as to make the alkali-soluble resin component insoluble in an alkali solution.

Next, the linking groups W, W$^1$ and W$^2$ will be described below.

The linking group W, W$^1$, for linking the leaving moiety to the main chain of the repeating unit in the positive resist resin, is a divalent linking group formed by one kind, or two or more kinds in combination, selected from the group consisting of a single bond, (CR$^{21}$R$^{22}$)$_n$— (where n is an integer of 1 to 10), —O—, —C(=O)—, —C(=O)O— or —O—C(=O)—, a divalent alicyclic hydrocarbon group, a divalent aromatic hydrocarbon group, a divalent heterocyclic group, a thioether group, an ester group, an amide group, a sulfonamide group, an urethane group and an urea group.

The linking group W$^2$, for linking the leaving moiety to the main chain of the repeating unit in the negative resist resin, is the same as the linking group W$^1$ except for not including any divalent aromatic hydrocarbon group and aromatic heterocyclic group.

The combined linking group W' can be exemplified by:
—(CR$^{21}$R$^{22}$)$_m$—C(=O)—O—(CR$^{21}$R$^{22}$)$_n$—;
—(CR$^{21}$R$^{22}$)$_m$—C(=O)—O—(CR$^{21}$R$^{22}$)$_n$—B—(CR$^{21}$R$^{22}$)$_l$—;
—(CR$^{21}$R$^{22}$)$_m$—O—(CR$^{21}$R$^{22}$)$_n$—;
—(CR$^{21}$R$^{22}$)$_m$—O—(CR$^{21}$R$^{22}$)$_n$—B—(CRR$^{21}$R$^{22}$)$_l$—;
—(CR$^{21}$R$^{22}$)$_n$—B—(CR$^{21}$R$^{22}$)$_l$—C(=O)—O—(CR$^{21}$R$^{22}$)$_m$—; and
—(CR$^{21}$R$^{22}$)$_n$—B—(CR$^{21}$R$^{22}$)$_l$—O—(CR$^{21}$R$^{22}$)$_m$—,
where B represents a cyclic group selected from a divalent alicyclic hydrocarbon group, a divalent aromatic hydrocarbon group or a divalent heterocyclic group; and l, m and n each independently represent an integer of 0 to 10. It is preferable that m is 0 and each of l and n is 0 or 1.

The combined linking group W$^2$ can be exemplified by:
—(CR$^{21}$R$^{22}$)$_m$—C(=O)—O—(CR$^{21}$R$^{22}$)$_n$—;
—(CR$^{21}$R$^{22}$)$_m$—C(=O)—O—(CR$^{21}$R$^{22}$)$_n$—B'—(CR$^{21}$R$^{22}$)$_l$—;
—(CR$^{21}$R$^{22}$)$_m$—O—(CR$^{21}$R$^{22}$)$_n$—;
—(CR$^{21}$R$^{22}$)$_m$—O—(CR$^{21}$R$^{22}$)$_n$—B'—(CR$^{21}$R$^{22}$)$_l$—;
—(CR$^{21}$R$^{22}$)$_n$—B'—(CR$^{21}$R$^{22}$)$_l$—C(=O)—O—(CR$^{21}$R$^{22}$)$_m$—; and
—(CR$^{21}$R$^{22}$)$_n$—B—(CR$^{21}$R$^{22}$)$_l$—O—(CRR$^{21}$R$^{22}$)$_m$—,
where B' represents a cyclic group selected from a divalent alicyclic group or a divalent heterocyclic group; and l, m and n each independently represent an integer of 0 to 10. It is preferable that m is 0 and each of l and n is 0 or 1.

The substituted or unsubstituted methylene group represented by —(CR$^{21}$R$^{22}$)— is the same in definition as that of the linking group J as represented by the general formula (13) and thus will not be herein repeatedly explained. Further, R$^{21}$ and R$^{22}$ can be read as R$^{13}$ and R$^{14}$ and will not be repeatedly explained.

The cyclic group B is the same in definition as the divalent alicyclic hydrocarbon group, divalent aromatic hydrocarbon group or divalent heterocyclic group of the linking group J and thus will not be repeatedly explained.

The cyclic group B' is also the same in definition as the divalent alicyclic hydrocarbon group or divalent heterocyclic group of the linking unit J and thus will not be repeatedly explained.

Specific examples of the linking group W$^1$ are as follows:
(single bond);
—CH$_2$—;
—CH$_2$—CH$_2$—;
—CH$_2$—B—;
—B—CH$_2$—;
—C$_6$H$_4$—;
—C(=O)—O—CH$_2$—;
—C(=O)—O—CH$_2$—CH$_2$;

—C(=O)—O—B—;
—CH$_2$—C(=O)—O—CH$_2$—;
—O—CH$_2$—;
—O—CH$_2$—CH$_2$—;
—O—B—;
—CH$_2$—O—CH$_2$—; and
—C(=O)—O—(CR$^{21}$R$^{22}$)$_2$—; or
C$_6$H$_4$—O—(CR$^{21}$R$^{22}$)$_2$—.

It is herein preferable that R$^{21}$ and R$^{22}$ are each independently a hydrogen atom, a fluorine atom, an alkyl group, a substituted alkyl group or an alicyclic hydrocarbon group. One or more hydrogen atoms of the above linking group may be substituted with a fluorine atom. Among others, particularly preferred are —C(=O)—O—CH$_2$—, —C$_6$H$_4$— and —C(=O)—O—(CR$^{21}$R$^{22}$)$_2$— where R$^{21}$ and R$^{22}$ are each independently a hydrogen atom, a fluorine atom, a lower alkyl group or a fluorine-containing lower alkyl group.

Specific examples of the linking group W$^2$ are as follows:
—(single bond);
—CH$_2$—;
—CH$_2$—CH$_2$—;
—CH$_2$—B'—;
—B'—;
—B'—CH$_2$—;
—C(=O)—O—CH$_2$—;
—C(=O)—O—CH$_2$—CH$_2$—;
—C(=O)—O—B'—;
—CH$_2$—C(=O)—O—CH$_2$—;
—O—CH$_2$;
—O—CH$_2$—CH$_2$—;
—O—B'—; and
—CH$_2$—O—CH$_2$—; or
—C(=O)—O—(CR$^{21}$R$^{22}$)$_2$—.

It is herein also preferable that R$^{21}$ and R$^{22}$ are each independently a hydrogen atom, a fluorine atom, an alkyl group, a substituted alkyl group or an alicyclic hydrocarbon group. One or more hydrogen atoms of the above linking group may be substituted with a fluorine atom. Among others, particularly preferred are —C(=O)—O—, —C(=O)—O—CH$_2$—, —C(=O)—O—B'— and —C(=O)—O—(CR$^{21}$R$^{22}$)$_2$— where R$^{21}$ and R$^{22}$ are each independently a hydrogen atom, a fluorine atom, a lower alkyl group or a fluorine-containing lower alkyl group.

There can also be used a repeating unit of the following general formula (12), which has an acid labile group represented by R$^{12}$ and a main chain moiety represented by —(CH$_2$—C(R$^1$))—.

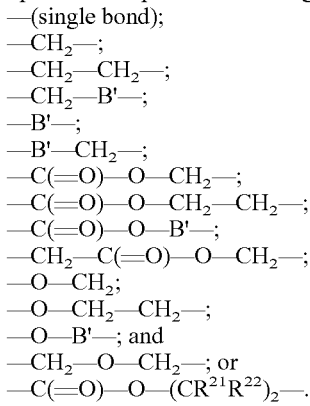
(12)

In the general formula (12), R$^1$ represents a hydrogen atom, a halogen atom or a C$_1$-C$_3$ alkyl or fluorine-containing alkyl group; R$^{10}$ represents a hydrogen atom, a fluorine atom or a fluorine-containing alkyl group; R$^{12}$ preferably represents either one of acid labile groups of the following general formulas (d) to (h); and R$^9$ represents a divalent linking group.

As —R$^9$—(CR$^{10}$F)— corresponds to W$^1$, the above explanations of the linking group W$^1$ can be applied to the corresponding moiety —R$^9$—(CR$^{10}$F)—.

[Acid Labile Group]

The acid labile group is either one of acid labile groups of the following general formulas (d) to (h) in the photosensitive solubility-changeable fluorine-containing sulfonate resin or fluorine-containing N-sulfonyloxyimide resin according to the present invention.

$$R^{X1}—O—C(=O)— \quad (d)$$

In the general formula (d), R$^{X1}$ represents a C$_1$-C$_4$ alkyl group that may have a substituent, a C$_3$-C$_{30}$ alicyclic hydrocarbon group that may have a substituent, or a C$_6$-C$_{14}$ aryl group that may have a substituent.

$$R^{X1}—O—CHR^{X2}— \quad (e)$$

In the general formula (e), R$^{X1}$ has the same definition as in the general formula (d); and R$^{X2}$ represents a hydrogen atom, a C$_1$-C$_4$ alkyl group that may have a substituent, a C$_3$-C$_{30}$ alicyclic hydrocarbon group that may have a substituent, a C$_1$-C$_6$ alkoxy group that may have a substituent, a C$_2$-C$_4$ alkenyl group that may have a substituent, a C$_6$-C$_{14}$ aryl group that may have a substituent, or a C$_7$-C$_{20}$ aralkyl group that may have a substituent.

$$CR^{X3}R^{X4}R^{X5}— \quad (f)$$

In the general formula (f), R$^{X3}$, R$^{X4}$ and R$^{X5}$ may be the same or different and each represent a C$_1$-C$_4$ alkyl group that may have a substituent, a C$_3$-C$_{30}$ alicyclic hydrocarbon group that may have a substituent, a C$_2$-C$_4$ alkenyl group that may have a substituent, a C$_6$-C$_{14}$ aryl group that may have a substituent, or a C$_7$-C$_{20}$ aralkyl group that may have a substituent; and two of R$^{X3}$, R$^{X4}$ and R$^{X5}$ may be bonded together to form a ring.

$$SiR^{X3}R^{X4}R^{X5}— \quad (g)$$

In the general formula (g), R$^{X3}$, R$^{X4}$ and R$^{X5}$ have the same definitions as in the general formula (f).

$$R^{X1}—C(=O)— \quad (h)$$

In the general formula (h), R$^{X1}$ has the same definition as in the general formula (d).

The monovalent organic groups R$^{X1}$, R$^{X2}$, R$^{X3}$, R$^{X4}$ and R$^{X5}$ in the above genera formulas (d) to (h) will be explained in more detail below. It is herein preferable to use the acid labile group of the general formula (d), (e) or (f) in the resist composition for pattern formation by exposure to high energy radiation as the acid labile group of the general formula (d), (e) or (f) has a chemical amplification function.

As mentioned above, R$^{X1}$ represents an alkyl group, an alicyclic hydrocarbon group or an aryl group; R$^{X2}$ represents a hydrogen atom, an alkyl group, an alicyclic hydrocarbon group, an alkenyl group, an aralkyl group, an alkoxy group or an aryl group; R$^{X3}$, R$^{X4}$ and R$^{X5}$ may be the same or different and each represent an alkyl group, an alicyclic hydrocarbon group, an alkenyl group, an aralkyl group or an aryl group; and two of two of R$^{X3}$, R$^{X4}$ and R$^{X5}$ may be bonded together to form a ring.

Preferred examples of the alkyl group are those of 1 to 4 carbon atoms, such as methyl, ethyl, propyl, isopropyl, n-butyl, sec-butyl and tert-butyl. Preferred examples of the alicyclic hydrocarbon group are those of 3 to 30 carbon atoms, such as cyclopropyl, cyclopentyl, cyclohexyl, adamantyl, norbornyl, bornyl, tricyclodecanyl, dicyclopentenyl, epoxynorbornan, menthyl, isomenthyl, neomenthyl, tetracyclododecanyl and steroid residue. Preferred examples of the alkenyl group are those of 2 to 4 carbon atoms, such as vinyl, propenyl, allyl and butenyl. Preferred examples of the aryl group are those of 6 to 14 carbon atoms, such as phenyl, xylyl, toluoyl, cumenyl, naphthyl and anthracenyl. These groups may have substituents. Preferred examples of the aralkyl group are those of 7 to 20 carbon atoms, such as benzyl, phenethyl and cumyl, each of which may have a substituent.

As the substituents of the alkyl group, the alicyclic hydrocarbon group, the alkenyl group, the aryl group and the aralkyl group, there can be used: a hydroxy group; a halogen atom (fluorine, chlorine, bromine, iodine); a nitro group; a cyano group; any of the above alkyl and alicyclic hydrocarbon groups; an alkoxy group such as methoxy, ethoxy, hydroxyethoxy, propoxy, hydroxypropoxy, n-butoxy, isobutoxy, sec-butoxy or tert-butoxy; an alkoxycarbonyl group such as methoxycarbonyl or ethoxycarbonyl; an aralkyl group such as benzyl, phenethyl or cumyl; an aralkyloxy group; an acyl group such as formyl, acetyl, butyryl, benzoyl, cinnamyl or valeryl; an acyloxy group such as butyryloxy; any of the above alkenyl groups; an alkenyloxy group such as vinyloxy, propenyloxy, allyloxy or butenyloxy; any of the above aryl groups, an aryloxy group such as phenoxy; and an aryloxycarbonyl group such as benzoyloxy.

There can also be used lactone groups of the following formulas (3-1) and (3-2).

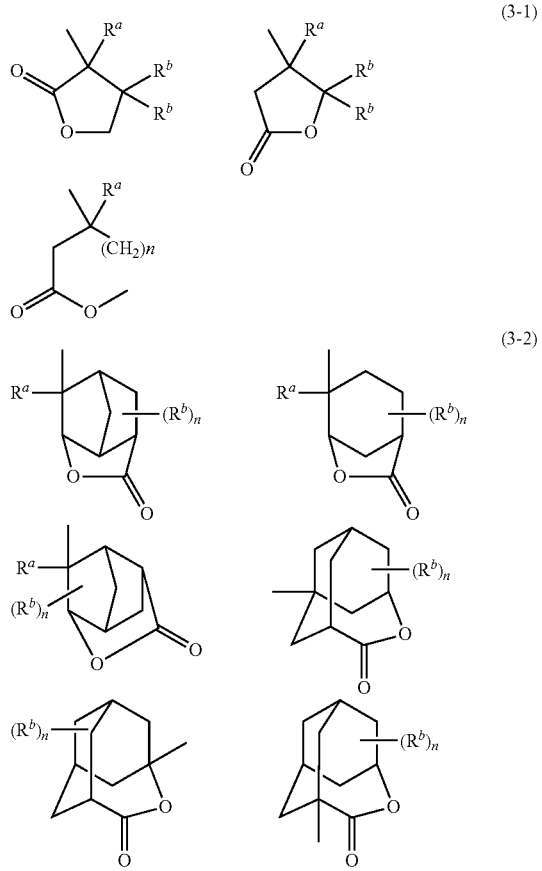

In the formulas (3-1) and (3-2), $R^a$ represents a $C_1$-$C_4$ alkyl or perfluoroalkyl group; $R^b$ each independently represent a hydrogen atom, a $C_1$-$C_4$ alkyl or perfluoroalkyl group, a hydroxy group, a carboxylic acid group, an alkyloxycarbonyl group, an alkoxy group or the like; and n represents an integer of 1 to 4.

The acid labile group is more specifically exemplified as follows.

Specific examples of the alkoxycarbonyl group represented by the general formula (d): $R^{X1}$—O—C(=O)— are tert-butoxycarbonyl, tert-amyloxycarbonyl, methoxycarbonyl, ethoxycarbonyl, i-propoxycarbonyl, cyclohexyloxycarbonyl, isobornyloxycarbonyl and adarnantanoxycarbonyl.

Specific examples of the acetal group represented by the general formula (e): $R^{X1}$—O—$CHR^{X2}$— are methoxymethyl, ethoxymethyl, 1-ethoxyethyl, 1-butoxyethyl, 1-isobutoxyethyl, 1-cyclohexyloxyethyl, 1-benzyloxyethyl, 1-phenethyloxyethyl, 1-ethoxypropyl, 1-benzyloxypropyl, 1-phenethyloxypropyl, 1-ethoxybutyl, 1-cyclohexyoxyethyl, 1-ethoxyisobutyl, 1-methoxyethoxymethyl, tetrahydropyranyl and tetrahydrofuranyl. There can also be used acetal groups obtained by addition of vinyl ethers to a hydroxy group.

Specific examples of the tertiary hydrocarbon group represented by the general formula: $CR^{X3}R^{X4}R^{X5}$— are tert-butyl, tert-amyl, 1,1-dimethylpropyl, 1-ethyl-1-methylpropyl, 1,1-dimethylbutyl, 1-ethyl-1-methylbutyl, 1,1-diethylpropyl, 1,1-dimethyl-1-phenylmethyl, 1-methyl-1-ethyl-1-phenylmethyl, 1,1-diethyl-1-phenylmethyl, 1-methylcyclohexyl, 1-ethylcyclohexyl, 1-methylcyclopentyl, 1-ethylcyclopentyl, 1-isobornyl, 1-methyladamantyl, 1-ethyladamantyl, 1-isopropyladamantyl, 1-isopropylnorbornyl and 1-isopropyl-(4-methylcyclohexyl).

The alicyclic hydrocarbon group or the alicyclic hydrocarbon-containing acid labile group can be exemplified by the following formulas (4-1) and (4-2).

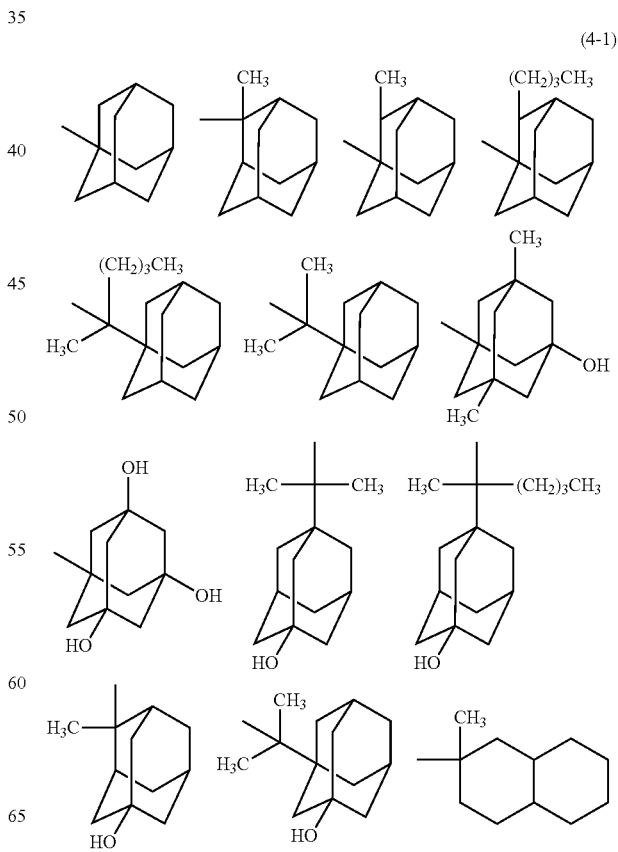

(4-1)

-continued

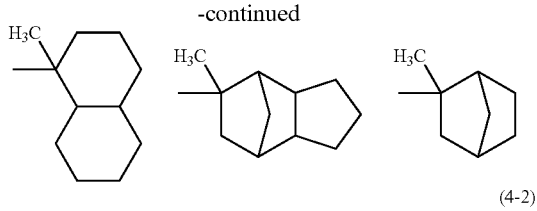

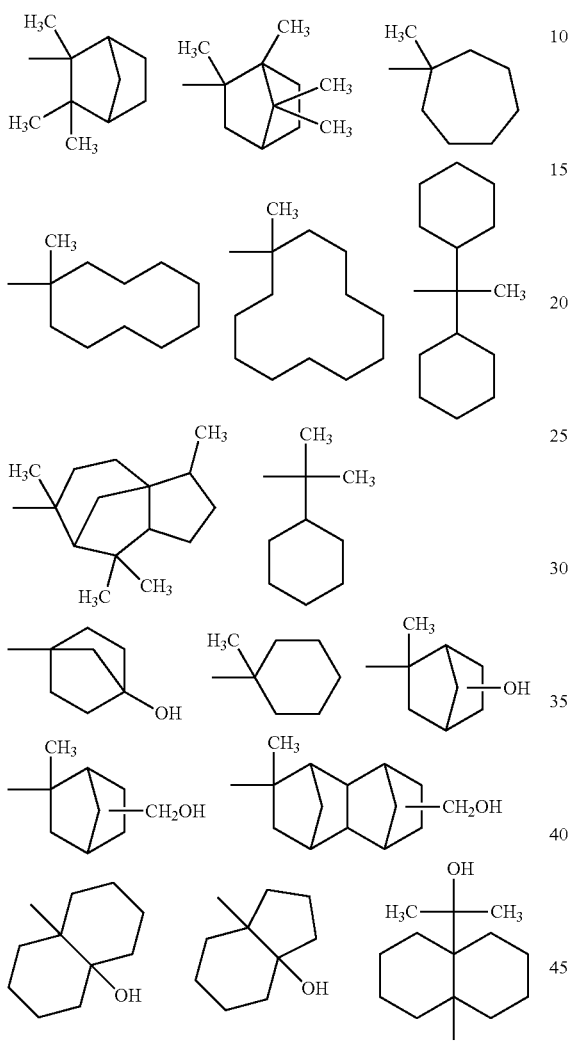

(4-2)

In the formulas (4-1) and (4-2), methyl (CH₃) group may independently be replaced by ethyl group; and one or two or more of the ring carbons may have a substituent group as mentioned above.

Specific examples of the silyl group represented by the general formula (g): $SiR^{X3}R^{X4}R^{X5}$— are trimethylsilyl, ethyldimethylsilyl, methyldiethylsilyl, triethylsilyl, i-propyldimethylsilyl, methyl-di-i-propylsilyl, tri-i-propylsilyl, tert-butyldimethylsilyl, methyl-di-tert-butylsilyl, tri-tert-butylsilyl, phenyldimethylsilyl, methyldiphenylsilyl and triphenylsilyl.

Specific examples of the acyl group represented by the general formula (h): $R^{X1}$—C(=O)— are acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophtaloyl, terephthaloyl, naphthoyl, toluoyl, hydroatropoyl, atropoyl, cinnamoyl, furoyl, thenoyl, nicotinoyl and isonicotinoyl. There can also be used those obtained by substitution of a part or all of hydrogen atoms of the above acid labile groups with a fluorine atom.

Further, the lactone-containing acid-labile protecting group can be exemplified by the following formulas (5), (6) and (7).

(5)

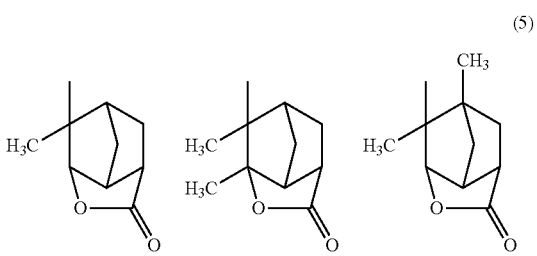

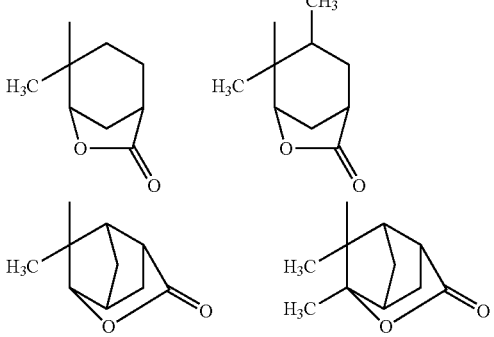

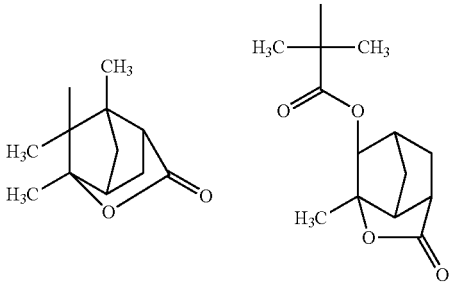

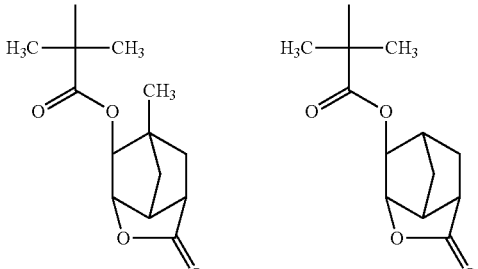

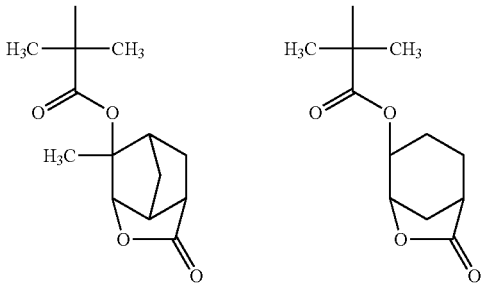

-continued

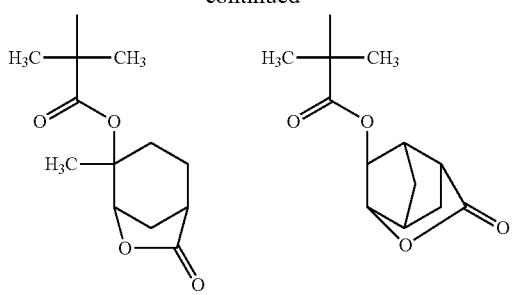

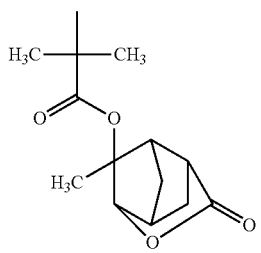

(6)

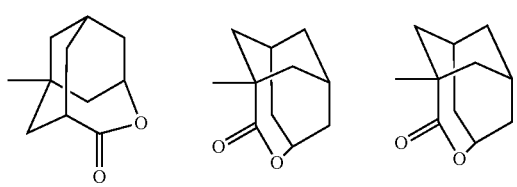

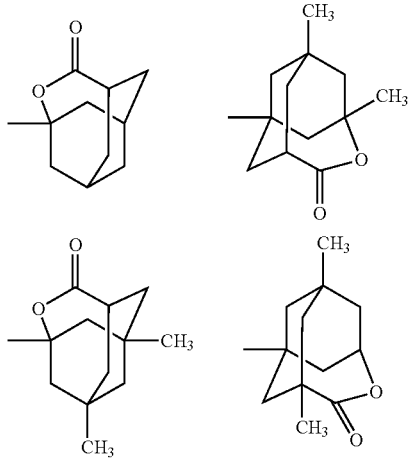

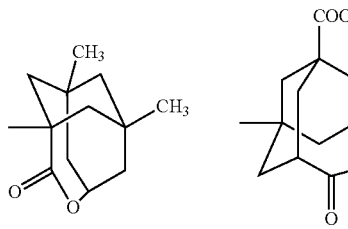

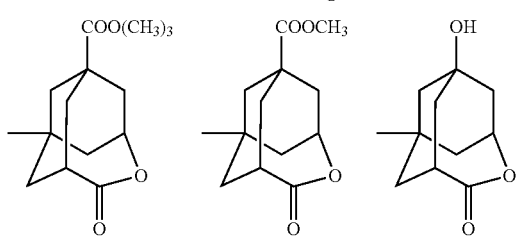

-continued

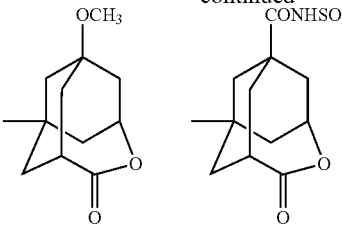

(7)

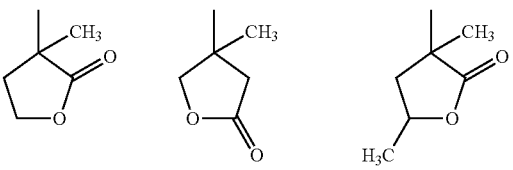

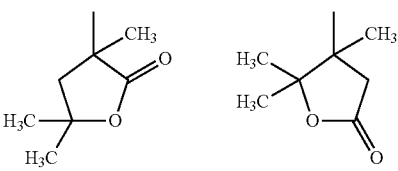

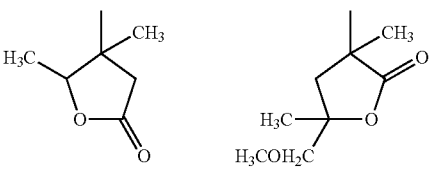

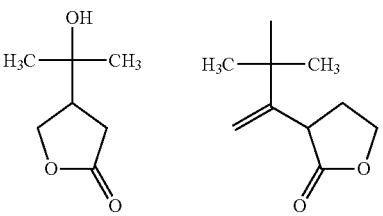

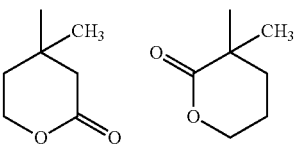

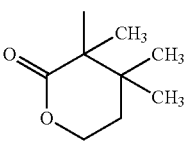

In the formulas (5), (6) and (7), methyl ($CH_3$) group may independently be replaced by ethyl group.

In the case of using ArF excimer laser as the exposure light source, the acid labile group is preferably a tertiary alkyl group such as tert-butyl or tert-amyl, an alkoxyethyl group such as 1-ethoxyethyl, 1-butoxyethyl, 1-isobutoxyethyl or 1-cyclohexyloxyethyl, an alkoxymethyl group such as methoxymethyl or ethoxymethyl, an acid labile group containing an alicyclic hydrocarbon such as adamantyl or isobornyl, or a lactone-containing acid labile group as exemplified above.

[Other Copolymerization Component (Auxiliary Repeating Unit)]

The fluorine-containing sulfonate resin or fluorine-containing N-sulfonyloxyimide resin according to the present invention can be produced with the use of an auxiliary monomer as a copolymerization component. The auxiliary monomer is one or more kinds selected from the after-mentioned monomers. In the present invention, the fluorine-containing sulfonate resin or fluorine-containing N-sulfonyoxyimide resin has an auxiliary repeating unit formed by cleavage of a polymerizable double bond of the auxiliary monomer. There is no particular limitation on the auxiliary monomer. As the auxiliary monomer, there can be used olefins, fluorine-containing olefins, acrylic esters, methacrylic esters, fluorine-containing acrylic esters, fluorine-containing methacrylic esters, norbornene compounds, fluorine-containing norbornene compounds, styrenic compounds, fluorine-containing styrenic compounds, vinyl ethers and fluorine-containing vinyl ethers. Among others, acrylic esters, methacrylic esters, fluorine-containing acrylic esters, fluorine-containing methacrylic esters, norbornene compounds, fluorine-containing norbornene compounds, styrenic compounds, vinyl ethers and fluorine-containing vinyl ethers are preferred as the copolymerization component.

Specific examples of the olefins are ethylene and propylene. Specific examples of the fluoroolefins are vinyl fluoride, vinylidene fluoride, trifluoroethylene, chlorotrifluoroethylene, tetrafluoroethylene, hexafluoroethylene and hexafluoroisobutene.

There is no particular limitation on the ester side chain structure of the acrylic ester or methacrylic ester. Specific examples of the acrylic esters or methacrylic esters are known acrylic or methacrylic ester compounds: such as acrylic or methacrylic acid alkyl ester e.g. methyl acrylate or methacrylate, ethyl acrylate or methacrylate, n-propyl acrylate or methacrylate, isopropyl acrylate or methacrylate, n-butyl acrylate or methacrylate, isobutyl acrylate or methacrylate, n-hexyl acrylate or methacrylate, n-octyl acrylate or methacrylate, 2-ethylhexyl acrylate or methacrylate, lauryl acrylate or methacrylate, 2-hydroxyethyl acrylate or methacrylate, or 2-hydroxypropyl acrylate or methacrylate; acrylate or methacrylate containing an ethylene glycol group, propylene glycol group or tetramethylene glycol group; unsaturated amide e.g. acrylamide, methacrylamide, N-methylol acrylamide, N-methylol methacrylamide, or diacetone acrylamide; acrylonitrile; methacrylonitrile; alkoxysilane-containing vinylsilane or acrylic or methacrylic ester; t-butyl acrylate or methacrylate; 3-oxocyclohexyl acrylate or methacrylate; adamantyl acrylate or methacrylate; alkyladamantyl acrylate or methacrylate; cyclohexyl acrylate or methacrylate; tricyclodecanyl acrylate or methacrylate; acrylate or methacrylate having a ring structure such as lactone ring or norbornene ring; acrylic acid; and methacrylic acid. There can also be used an acrylate compound obtained by bonding a cyano group to the α-position of the above acrylate or analog thereof, such as maleic acid, fumaric acid or maleic anhydride.

Examples of the fluorine-containing acrylic esters or fluorine-containing methacrylic esters are acrylic esters or methacrylic esters each having a fluorine atom or a fluorine-containing group in α-position o of the acrylic acid group. For instance, the monomer having a fluoroalkyl group in its α-position o can suitably be exemplified by a monomer in which a trifluoromethyl group, a trifluoroethyl group, a nonafluoro-n-butyl group etc. has been added to the α-position o of the above non-fluorinated acrylic ester or methacrylic ester.

On the other hand, there can be used acrylic esters or methacrylic esters in which a fluorinated alkyl group e.g. a perfluoroalkyl group or a fluoroalkyl group is bonded to the ester moiety or in which a cyclic structure coexists with a fluorine atom in the ester moiety. The cyclic structure may be a fluorine-containing benzene ring, a fluorine-containing cyclopentane ring, a fluorine-containing cyclohexane ring, a fluorine-containing cycloheptane ring or the like having a fluorine atom or a trifluoromethyl group as a substituent. An acrylic ester or methacrylic ester in which the ester moiety is a fluorine-containing t-butyl ester group can also be used. Typical examples of such monomer units are 2,2,2-trifluoroethyl acrylate, 2,2,3,3-tetrafluoropropyl acrylate, 1,1,1,3,3,3-hexafluoroisopropyl acrylate, heptafluoroisopropyl acrylate, 1,1-dihydroheptafluoro-n-butyl acrylate, 1,1,5-trihydrooctafluoro-n-pentyl acrylate, 1,1,2,2-tetrahydrotridecafluoro-n-octyl acrylate, 1,1,2,2-tetrahydroheptadecafluoro-n-decyl acrylate, 2,2,2-trifluoroethyl methacrylate, 2,2,3,3-tetrafluoropropyl methacrylate, 1,1,1,3,3,3-hexafluoroisopropyl methacrylate, heptafluoroisopropyl methacrylate, 1,1-dihydroheptafluoro-n-butyl methacrylate, 1,1,5-trihydrooctafluoro-n-pentyl methacrylate, 1,1,2,2-tetrahydrotridecafluoro-n-octyl methacrylate, 1,1,2,2-tetrahydroheptadecafluoro-n-decyl methacrylate, perfluorocyclohexylmethyl acrylate and perfluorocyclohexylmethyl methacrylate.

As the norbornene compounds and fluorine-containing norbornene compounds, norbornene monomers having a mononuclear or multinuclear structure can be used without particular limitation. Suitable examples of the norbornene compounds are those each formed by Diels-Alder addition reaction of an unsaturated compound such as an allyl alcohol, a fluorine-containing allyl alcohol, an acrylic acid, an α-fluoroacrylic acid, a methacrylic acid and any of the acrylic esters, methacrylic esters, fluorine-containing acrylic esters and fluorine-containing methacrylic esters described in the present specification with cyclopentadiene or cyclohexadiene.

The styrenic compounds, fluorine-containing styrenic compounds, vinyl ethers, fluorine-containing vinyl ethers, allyl ethers, vinyl esters, vinyl silanes and the like are also usable. Examples of the styrenic compounds and fluorine-containing styrenic compounds are styrene, fluorinated styrene, hydroxystyrene, hexafluoroacetone-added styrenic compounds, trifluoromethyl-substituted styrene or hydroxystyrene and monomers obtained by bonding a halogen atom, an alkyl group or a fluoroalkyl group to the α-position of the above styrene or fluorine-containing styrenic compounds. Examples of the vinyl ethers and fluorine-containing vinyl ethers are: alkyl vinyl ethers having an alkyl group such as methyl or methyl or a hydroxyalkyl group such as hydroxyethyl or hydroxybutyl, in which a part or all of hydrogen atoms may be substituted with fluorine; and cyclic vinyl ethers such as cyclohexyl vinyl ether and cyclic vinyl ether containing a hydrogen or carbonyl bond in its cyclic structure, in which a part or all of hydrogen atoms may be substituted with fluorine. The allyl ethers, vinyl esters and vinyl silane can be used without particular limitation as long as they are known compounds.

One preferred example of the auxiliary repeating unit in the fluorine-containing sulfonate resin or fluorine-containing N-sulfonyloxyimide resin is a repeating unit of the following general formula (6).

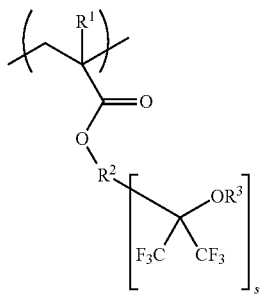

(6)

In the general formula (6), $R^1$ represents a hydrogen atom, a halogen atom or a $C_1$-$C_3$ alkyl or fluorine-containing alkyl group; $R^2$ represents a substituted or unsubstituted aliphatic hydrocarbon group, a substituted or unsubstituted aromatic group or a divalent organic group formed by combination of a plurality thereof; any number of hydrogen atoms of $R^2$ may be substituted with a fluorine atom; $R^2$ may contain an ether bond or a carbonyl group; $R^3$ represents a hydrogen atom, a substituted or unsubstituted $C_1$-$C_{25}$ aliphatic hydrocarbon group or a substituted or unsubstituted $C_1$-$C_{25}$ aromatic hydrocarbon group; any number of hydrogen atoms of $R^3$ may be substituted with a fluorine atom; $R^3$ may contain an ether bond or a carbonyl group; and s represents an integer of 2 to 8.

In the general formula (6), $R^1$ is exemplified as follows. Examples of the halogen atom as $R^1$ are fluorine, chlorine and bromine. Examples of the $C_1$-$C_3$ alkyl group as $R^1$ are methyl, ethyl, propyl and isopropyl. Examples of the $C_1$-$C_3$ fluorine-containing alkyl group as $R^1$ are those obtained by substitution of a part or all of hydrogen atoms of the above alkyl groups with a fluorine atom, such as trifluoromethyl (—$CF_3$), trifluoroethyl (—$CH_2CF_3$), 1,1,1,3,3,3-hexafluoroisopropyl and heptafluoroisopropyl. Among others, preferred are a hydrogen atom, a fluorine atom, a methyl group and a trifluoromethyl group.

Further, $R^2$ is a substituted or unsubstituted aliphatic hydrocarbon group, a substituted or unsubstituted aromatic group or a divalent organic group formed by combination of a plurality thereof in the general formula (6) as mentioned above. Any number of hydrogen atoms of $R^2$ may be substituted with a fluorine atom. The aliphatic hydrocarbon group may be straight, branched or cyclic. Examples of $R^2$ are: straight or branched aliphatic hydrocarbon groups such as methylene, ethylene, isopropylene and t-butylene; cyclic aliphatic hydrocarbon groups such as cyclobutylene, cyclohexylene, divalent norbornene and divalent adamantane; aromatic groups such as phenylene; divalent groups obtained by substitution of hydrogen atoms of the above groups with any substituent; and divalent groups obtained by replacement of carbon atoms of the above groups by an ether bond or a carbonyl group. These groups can be used without particular limitation.

As preferred examples of the repeating unit of the general formula (6), there can be used repeating units of the following general formulas (7) and (8).

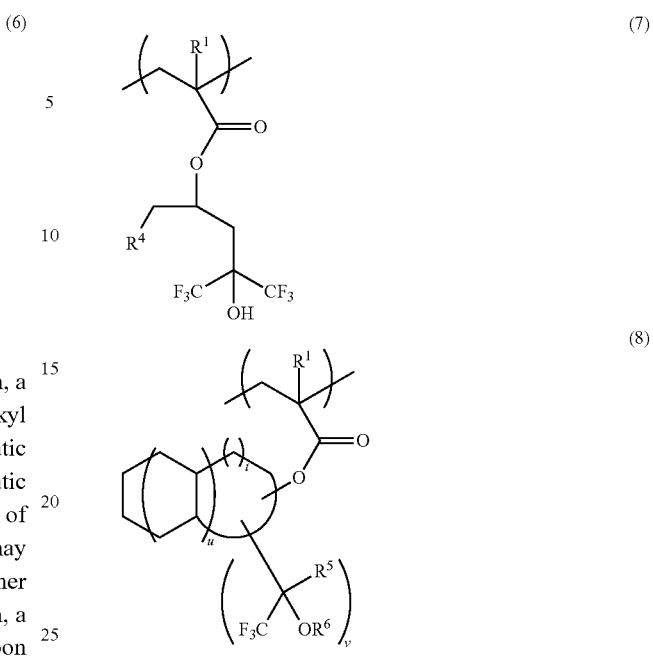

In the general formula (7), $R^1$ has the same definition as in the general formula (6); and $R^4$ represents a hydrogen atom or a $C_1$-$C_6$ alkyl or fluorine-containing alkyl group. Examples of the alkyl or fluorine-containing alkyl group as $R^4$ are methyl, ethyl, n-propyl, isopropyl, n-butyl, sec-butyl, tert-butyl, cyclopentyl, cyclohexyl, fluoromethyl, difluoromethyl, trifluoromethyl and perfluoroethyl. In the general formula (8), $R^1$ has the same definition as in the general formula (6); $R^5$ represents a methyl group or a trifluoromethyl group; $R^6$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an oxygen atom (ether bond) or a carbonyl group; u represents an integer of 0 to 2; t and v represent an integer of 1 to 8 and satisfy a relationship of v≤t+2; and, in the case where there are a plurality of $R^5$ and $R^6$ (v is an integer of 2 or greater), $R^5$ and $R^6$ may be the same or different. As $R^6$, a hydrogen atom is particularly preferred.

Examples of the substituted or unsubstituted $C_1$-$C_{25}$ aliphatic hydrocarbon group or substituted or unsubstituted $C_1$-$C_{25}$ aromatic hydrocarbon group as $R^6$ are methyl, ethyl, propyl, isopropyl, cyclopropyl, n-propyl, sec-butyl, tert-butyl, n-pentyl, cyclopentyl, sec-pentyl, neopentyl, hexyl, cyclohexyl, ethylhexyl, norbornel, adamantyl, vinyl, aryl, butenyl, pentenyl, ethynyl, phenyl, benzyl and 4-methoxybenzyl, in each of which a part or all of hydrogen atoms may be substituted with a fluorine atom. As the oxygen-containing hydrocarbon group, an alkoxycarbonyl group, an acetal group or an acyl group can be used. Examples of the alkoxycarbonyl group are tert-butoxycarbonyl, tert-amyloxycarbonyl, methoxycarbonyl, ethoxycarbonyl and i-propoxycarbonyl. Examples of the acetal group are are: linear ethers such as methoxymethyl, methoxyethoxymethyl, ethoxyethyl, butoxyethyl, cyclohexyloxyethyl, benzyloxyethyl, phenethyloxyethyl, ethoxypropyl, benzyloxypropyl, phenethyloxypropyl, ethoxybutyl and ethoxyisobutyl; and cyclic ethers such as tetrahydrofuranyl and tetrahydropyranyl. Examples of the acyl group are acetyl, propionyl, butyryl, heptanoyl, hexanoyl, valeryl, pivaloyl, isovaleryl, lauryloyl, myristoyl, palmitoyl, stearoyl, oxalyl, malonyl, succinyl, glutaryl, adipoyl, piperoyl, suberoyl, azelaoyl, sebacoyl, acryloyl, propioyl, methacryloyl, crotonoyl, oleoyl, maleoyl, fumaroyl, mesaconoyl, camphoroyl, benzoyl, phthaloyl, isophtaloyl, terephthaloyl, naphthoyl, toluoyl, hydratropoyl, atropoyl, cinnamoyl, furoyl, thenoyl, nicotinoyl and isonicotinoyl. All or part of hydrogen atoms of the above groups can be substituted with fluorine.

The following are particularly preferred examples of the repeating unit of the general formula (7) or (8). These preferred repeating units may preferably be used in combination with the other auxiliary repeating unit.

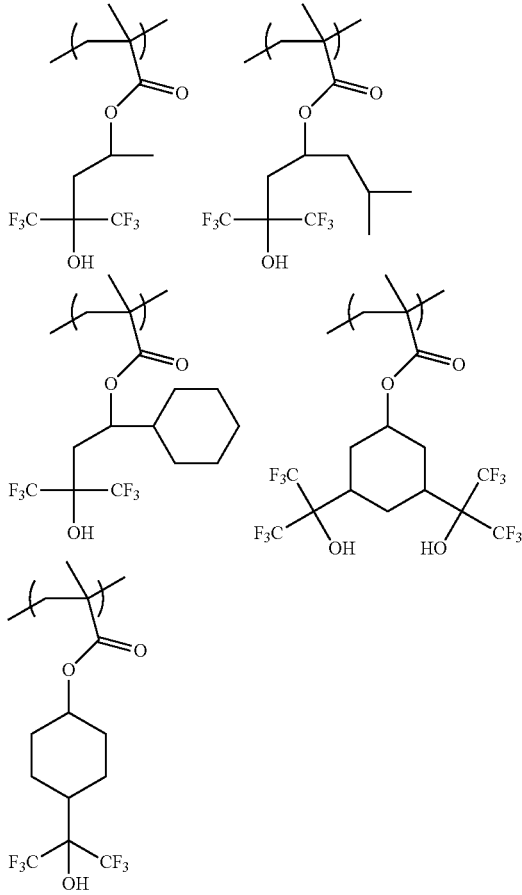

Another preferred example of the auxiliary repeating unit in the fluorine-containing sulfonate resin or fluorine-containing N-sulfonyloxyimide is a repeating unit of the following general formula (9).

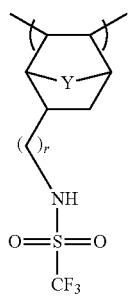

(9)

In the general formula (9), Y represents either —$CH_2$—, —O— or —S—; and r represents an integer of 2 to 6.

The following are particularly preferred examples of the repeating unit of the general formula (9). These preferred repeating units may preferably be used in combination with the other auxiliary repeating unit.

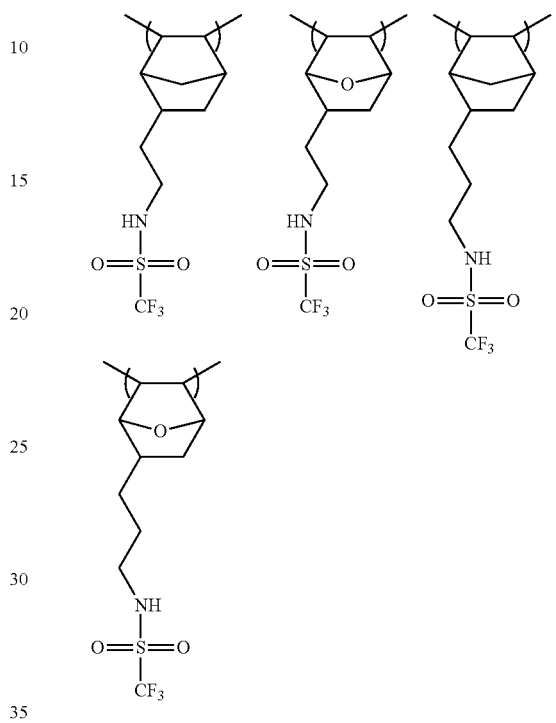

Another preferred example of the auxiliary repeating unit in the fluorine-containing sulfonate resin or fluorine-containing N-sulfonyloxyimide resin is a repeating unit of the following general formula (10).

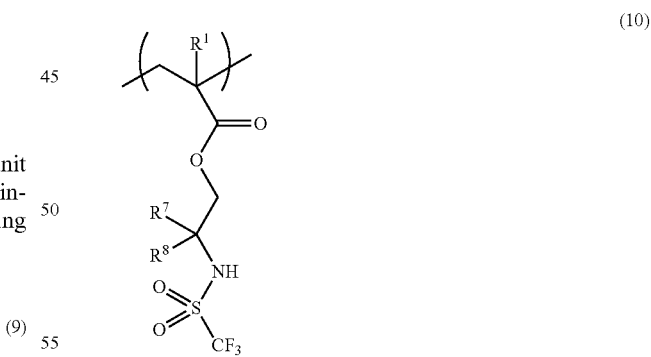

(10)

In the general formula (10), $R^1$ has the same definition as in the general formula (6); and $R^7$ and $R^8$ each independently represent a hydrogen atom, a substituted or unsubstituted $C_1$-$C_{25}$ straight, branched or cyclic aliphatic hydrocarbon group or a substituted or unsubstituted $C_1$-$C_{25}$ aromatic hydrocarbon group; any number of hydrogen atoms of $R^7$, $R^8$ may be substituted with a fluorine atom; and $R^7$, $R^8$ may contain an ether bond or a carbonyl group. Examples of $R^7$, $R^8$ in the general formula (10) are the same as those of $R^6$ in the general formula (8).

The following are particularly preferred examples of the repeating unit of the general formula (10). These preferred repeating units may preferably be used in combination with the other auxiliary repeating unit.

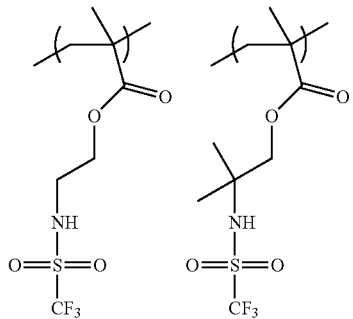

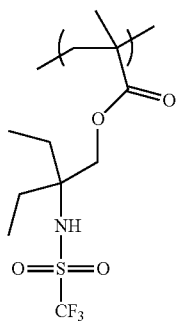

Another preferred example of the auxiliary repeating unit in the fluorine-containing sulfonate resin or fluorine-containing N-sulfonyloxyimide resin is a repeating unit of the following general formula (11).

(11)

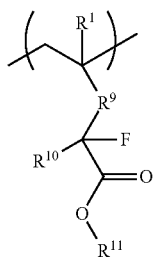

In the general formula (11), $R^1$ has the same definition as in the general formula (6); $R^{11}$ corresponds in definition to $R^6$ in the general formula (8); $R^9$ represents a divalent linking group and corresponds in definition to the linking group W, $W^1$; and $R^{10}$ represents a hydrogen atom, a fluorine atom or a fluorine-containing alkyl group. The fluorine-containing alkyl group can be used without particular limitation. Examples of the fluorine-containing alkyl group are those of 1 to 12 carbon atoms, preferably 1 to 3 carbon atoms, such as trifluoromethyl, pentafluoromethyl, 2,2,2-trifluoroethyl, n-heptafluoropropyl, 2,2,3,3,3-pentafluoropropyl, 3,3,3-trifluoropropyl and 1,1,1,3,3,3-hexafluoropropyl. As $R^{10}$, a fluorine atom or a trifluoromethyl group is particularly preferred.

The following are particularly preferred examples of the repeating unit of the general formula (10). These preferred repeating units may preferably be used in combination with the other auxiliary repeating unit.

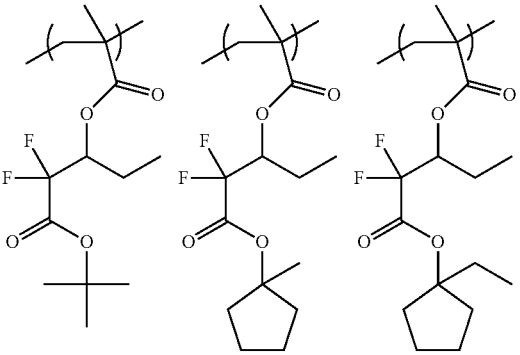

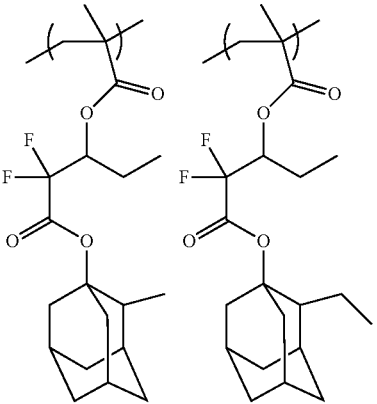

Another preferred example of the auxiliary repeating unit in the fluorine-containing sulfonate resin or fluorine-containing N-sulfonyloxyimide resin is a repeating unit of the following general formula (16).

(16)

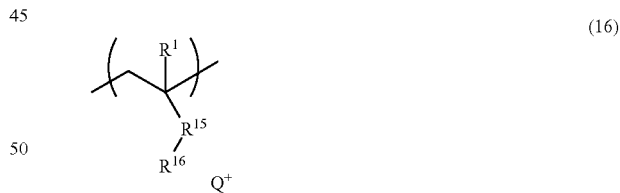

In the general formula (16), $R^1$ represents a hydrogen atom, a halogen atom or a $C_1$-$C_3$ alkyl or fluorine-containing alkyl group; $R^{15}$ represents a divalent linking group; $R^{16}$ represents a monovalent group having a monovalent anion site, preferably either —$SO_3^-$, —$CO_2^-$ or —$N^-HSO_3$; and $Q^+$ represents a monovalent cation, preferably either a sulfonium cation or an iodonium cation. The linking group $R^{15}$ has the same definition as the linking group W in the general formula (4) and thus will not be explained repeatedly.

The following are particularly preferred examples of the repeating unit of the general formula (11). These preferred repeating units may preferably be used in combination with the other auxiliary repeating unit.

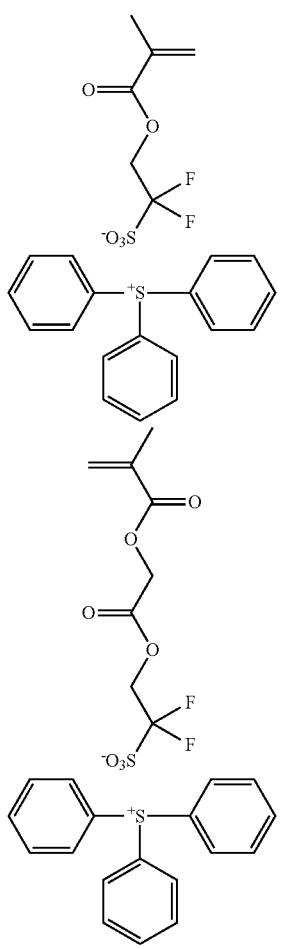

[Polymerization of Fluorine-Containing Sulfonate Resin or Fluorine-Containing N-Sulfonyloxyimide Resin]

There is no particular limitation on the polymerization process for production of the resin having the repeating unit of the general formula (4) or (17) in the present invention. It is preferable to adopt radical polymerization process or ionic polymerization process. In some cases, it is feasible to adopt coordination anionic polymerization process, living anionic polymerization process, cationic polymerization process, ring opening metathesis polymerization process, vinylene polymerization process, or vinyl addition process. The polymerization reaction can be performed by any common polymerization process. The following explanations will be specifically given to the radial polymerization process. It is however obvious that the polymerization reaction can be easily performed by any other polymerization process with reference to public documents and the like.

The radical polymerization process can be done by a known polymerization technique such as bulk polymerization, solution polymerization, suspension polymerization or emulsion polymerization technique in a batch, semi-continuous or continuous system in the presence of a radical polymerization initiator or a radical initiating source.

There is no particular limitation on the radical polymerization initiator. As the radical polymerization initiator, there can be used azo compounds, peroxide compounds and redox compounds. Preferred examples of the radical polymerization initiator are azobisbutyronitrile, dimethyl-2,2-azobis(2-methylpropionate), tert-butylperoxypivalate, di-tert-butyl peroxide, i-butyryl peroxide, lauroyl peroxide, succinic peroxide, dicinnamyl peroxide, di-n-propylperoxydicarbonate, tert-butylperoxyallyl monocarbonate, benzoyl peroxide, hydrogen peroxide and ammonium persulfate.

There is also no particular limitation on the reaction vessel used in the polymerization reaction. Further, the polymerization reaction can be performed with the use of a polymerization solvent. As the polymerization solvent, preferred are those that do not interfere with the radical polymerization process. Typical examples of the polymerization solvent are: ester solvents such as ethyl acetate and n-butyl acetate; ketone solvents such as acetone and methyl isobutyl ketone; hydrocarbon solvents such as toluene and cyclohexane; and alcohol solvents such as methanol, isopropyl alcohol and ethylene glycol monomethyl ether. Water, ether solvents, cyclic ether solvents, fluorocarbon solvents and aromatic solvents can also be used. These solvents can be used solely or in combination of two or more thereof. A molecular weight adjusting agent such as mercaptan may be used in combination.

The reaction temperature of the copolymerization reaction is set as appropriate depending on the kind of the radical polymerization initiator or radical initiating source and is generally preferably in the range of 20 to 200° C., more preferably 30 to 140° C.

As a technique for removing water or the organic solvent from the obtained fluorine-containing polymer solution or dispersion, it is feasible to adopt reprecipitation, filtration, distillation by heating under reduced pressure or the like.

[Resist Composition]

In the present invention, the resin having the repeating unit of the general formula (4) or (17) is used in a resist composition in the form of a solution mixed with other components. This sulfonate resin or N-sulfonyloxyimide resin functions as a photoacid generator. In the case where the sulfonate resin or N-sulfonyloxyimide resin has the repeating unit with the acid labile group or cross-linking site, the sulfonate resin or N-sulfonyloxyimide resin can be used solely as a chemically amplified resist resin without the addition of any resin having a repeating unit with an acid labile group or cross-linking site (base resin). In the case where the resin has the repeating unit of the general formula (4) or (17) but does not have the repeating unit with the acid labile group or cross-linking site, the resist composition is prepared with the addition of a base resin as an essential component to the resin. The resist composition includes not only a solvent but also various additives commonly used for resist compositions, such as an additive resin, a quencher, a dissolution inhibitor, a plasticizer, a stabilizer, a coloring agent, a surfactant, a viscosity improver, a leveling agent, an antifoaming agent, a compatibilizer, a primer and an antioxidant. In the case of the negative resist composition, other additives such as a cross-linking agent and a basic compound may further be added. As these additives, there can suitably be used any of known additives in addition to the following compounds.

[Base Resin]

The base resin refers to a resin containing an acid labile group so as to perform a positive resist function or a resin containing a cross-linking site so as to perform a negative resist function. As mentioned above, the above photosensitive solubility-changeable sulfonate resin can be used as the base resin.

Examples of the base resin for the positive resist composition are those having a leaving site such as carboxyl group or hydroxyl group protected by an acid labile group on a side chain thereof and a main chain structure of repeating unit formed by cleavage of a polymerizable double bond group such as acrylic acid, methacrylic acid, α-trifloromethylacrylic acid, vinyl group, allyl group or norbornenyl group.

Examples of the base resin for the negative resist composition are those having a cross-linking site such as hydroxyl group or carboxyl group on a side chain thereof and a main chain of repeating unit formed by cleavage of a polymerizable double bond group such as acrylic acid, methacrylic acid, α-trifloromethylacrylic acid, vinyl group, allyl group or norbornene group.

In many cases, the base resin is copolymer form for control of the resist characteristics. There are known various base resins. Herein, the above explanations of the copolymerization component, the acid labile group, cross-linking site and linking group can be applied as they are to the base resin. As the copolymerization component of the base resin, a lactone ring-containing monomer is particularly preferred for improvement in the substrate adhesion of the resist composition.

The repeating unit of the general formula (4) or (17) may be contained in the base resin.

The base resin generally has a mass-average molecular weight of 1,000 to 1,000,000, preferably 2,000 to 500,000, as measured by gel permeation chromatography (GPC). If the mass-average molecular weight of the base resin is less than 1,000, the resulting resist composition is not formed into a film with sufficient strength. If the mass-average molecular weight of the base resin exceeds 1,000,000, the solubility of the resin in the solvent becomes lowered so that it is unfavorably difficult to form the resist composition into a smooth film. The molecular weight distribution (Mw/Mn) of the base resin is preferably in the range of 1.01 to 5.00, more preferably 1.01 to 4.00, still more preferably 1.01 to 3.00, most preferably 1.10 to 2.50.

[Additives]

In the case of the negative resist composition, there can be used any of known cross-linking agents for chemically amplified negative resist compositions.

More specifically, the cross-linking agent can be any compound formed by reacting an amino-containing compound such as melamine, acetoguanamine, benzoguanamine, urea, ethylene urea, propylene urea or glycoluril, with formaldehyde or a mixture of formaldehyde and lower alcohol, and thereby substituting a hydrogen atom of the amino group with a hydroxymethyl group or a lower alkoxymethyl group. Herein, the cross-linking agents using melamine, urea, alkylene urea e.g. ethylene urea, propylene urea etc. and glycoluril are hereinafter referred to as "melamine-based cross-linking agent", "urea-based cross-linking agent", "alkylene urea-based cross-linking agent" and "glycoluril-based cross-linking agent", respectively. The cross-linking agent is preferably at least one selected from the group consisting of melamine-based cross-linking agents, urea-based cross-linking agents, alkylene urea-based cross-linking agents and glycoluril-based cross-linking agents. Particularly preferred are glycoluril-based cross-linking agents.

Examples of the melamine-based cross-linking agents are hexamethoxymethylmelamine, hexaethoxymethylmelamine, hexapropoxymethylmelamine and hexabutoxymethylmelamine. Among others, hexamethoxymethylmelamine is preferred.

Examples of the urea-based cross-linking agents are bismethoxymethylurea, bisethoxymethylurea, bispropoxymethylurea and bisbutoxymethylurea. Among others, bismethoxymethylurea is preferred.

Examples of the alkylene urea-based cross-linking agents are: ethylene urea-based cross-linking agents such as mono- and/or di-hydroxymethylated ethylene urea, mono- and/or di-methoxymethylated ethylene urea, mono- and/or di-ethoxymethylated ethylene urea, mono- and/or di-propoxymethylated ethylene urea and mono- and/or di-butoxymethylated ethylene urea; propylene urea-based cross-linking agents such as mono- and/or di-hydroxymethylated propylene urea, mono- and/or di-methoxymethylated propylene urea, mono- and/or di-ethoxymethylated propylene urea, mono- and/or di-propoxymethylated propylene urea and mono- and/or di-butoxymethylated propylene urea; 1,3-di(methoxymethyl)-4,5-dihydroxy-2-imidazolidinone; and 1,3-di(methoxymethyl)-4,5-dimethoxy-2-imidazolidinone.

Examples of the glycoluril-based cross-linking agents are mono-, di-, tri- and/or tetra-hydroxymethylated glycoluril, mono-, di-, tri- and/or tetra-methoxymethylated glycoluril, mono-, di-, tri- and/or tetra-ethoxymethylated glycoluril, mono-, di-, tri- and/or tetra-propoxymethylated glycoluril and mono-, di-, tri- and/or tetra-butoxymethylated glycoluril.

The total amount of the cross-linking agent used is preferably 3 to 30 parts by mass, more preferably 3 to 25 parts by mass, most preferably 5 to 20 parts by mass, per 100 parts by mass of the base resin in the negative resist composition. If the total amount of the cross-linking agent is less than 3 parts by mass, the resist composition may not form sufficient cross-linking for good resist pattern. The resist composition may be poor in storage stability and may deteriorate in sensitivity with time if the total amount of the cross-linking agent exceeds 30 parts by mass.

The basic compound is preferably contained as an optional component in the resist composition so as to function as a quencher or to obtain improvements in resist pattern shape and post exposure stability.

There can be used any known basic compounds such as primary, secondary and tertiary aliphatic amines, aromatic amines, heterocyclic amines, nitrogen-containing compounds with hydroxyphenyl group, alcoholic nitrogen-containing compounds and amide derivatives. Among others, secondary and tertiary aliphatic amines, aromatic amines and heterocyclic amines are preferred.

The aliphatic amines can be in the form of alkylamines or alkylalcoholamines each obtained by replacing at least one hydrogen atom of ammonia ($NH_3$) with a $C_1$-$C_{12}$ alkyl or hydroxyalkyl group. Examples of the aliphatic amines are: monoalkylamines such as n-hexylamine, n-heptylamine, n-octylamine, n-nonylamine and n-decylamine; dialkylamines such as diethylamine, di-n-propylamine, di-n-heptylamine, di-n-octylamine and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine and tri-n-dodecylamine; and alkylalcoholamines such as diethanolamine, triethanolamine, diisopropanolamine, triisopropanolamine, di-n-octanolamine and tri-n-octanolamine. Above all, alkylacoholamines and trialkylamines are preferred. More preferred are alkylalcoholamines. Among the alkylalcoholamines, triethanolamine and triisopropanolamine are particularly preferred.

Other examples of the basic compound are: aromatic or heterocyclic amines including aniline, aniline derivatives such as N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline and N,N-dimethyltoluidine, heterocyclic amines such as 1,5-diazabicyclo[4.3.0]non-5-ene, 1,8-diazabicyclo[5.4.0]undec-7-ene, 1,4-diazabicyclo[2.2.2]octane, 4-dimethylaminopyridine, hexamethylenetetramine and 4,4- dimethylimidazoline, and hindered amines such as bis(1,2,2,6,6-pentamethyl-4-piperidyl)sebacate; and alcoholic nitrogen-containing compounds such as 2-hydroxypyridine, aminocresol, 2,4-quinolinediole, 3-indole methanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, and 1-[2-(2-hydroxyethoxy)ethyl]piperazine.

The above basic compounds can be used solely or in combination of two or more thereof.

The amount of the basic compound used is generally 0.01 to 5 parts by mass per 100 parts by mass of the base resin.

In the case of the negative resist resin, an organic carboxylic acid or a phosphorus oxo acid or derivative thereof may be added an optional component in order to prevent sensitivity deterioration caused by the addition of the basic compound and to obtain improvements in resist pattern shape and post exposure stability. This acid compound can be used solely or in combination with the basic compound.

Suitable examples of the organic carboxylic acid are malonic acid, citric acid, malic acid, succinic acid, benzoic acid and salicylic acid.

Suitable examples of the phosphorus oxo acid or its derivative are: phosphoric acids and ester derivatives thereof, such as phosphoric acid, di-n-butyl phosphate and diphenyl phosphate; phosphonic acids and ester derivatives thereof, such as phosphonic acid, dimethyl phosphonate, di-n-butyl phosphonate, phenylphosphonic acid, diphenyl phosphonate and dibenzyl phosphonate; and phosphinic acids or ester derivatives thereof, such as phosphinic acid and phenylphosphinic acid. Among others, phosphonic acid is particularly preferred.

[Solvent]

One method of forming the resist composition into a thin film is to dissolve the resin etc. in an organic solvent, and then, apply and dry the resulting resist solution. There is no particular limitation on the organic solvent as long as the fluorine-containing sulfonate resin or fluorine-containing N-sulfonyloxyimide resin can be dissolved in the organic solvent. Examples of the organic solvent are: ketones such as acetone, methyl ethyl ketone, cyclohexanone, methyl isoamyl ketone and 2-heptanone; polyhydric alcohols and derivatives thereof, such as monomethyl ether, monoethyl ether, monopropyl ether, monobutyl ether or monophenyl ether of ethylene glycol, ethylene glycol monoacetate, diethylene glycol, diethylene glycol monoacetate, propylene glycol, propylene glycol monoacetate, propylene glycol monomethyl ether, propylene glycol monomethyl etheracetate (PGMEA), dipropylene glycol or dipropylene glycol monoacetate; cyclic ethers such as dioxane; esters such as methyl lactate, ethyl lactate, methyl acetate, ethyl acetate, butyl acetate, methyl pyruvate, ethyl pyruvate, methyl methoxypropionate and ethyl ethoxypropionate; aromatic solvents such as xylene and toluene; and fluorinated solvents such as fluorocarbon, hydrofluorocarbon, perfluoro compound and hexafluoroisopropyl alcohol. There can also be used a high-boiling-point weak solvent such as turpentine-based petroleum naphtha solvent or paraffin solvent for improvement in ease of application. These solvents can be used solely or in combination of two or more thereof

[Surfactant]

The surfactant, preferably either one or two or more of fluorine- and/or silicon-based surfactants (fluorine-based surfactant, silicon-based surfactants and surfactant containing both of fluorine and silicon atoms) is contained in the resist composition.

The addition of such a surfactant into the resist composition is effective for use with an exposure light source of 250 nm or less wavelength, notably 220 nm or less wavelength and for pattern formation with a narrower pattern line width. It is possible to attain good sensitivity and resolution and obtain good resist patterning with less adhesion/development failures.

[Acid Generator]

In the resist composition, any ordinary, non-resinous photoacid generator can be used in combination with the fluorine-containing sulfonate resin or fluorine-containing N-sulfonyloxyimide resin. It is feasible to use any one selected from photoacid generators for chemically amplified resist compositions. Examples of the photoacid generator are bis-sulfonyldiazomethanes, nitrobenzyl derivatives, onium salts, halogen-containing triazine compounds, cyano-containing oximesulfonate compounds and other oximesulfonate compounds. These photoacid generators can be used solely or in combination of two or more thereof. The amount of the photoacid generator used, including the sulfonate resin or N-sulfonyloxyimide resin according to the present invention, is generally in the range of 0.5 to 20 parts by mass per 100 parts by mass of the resist composition. If the amount of the photoacid generator is less than 0.5 parts by mass, the resin composition unfavorably results in insufficient pattern formation. If the amount of the photoacid generator exceeds 20 parts by mass, it is difficult to prepare the resin composition into a uniform solution. Further, the resin composition unfavorably tends to become low in storage stability. The fluorine-containing sulfonate resin or fluorine-containing N-sulfonyloxyimide resin according to the present invention is generally used in an amount of 1 to 100 parts by mass, preferably 10 to 100 parts by mass, more preferably 30 to 100 parts by mass, per 100 parts by mass of the total photoacid generator content.

[Additive Resin]

There is no particular limitation on the additive resin as long as the additive resin can be dissolved in the solvent used and has compatibility with the other components of the resist composition. The additive resin functions as a plasticizer, a stabilizer, a viscosity improver, a leveling agent, an antifoaming agent, a compatibilizer, a primer etc.

[Pattern Formation Method]

In the present invention, the resist composition can be used for resist pattern formation by a conventional photoresist technique. For example, the resist composition is first prepared in solution form, applied to a substrate such as a silicon wafer by e.g. a spinner and dried to thereby form a photosensitive film of the resist composition. The photosensitive film is irradiated with high energy radiation or electron beam by e.g. an exposure device through a desired mask pattern, and then, subjected to heating. Subsequently, the photosensitive film is developed with an alkaline developer such as 0.1 to 1 mass % tetramethylammoniumhydroxide solution. It is possible by the above method to form a resist pattern according to the mask pattern.

There is no particular limitation on the high energy ray radiation used in the present invention. It is particularly effective to use an exposure device having a light source for irradiating high energy radiation of 300 nm or less wavelength, such as short-wavelength UV radiation or electron beam radiation. Further, the resist composition according to the present invention can be applied suitably and effectively to a liquid immersion exposure device, which uses a medium causing less absorption of high energy radiation, such as water or fluorinated solvent, in a part of optical path and enables more efficient fine processing in terms of numerical aperture and effective wavelength.

EXAMPLES

Hereinafter, the present invention will be described in more detail below by way of the following synthesis examples, polymerization examples, working examples and comparative examples. It should be noted that the following working examples are illustrative and are not intended to limit the present invention thereto.

[Synthesis of Compounds]

Synthesis Example 1

Triphenylsulfonium 2-[(2-Methacryloyloxy)ethylcarbamoyloxy]-1,1-difluoroethanesulfonate

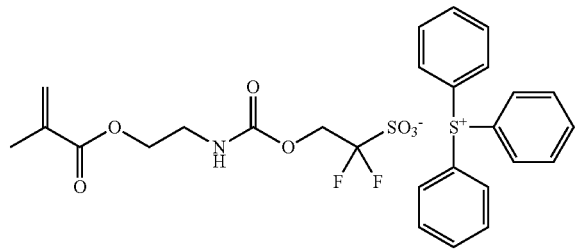

In 480 mL of acetonitrile, 131 g of a white solid of triphenylsulfonium 2-hydroxy-1,1-difluoroethanesulfonate (purity: 92.1%, equivalent to 0.284 mol) was dissolved by stirring. The resulting solution was admixed with 0.60 g (5.16 mmol) of N,N-dimethylaminopyridine and 0.4 g of 2,2'-methylene-bis(4-methyl-6-tert-butylphenol), followed by heating the solution to 45° C. and dropping a solution of 40 g (0.256 mol) of 2-methacryloyloxyethyl isocyanate in acetonitrile (120 mL) into the solution over about 30 minutes. After that, the solution was reacted at 45° C. over a night. To the thus-obtained reaction solution added was 600 mL of water. The reaction solution was subsequently subjected to concentration under reduced pressure to remove the acetonitrile from the reaction solution. The remaining aqueous solution was extracted with 480 mL of chloroform. The resulting organic layer was purified by washing the organic layer four times with 600 mL of water, concentrating the organic layer, dissolving the concentrate in twice as much weight of chloroform (rich solvent), and then, washing the solution five times with the same weight of diisopropyl ether (poor solvent) (liquid-liquid distribution). With this, 129 g of a chloroform solution of the target compound was obtained (yield: 52%, purity: 99%, target compound: 77.5 g, content rate: 60%).

Properties of triphenylsulfonium 2-[(2-methacryloyloxy)ethylcarbamoyloxy]-1,1-difluoroethanesulfonate $^1$H NMR (measurement solvent: deuterated chloroform, reference material: tetramethylsilane): δ=7.76-7.63 (m, 15H; Ph$_3$S$^+$), 6.07 (s, 1H; =CH$_2$), 5.53 (t, J=1.6 Hz, 2H; =CH$_2$), 5.38 (s, 1H; NH), 4.72 (t, J=15.0 Hz, 2H; CF$_2$CH$_2$), 4.16 (t, J=5.4 Hz, 2H; OCH$_2$), 3.44 (q, J=5.3 Hz, 2H; NHCH$_2$), 1.88 (t, J=1.1 Hz, 3H, CH$_3$).

$^{19}$F NMR (measurement solvent: deuterated chloroform, reference material: trichlorofluoromethane): δ=−114.3 (t, J=16.0 Hz, 2F).

Synthesis Example 2

Diphenyliodonium 2-Pivaloyloxy-1,1-difluoroethanesulfonate

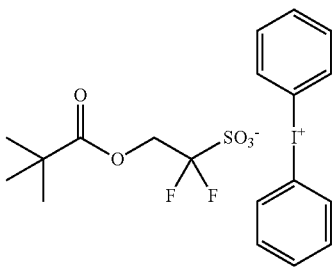

In 10 mL of chloroform, 5 g of a solid of triethylammonium 2-pivaloyloxy-1,1-difluoroethanesulfonate (equivalent to 14.4 mmol) was dissolved by stirring. The resulting solution was admixed with 15 mL of water and 4.78 g (15.1 mmol) of diphenyliodonium chloride, and then, reacted at room temperature for 3 hours. The thus-obtained reaction solution was separated into an organic layer and an aqueous layer. The organic layer was washed five times with 15 mL of water and subjected to concentration under reduced pressure. With this, 7.32 g of the target compound was obtained as a white solid (purity: 90%, yield: 90%).

Properties of diphenyliodonium 2-pivaloyloxy-1,1-difluoroethanesulfonate $^1$H NMR (measurement solvent: deuterated chloroform, reference material: tetramethylsilane): δ=7.97 (d, J=8.0 Hz, 4H; Ph$_2$I$^+$), 7.55 (d, J=7.4 Hz, 2H; Ph$_2$I$^+$), 7.41 (t, J=7.8 Hz, 4H; Ph$_{2I+}$), 4.55 (t, J=15.0 Hz, 2H; CH$_2$CF$_2$), 1.19 (s, 9H).

$^{19}$F NMR (measurement solvent: deuterated chloroform, reference material: trichlorofluoromethane): δ=−114.1 (t, J=16.2 Hz, 2F).

Synthesis Example 3

Diphenyliodonium 2-Hydroxy-1,1-difluoroethanesulfonate

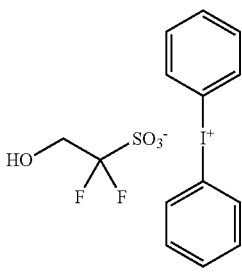

In 10 mL of chloroform, 7.32 g of a solid of diphenyliodonium 2-pivaloyloxy-1,1-difluoroethanesulfonate (purity: 90%, equivalent to 13.0 mmol) was dissolved by stirring. The resulting solution was admixed with 26 mL of methanol and 52 mg (1.30 mmol) of sodium hydroxide, and then, reacted at room temperature for 4 hours. To the thus-obtained reaction solution, 0.145 g (1.43 mmol) of concentrated hydrochloric acid was added. The reaction solution was subsequently subjected to concentration under reduced pressure. With this, 5.35 g of the target compound was obtained as a white solid (yield: 97%, purity: 90%).

Properties of diphenyliodonium 2-hydroxy-1,1-difluoroethanesulfonate $^1$H NMR (measurement solvent: deuterated dimethyl sulfoxide, reference material: tetramethylsilane): δ=8.21 (d, J=7.6 Hz, 4H; Ph$_2$I$^+$), 7.61 (t, J=7.4 Hz, 2H; Ph$_2$I$^+$), 7.50 (t, J=7.8 Hz, 4H; Ph$_2$I$^+$), 3.81 (t, J=16.0 Hz, 2H; CH$_2$).
$^{19}$F NMR (measurement solvent: deuterated dimethyl sulfoxide, reference material: trichlorofluoromethane): δ=−115.6 (t, J=18.0 Hz, 2F).

Synthesis Example 4

Diphenyliodonium 2-[(2-Methacryloyloxy)ethylcarbamoyloxy]-1,1-difluoroethanesulfonate

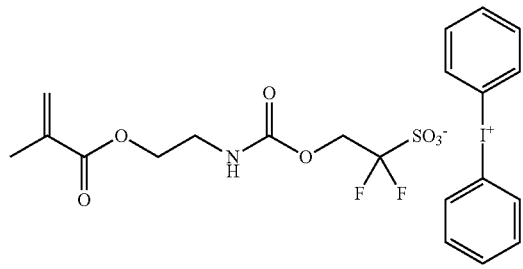

In 21 mL of acetonitrile, 5.35 g of a white solid of diphenyliodonium 2-hydroxy-1,1-difluoroethanesulfonate (purity: 90%, equivalent to 12.6 mmol) was dissolved by stirring. The resulting solution was admixed with 28.0 mg (0.229 mmol) of N,N-dimethylaminopyridine and 17.8 mg of 2,2'-methylene-bis(4-methyl-6-tert-butylphenol), followed by heating the solution to 45° C. and dropping a solution of 1.78 g (11.1 mmol) of 2-methacryloyloxyethyl isocyanate in acetonitrile (5.3 mL) into the solution over about 30 minutes. After that, the solution was reacted at 45° C. over a night. To the thus-obtained reaction solution added was 27 mL of water. The reaction solution was subsequently subjected to concentration under reduced pressure to remove the acetonitrile from the reaction solution. The remaining aqueous solution was extracted with 21 mL of chloroform. The resulting organic layer was purified by washing the organic layer four times with 27 mL of water, concentrating the organic layer, dissolving the concentrate in eight times as much weight of chloroform (rich solvent), and then, washing the solution five times with the same weight of diisopropyl ether (poor solvent) (liquid-liquid distribution). With this, 4.97 g of a chloroform solution of the target compound was obtained (yield: 50%, purity: 90%, target compound: 2.98 g, content rate: 60%).

Properties of diphenyliodonium 2-[(2-methacryloyloxy)ethylcarbamoyloxy]-1,1-difluoroethanesulfonate $^1$H NMR (measurement solvent: deuterated chloroform, reference material: tetramethylsilane): δ=7.96 (d, J=7.6 Hz, 4H; Ph$_2$I$^+$), 7.45 (t, J=7.4 Hz, 2H; Ph$_2$I$^+$), 7.32 (t, J=7.8 Hz, 4H; Ph$_2$I$^+$), 6.07 (s, 1H; =CH$_2$), 5.53 (t, J=1.6 Hz, 2H; =CH$_2$), 5.38 (s, 1H; NH), 4.72 (t, J=15.0 Hz, 2H; CF$_2$CH$_2$), 4.16 (t, J=5.4 Hz, 2H; OCH$_2$), 3.44 (q, J=5.3 Hz, 2H; NHCH$_2$), 1.88 (t, J=1.1 Hz, 3H; CH$_3$).
$^{19}$F NMR (measurement solvent: deuterated chloroform, reference material: trichlorofluoromethane): δ=−114.3 (t, J=16.0 Hz, 2F).

Synthesis Example 5

Tolyldiphenyl 2-[(2-Methacryloyloxy)ethylcarbamoyloxy]-1,1-difluoroethanesulfonate

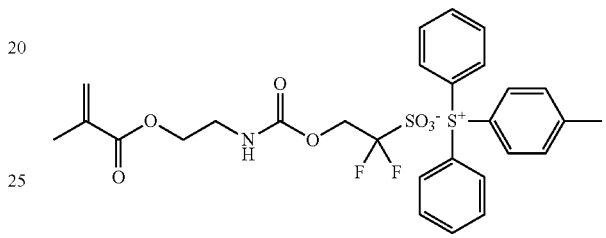

In 70 mL of acetonitrile, 16.9 g of a white solid of tolyldiphenylsulfonium 2-hydroxy-1,1-difluoroethanesulfonate (purity: 91.7%, equivalent to 35.4 mol) was dissolved by stirring. The resulting solution was admixed with 0.79 g (6.4 mmol) of N,N-dimethylaminopyridine and 0.1 g of 2,2'-methylene-bis(4-methyl-6-tert-butylphenol), followed by heating the solution to 45° C. and dropping a solution of 5 g (32.2 mmol) of 2-methacryloyloxyethyl isocyanate in acetonitrile (16 mL) into the solution over about 30 minutes. After that, the solution was reacted at 45° C. over a night. To the thus-obtained reaction solution added was 81 mL of water. The reaction solution was subsequently subjected to concentration under reduced pressure to remove the acetonitrile from the reaction solution. The remaining aqueous solution was extracted with 63 mL of chloroform. The resulting organic layer was purified by washing the organic layer four times with 81 mL of water, concentrating the organic layer, dissolving the concentrate in eight times as much weight of chloroform (rich solvent), and then, washing the solution five times with the same weight of diisopropyl ether (poor solvent) (liquid-liquid distribution). With this, 14.3 g of a chloroform solution of the target compound was obtained (yield: 44%, purity: 98%, target compound: 8.6 g, content rate: 60%).

Properties of tolyldiphenyl 2-[(2-methacryloyloxy) ethylcarbamoyloxy]-1,1-difluoroethanesulfonate $^1$H NMR (measurement solvent: deuterated chloroform, reference material: tetramethylsilane): δ=7.76-7.63 (m, 14H; MePhPh$_2$S$^+$), 6.05 (s, 1H; =CH$_2$), 5.54 (t, J=1.6 Hz, 1H; =CH$_2$), 5.36 (s, 1H; NH), 4.74 (t, J=15.0 Hz, 2H; CF$_2$CH$_2$), 4.12 (t, J=5.4 Hz, 2H; OCH$_2$), 3.41 (q, J=5.3 Hz, 2H; NHCH$_2$), 1.87 (t, J=1.1 Hz, 3H; CH$_3$).

$^{19}$F NMR (measurement solvent: deuterated chloroform, reference material: trichlorofluoromethane): δ=−114.2 (t, J=15.0 Hz, 2F).

Synthesis Example 6

5-Phenyldibenzothiophenyl 2-[(2-Methacryloyloxy)ethylcarbamoyloxy]-1,1-difluoroethanesulfonate

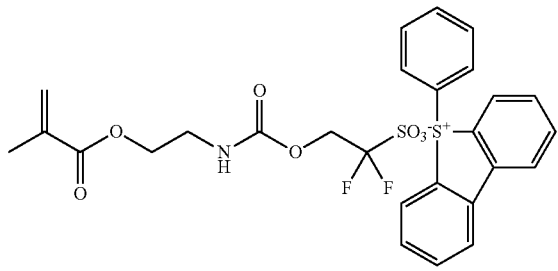

In 70 mL of acetonitrile, 15.4 g of a white solid of 5-phenyldibenzothiophenyl 2-hydroxy-1,1-difluoroethanesulfonate (purity: 97.3%, equivalent to 35.4 mol) was dissolved by stirring. The resulting solution was admixed with 0.79 g (6.4 mmol) of N,N-dimethylaminopyridine and 0.1 g of 2,2'-methylene-bis(4-methyl-6-tert-butylphenol), followed by heating the solution to 45° C. and dropping a solution of 5 g (32.2 mmol) of 2-methacryloyloxyethyl isocyanate in acetonitrile (20 mL) into the solution over about 20 minutes. After that, the solution was reacted at 45° C. over a night. To the thus-obtained reaction solution added was 80 mL of water. The reaction solution was subsequently subjected to concentration under reduced pressure to remove the acetonitrile from the reaction solution. The remaining aqueous solution was extracted with 65 mL of chloroform. The resulting organic layer was washed four times with 80 mL of water and concentrated. The concentrate was dissolved in a mixture of one time as much weight of chloroform (rich solvent) and one time as much weight of acetonitrile (rich solvent). The solution was heated to 55° C., followed by dropping three times as much weight of diisopropyl ether (poor solvent) to the solution. The solution was cooled to room temperature. The thus-formed precipitate was filtered out of the solution. The above operation was again performed on the precipitate to thereby recrystallize the precipitate. With this, 14.3 g of the target compound was obtained as a white powder (yield: 76%, purity: 90%).

Properties of 5-phenyldibenzothiophenyl 2-[(2-methacryloyloxy)ethylcarbamoyloxy]-1,1-difluoroethanesulfonate $^{1}$H NMR (measurement solvent: deuterated chloroform, reference material: tetramethylsilane): δ=8.51 (d, 2H; cation moiety), 8.36 (d, 2H; cation moiety), 8.00 (t, 2H; cation moiety), 7.77-7.56 (m, 7H; cation moiety), 6.05 (s, 1H; =CH$_2$), 5.65 (t, J=1.6 Hz, 1H; =CH$_2$), 4.48 (t, J=15.0 Hz, 2H; CF$_2$CH$_2$), 4.07 (t, J=5.4 Hz, 2H; OCH$_2$), 3.30 (q, J=5.3 Hz, 2H; NHCH$_2$), 1.85 (t, J=1.1 Hz, 3H; CH$_3$).

$^{19}$F NMR (measurement solvent: deuterated chloroform, reference material: trichlorofluoromethane): δ=−114.0 (t, J=15.0 Hz, 2F).

Synthesis Example 7

(4-Tert-butylphenyl)tetramethylenesulfide 2-[(2-Methacryloyloxy)ethylcarbamoyloxy]-1,1-difluoroethanesulfonate

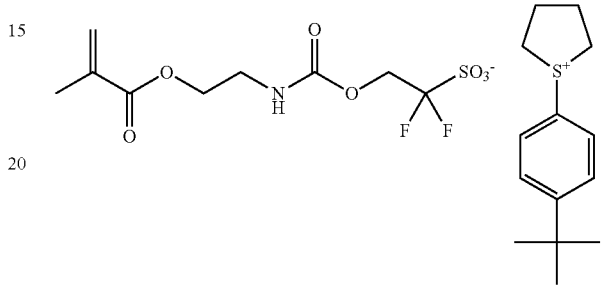

In 70 mL of acetonitrile, 15.0 g of a white solid of (4-tert-butylphenyl)tetramethylenesulfide 2-hydroxy-1,1-difluoroethanesulfonate (purity: 90.3%, equivalent to 35.4 mol) was dissolved by stirring. The resulting solution was admixed with 0.79 g (6.4 mmol) of N,N-dimethylaminopyridine and 0.1 g of 2,2'-methylene-bis(4-methyl-6-tert-butylphenol), followed by heating the solution to 45° C. and dropping a solution of 5 g (32.2 mmol) of 2-methacryloyloxyethyl isocyanate in acetonitrile (20 mL) into the solution over about 40 minutes. After that, the solution was reacted at 45° C. over a night. To the thus-obtained reaction solution added was 85 mL of water. The reaction solution was subsequently subjected to concentration under reduced pressure to remove the acetonitrile from the reaction solution. The remaining aqueous solution was extracted with 70 mL of chloroform. The resulting organic layer was purified by washing the organic layer four times with 85 mL of water, concentrating the organic layer, dissolving the concentrate in eight times as much weight of chloroform (rich solvent), and then, washing the solution five times with the same weight of diisopropyl ether (poor solvent) (liquid-liquid distribution). With this, 11.0 g of a chloroform solution of the target compound was obtained (yield: 35%, purity: 91%, target compound: 6.6 g, content rate: 60%).

Properties of (4-tert-butylphenyl)tetramethylenesulfide 2-[(2-methacryloyloxy)ethylcarbamoyloxy]-1,1-difluoroethanesulfonate $^{1}$H NMR (measurement solvent: deuterated chloroform, reference material: tetramethylsilane): δ=7.75-7.60 (m, 4H; cation moiety), 6.04 (s, 1H; =CH$_2$), 5.61 (t, J=1.6 Hz, 1H; =CH$_2$), 4.52 (t, J=15.0 Hz, 2H; CF$_2$CH$_2$), 4.03 (t, J=5.4 Hz, 2H; OCH$_2$), 3.54 (m, 2H; cation moiety), 3.36 (q, J=5.3 Hz, 2H; NHCH$_2$), 3.20 (m, 2H; cation moiety), 2.23 (m, 2H; cation moiety), 1.87 (t, J=1.1 Hz, 3H; CH$_3$), 1.32 (s, 9H; cation moiety).

$^{19}$F NMR (measurement solvent: deuterated chloroform, reference material: trichlorofluoromethane): δ=−114.7 (t, J=15.0 Hz, 2F).

Synthesis Example 8

Triphenylsulfonium 4-[(2-Methacryloyloxy)ethylcarbamoyloxy]-1,1,2,2-tetrafluorobutanesulfonate

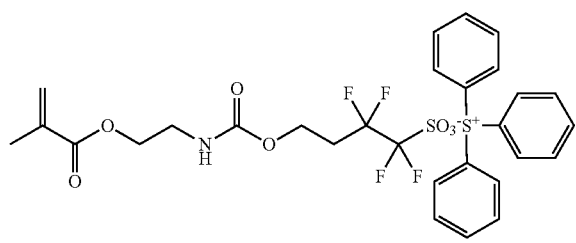

In 70 mL of acetonitrile, 17.7 g of a white solid of triphenylsulfonium 4-hydroxy-1,1,2,2-tetrafluorobutanesulfonate (purity: 97.5%, equivalent to 35.3 mol) was dissolved by stirring. The resulting solution was admixed with 0.79 g (6.4 mmol) of N,N-dimethylaminopyridine and 0.1 g of 2,2'-methylene-bis(4-methyl-6-tert-butylphenol), followed by heating the solution to 45° C. and dropping a solution of 5 g (32.2 mmol) of 2-methacryloyloxyethyl isocyanate in acetonitrile (15 mL) into the solution over about 20 minutes. After that, the solution was reacted at 45° C. over a night. To the thus-obtained reaction solution added was 90 mL of water. The reaction solution was subsequently subjected to concentration under reduced pressure to remove the acetonitrile from the reaction solution. The remaining aqueous solution was extracted with 90 mL of chloroform. The resulting organic layer was purified by washing the organic layer four times with 90 mL of water, concentrating the organic layer, dissolving the concentrate in eight times as much weight of chloroform (rich solvent), and then, washing the solution five times with the same weight of diisopropyl ether (poor solvent) (liquid-liquid distribution). With this, 16.1 g of a chloroform solution of the target compound was obtained (yield: 42%, purity: 90%, target compound: 9.7 g, content rate: 60%).

Properties of triphenylsulfonium 4-[(2-methacryloyloxy)ethylcarbamoyloxy]-1,1,2,2-tetrafluorobutanesulfonate $^1$H NMR (measurement solvent: deuterated chloroform, reference material: tetramethylsilane): δ=7.75-7.60 (m, 15H; cation moiety), 6.07 (s, 1H; =CH$_2$), 554 (t, J=1.6 Hz, 1H; =CH$_2$), 4.32 (m, 2H; CF$_2$CH$_2$), 4.13 (t, J=5.4 Hz, 2H; OCH$_2$), 4.06 (m, 2H; NHCOOCH$_2$), 3.36 (q, J=5.3 Hz, 2H; NHCH$_2$), 1.87 (t, J=1.1 Hz, 3H; CH$_3$).

$^{19}$F NMR (measurement solvent: deuterated chloroform, reference material: trichlorofluoromethane): δ=−112.9 (s, 2F), −118.8 (s, 2F).

Synthesis Example 9

2,5-Dioxo-1-pyrrolidinyl 1,1-Difluoro-2-hydroxyethanesulfonate

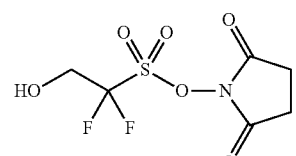

In 100 mL of acetonitrile, 25.5 g of a liquid of 2-hydroxy-1,1-difluoroethanesulfonyl chloride (purity: 98%, equivalent to 0.138 mol) was dissolved by stirring. The resulting solution was cooled to 0° C., admixed with 14.0 g (0.166 mol) of sodium hydrogencarbonate and 17.5 g (0.152 mol) of N-hydroxysuccinimide, and then, reacted at 0° C. for 24 hours. To the thus-obtained reaction solution, 125 mL of water was added. The reaction solution was subsequently extracted twice with 100 mL of ethyl acetate. The resulting organic layer was washed twice with 100 mL of water. The organic layer was further subjected to concentration and purified by distillation. With this, 20.7 g of the target compound was obtained as a colorless oily substance (yield: 52%, purity: 90%, pure content: 18.7 g).

Properties of 2,5-dioxo-1-pyrrolidinyl 1,1-difluoro-2-hydroxyethanesulfonate $^1$H NMR (measurement solvent: deuterated chloroform, reference material: tetramethylsilane): δ=4.13 (t, J=12.4 Hz, 2H; HOCH$_2$), 2.79 (s, 4H; CH$_2$CO).

$^{19}$F NMR (measurement solvent: deuterated chloroform, reference material: trichlorofluoromethane): δ=−103.3 (t, J=13.0 Hz, 2F).

Synthesis Example 10

2,5-Dioxo-1-pyrrolidinyl 1,1-Difluoro-2-[(2-methacryloyloxy)ethylcarbamoyloxy]ethanesulfonate

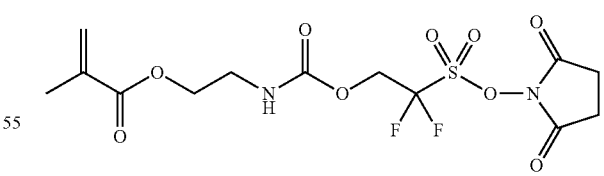

In 120 mL of acetonitrile, 20.7 g of an oily substance of 2,5-dioxo-1-pyrrolidinyl 1,1-difluoro-2-hydroxyethanesulfonate (purity: 90%, equivalent to 72.2 mol) was dissolved by stirring. The resulting solution was admixed with 0.238 g (1.97 mmol) of N,N-dimethylaminopyridine and 0.1 g of 2,2'-methylene-bis(4-methyl-6-tert-butylphenol), followed by heating the solution to 45° C. and dropping a solution of 10.2 g (65.6 mmol) of 2-methacryloyloxyethyl isocyanate in acetonitrile (30 mL) into the solution over about 20 minutes.

After that, the solution was reacted at 45° C. over a night. To the thus-obtained reaction solution, 100 mL of water was added. The reaction solution was subsequently subjected to concentration under reduced pressure to remove the acetonitrile from the reaction solution. The remaining aqueous solution was extracted twice with 100 mL of ethyl acetate. The resulting organic layer was washed four times with 100 mL of water and purified by performing three cycles of concentrating the organic layer, dissolving the concentration residue in 200 mL of diisopropyl ether, precipitating a solid substance out of the solution to yield a supernatant liquid, and then, subjecting the supernatant liquid to solvent concentration. With this, 18.1 g of the target compound was obtained as a pale yellow oily substance (yield: 65%, purity: 98%, pure content: 17.7 g).

Properties of 2,5-dioxo-1-pyrrolidinyl 1,1-difluoro-2-[(2-methacryloyloxy)ethylcarbamoyloxy]ethanesulfonate $^1$H NMR (measurement solvent: deuterated chloroform, reference material: tetramethylsilane): δ=6.09 (s, 1H; =CH$_2$), 5.55 (t, J=1.6 Hz, 1H; =CH$_2$), 4.86 (t, J=15.0 Hz, 2H; CF$_2$CH$_2$), 4.17 (t, J=5.4 Hz, 2H; OCH$_2$), 3.47 (q, J=5.3 Hz, 2H; NHCH$_2$), 2.85 (s, 4H; CH$_2$CO), 1.89 (t, J=1.1 Hz, 3H; CH$_3$).

$^{19}$F NMR (measurement solvent: deuterated chloroform, reference material: trichlorofluoromethane): δ=−102.2 (t, J=15.0 Hz, 2F).

Synthesis Example 11

2,5-Dioxo-1-pyrrolidinyl 1,1,2,2-Tetrafluoro-4-hydroxybutanesulfonate

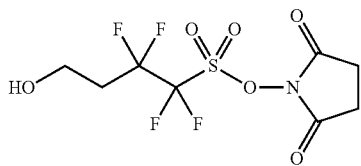 [SMILES: O=C1CCC(=O)N1OS(=O)(=O)C(F)(F)C(F)(F)CCO]

In 100 mL of acetonitrile, 25 g of a liquid of 1,1,2,2-tetrafluoro-4-hydroxybutanesulfonyl chloride (purity: 90%, equivalent to 0.102 mol) was dissolved by stirring. The resulting solution was cooled to 0° C., admixed with 10.3 g (0.123 mol) of sodium hydrogencarbonate and 12.9 g (0.112 mol) of N-hydroxysuccinimide, and then, reacted at 0° C. for 24 hours. To the thus-obtained reaction solution, 125 mL of water was added. The reaction solution was subsequently extracted twice with 100 mL of ethyl acetate. The resulting organic layer was washed twice with 100 mL of water and subjected to concentration. With this, 23.4 g of the target compound was obtained as a pale yellow oily substance (yield: 56%, purity: 79%, pure content: 18.5 g).

Properties of 2,5-dioxo-1-pyrrolidinyl 1,1,2,2-tetrafluoro-4-hydroxybutanesulfonate $^1$H NMR (measurement solvent: deuterated chloroform, reference material: tetramethylsilane): δ=3.96 (t, J=6.6 Hz, 2H; OCH$_2$), 2.88 (s, 4H; CH$_2$CO), 2.59 (tt, J=19.6 Hz, 6.6 Hz, 2H; CH$_2$F$_2$).

$^{19}$F NMR (measurement solvent: deuterated chloroform, reference material: trichlorofluoromethane): δ=−108.7 (s, 2F), −110.7 (m, 2F).

Synthesis Example 12

2,5-Dioxo-1-pyrrolidinyl 1,1,2,2-Tetrafluoro-4-[(2-methacryloyloxy)ethylcarbamoyloxy]butanesulfonate

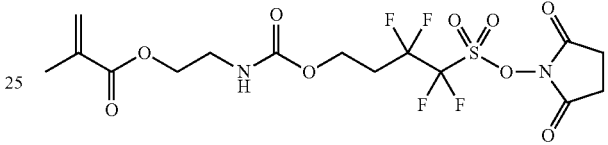

In 96 mL of acetonitrile, 23.4 g of an oily substance of 2,5-dioxo-1-pyrrolidinyl 1,1,2,2-tetrafluoro-4-hydroxybutanesulfonate (purity: 79%, equivalent to 57.2 mmol) was dissolved by stirring. The resulting solution was admixed with 0.208 g (1.72 mmol) of N,N-dimethylaminopyridine and 0.08 g of 2,2'-methylene-bis(4-methyl-6-tert-butylphenol), followed by heating the solution to 45° C. and dropping a solution of 8.07 g (52.0 mmol) of 2-methacryloyloxyethyl isocyanate in acetonitrile (24 mL) into the solution over about 20 minutes. After that, the solution was reacted at 45° C. over a night. To the thus-obtained reaction solution, 80 mL of water was added. The reaction solution was subsequently subjected to concentration under reduced pressure to remove the acetonitrile from the reaction solution. The remaining aqueous solution was extracted twice with 80 mL of ethyl acetate. The resulting organic layer was washed four times with 80 mL of water and purified by performing three cycles of concentrating the organic layer, dissolving the concentration residue in 160 mL of diisopropyl ether, precipitating a solid substance out of the solution to yield a supernant liquid, and then, subjecting the supernatant liquid to solvent concentration. With this, 17.4 g of the target compound was obtained as a pale yellow oily substance (yield: 68%, purity: 97%, pure content: 16.9 g).

Properties of 2,5-dioxo-1-pyrrolidinyl 1,1,2,2-tetrafluoro-4-[(2-methacryloyloxy)ethylcarbamoyloxy]butanesulfonate $^1$H NMR (measurement solvent: deuterated chloroform, reference material: tetramethylsilane): δ=6.08 (s, 1H; =CH$_2$), 5.54 (t, J=1.6 Hz, 1H; =CH$_2$), 4.36 (t, J=15.0 Hz, 2H; NHCO$_2$CH$_2$), 4.17 (t, J=5.4 Hz, 2H; NHCH$_2$), 2.89 (s, 4H; CH$_2$CO), 2.74 (tt, J=19.6 Hz, 6.6 Hz, 2H, CH$_2$CF$_2$), 1.88 (t, J=1.1 Hz, 3H; CH$_3$).

Synthesis Example 13

1,3-Dihydro-1,3-dioxo-2H-isoindole-2-yl 1,1-Difluoro-2-hydroxyethanesulfonate

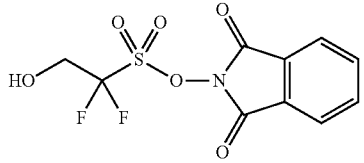 [SMILES: O=C1c2ccccc2C(=O)N1OS(=O)(=O)C(F)(F)CO]

In 100 mL of acetonitrile, 25.5 g of a liquid of 2-hydroxy-1,1-difluoroethanesulfonyl chloride (purity: 98%, equivalent to 0.138 mol) was dissolved by stirring. The resulting solution was cooled to 0° C., admixed with 14.0 g (0.166 mol) of sodium hydrogencarbonate and 24.8 g (0.152 mol) of N-hydroxyphthalimide, and then, reacted at 0° C. for 24 hours. To the thus-obtained reaction solution, 125 mL of water was added. The reaction solution was subsequently extracted twice with 100 mL of ethyl acetate. The resulting organic layer was washed twice with 100 mL of water and subjected to concentration. The concentration residue was admixed with 75 mL of ethyl acetate, followed by heating the solution at 60° C. to dissolve the solid substance. Then, 150 mL of heptane was dropped into the solution. The solution was gradually cooled to 0° C. to precipitate a crystalline out of the solution. The crystalline precipitate was filtered out and dried. With this, 23.2 g of the target compound was obtained as a white solid (yield: 53%, purity: 97%, pure content: 22.5 g).

Properties of 1,3-dihydro-1,3-dioxo-2H-isoindole-2-yl 1,1-difluoro-2-hydroxyethanesulfonate $^1$H NMR (measurement solvent: deuterated chloroform, reference material: tetramethylsilane): δ=7.95 (s, 4H; aromatic ring), 4.17 (t, J=12.4 Hz, 2H; HOCH$_2$).

$^{19}$F NMR (measurement solvent: deuterated chloroform, reference material: trichlorofluoromethane): δ=−102.4 (t, J=13.0 Hz, 2F).

Synthesis Example 14

1,3-Dihydro-1,3-dioxo-2H-isoindole-2-yl 1,1-Difluoro-2-[(2-methacryloyloxy)ethylcarbamoyloxy]ethanesulfonate

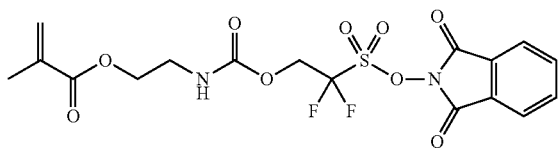 [SMILES: C=C(C)C(=O)OCCNC(=O)OCC(F)(F)S(=O)(=O)ON1C(=O)c2ccccc2C1=O]

In 120 mL of acetonitrile, 23.2 g of a white solid of 1,3-dihydro-1,3-dioxo-2H-isoindole-2-yl 1,1-difluoro-2-hydroxyethanesulfonate (purity: 97%, equivalent to 73.4 mmol) was dissolved by stirring. The resulting solution was admixed with 0.243 g (2.00 mmol) of N,N-dimethylaminopyridine and 0.1 g of 2,2'-methylene-bis(4-methyl-6-tert-butylphenol), followed by heating the solution to 45° C. and dropping a solution of 10.4 g (66.7 mmol) of 2-methacryloyloxyethyl isocyanate in acetonitrile (30 mL) into the solution over about 20 minutes. After that, the solution was reacted at 45° C. over a night. To the thus-obtained reaction solution, 100 mL of water was added. The reaction solution was subsequently subjected to concentration under reduced pressure to remove the acetonitrile from the reaction solution. The remaining aqueous solution was extracted twice with 100 mL of ethyl acetate. The resulting organic layer was washed four times with 80 mL of water and subjected to concentration. The concentration residue was admixed with 60 mL of ethyl acetate, followed by heating the solution at 60° C. to dissolve the solid substance. Then, 180 mL of heptane was dropped into the solution. The solution was gradually cooled to 0° C. to precipitate a crystalline out of the solution. The crystalline precipitate was filtered out and dried. With this, 22.0 g of the target compound was obtained as a white solid (yield: 70%, purity: 98%, pure content: 21.6 g).

Properties of 1,3-dihydro-1,3-dioxo-2H-isoindole-2-yl 1,1-difluoro-2-[(2-methacryloyloxy)ethylcarbamoyloxy]ethanesulfonate $^1$H NMR (measurement solvent: deuterated chloroform, reference material: tetramethylsilane): δ=7.97 (s, 4H; aromatic ring), 6.09 (s, 1H; =CH$_2$), 5.56 (t, J=1.6 Hz, 1H; =CH$_2$), 4.88 (t, J=15.0 Hz, 2H; CF$_2$CH$_2$).

$^{19}$F NMR (measurement solvent: deuterated chloroform, reference material: trichlorofluoromethane): δ=−102.0 (t, J=15.0 Hz, 2F).

Synthesis Example 15

1,3-Dihydro-1,3-dioxo-2H-isoindole-2-yl 1,1,2,2-Tetrafluoro-4-hydroxybutanesulfonate

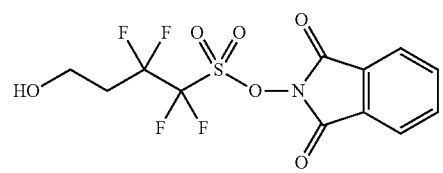 [SMILES: O=C1c2ccccc2C(=O)N1OS(=O)(=O)C(F)(F)C(F)(F)CCO]

In 100 mL of acetonitrile, 25 g of a liquid of 1,1,2,2-tetrafluoro-4-hydroxybutanesulfonyl chloride (purity: 99%, equivalent to 0.102 mol) was dissolved by stirring. The resulting solution was cooled to 0° C., admixed with 10.3 g (0.123 mol) of sodium hydrogencarbonate and 18.3 g (0.112 mol) of N-hydroxyphthalimide, and then, reacted at 0° C. for 24 hours. To the thus-obtained reaction solution, 125 mL of water was added. The reaction solution was subsequently extracted twice with 100 mL of ethyl acetate. The resulting organic layer was washed twice with 100 mL of water and subjected to concentration. With this, 26.4 g of the target compound was obtained as a pale yellow solid (yield: 57%, purity: 82%, pure content: 21.6 g).

Properties of 1,3-dihydro-1,3-dioxo-2H-isoindole-2-yl 1,1,2,2-tetrafluoro-4-hydroxybutanesulfonate $^1$H NMR (measurement solvent: deuterated chloroform, reference material: tetramethylsilane): δ=7.97 (s, 4H; aromatic ring), 3.98 (t, J=12.4 Hz, 2H; HOCH$_2$), 2.60 (tt, J=19.6 Hz, 6.6 Hz, 2H; CH$_2$CF$_2$.

<sup>19</sup>F NMR (measurement solvent: deuterated chloroform, reference material: trichlorofluoromethane): δ=−108.4 (s, 2F), −110.5 (m, 2F).

Synthesis Example 16

1,3-Dihydro-1,3-dioxo-2H-isoindole-2-yl 1,1,2,2-Tetrafluoro-4-[(2-methacryloyloxy)ethylcarbamoyloxy]butanesulfonate

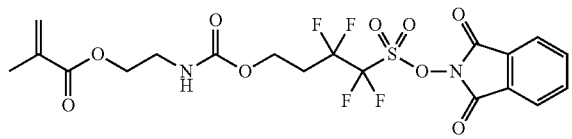 [SMILES: C=C(C)C(=O)OCCNC(=O)OCCC(F)(F)C(F)(F)S(=O)(=O)ON1C(=O)c2ccccc2C1=O]

In 96 mL of acetonitrile, 26.4 g of a pale yellow solid of 1,3-dihydro-1,3-dioxo-2H-isoindole-2-yl-1,1,2,2-tetrafluoro-4-hydroxybutanesulfonate (purity: 82%, equivalent to 58.3 mmol) was dissolved by stirring. The resulting solution was admixed with 0.193 g (1.59 mmol) of N,N-dimethylaminopyridine and 0.08 g of 2,2'-methylene-bis(4-methyl-6-tert-butylphenol), followed by heating the solution to 45° C. and dropping a solution of 8.22 g (53.0 mmol) of 2-methacryloyloxyethyl isocyanate in acetonitrile (24 mL) into the solution over about 20 minutes. After that, the solution was reacted at 45° C. over a night. To the thus-obtained reaction solution, 80 mL of water was added. The reaction solution was subsequently subjected to concentration under reduced pressure to remove the acetonitrile from the reaction solution. The remaining aqueous solution was extracted twice with 80 mL of ethyl acetate. The resulting organic layer was washed four times with 80 mL of water and subjected to concentration. The concentration residue was admixed with 60 mL of ethyl acetate, followed by heating the solution at 60° C. to dissolve the solid substance. Then, 180 mL of heptane was dropped into the solution. The solution was gradually cooled to 0° C. to precipitate a crystalline out of the solution. The crystalline precipitate was filtered out and dried. With this, 19.0 g of the target compound was obtained as a white solid (yield: 67%, purity: 98%, pure content: 18.6 g).

Properties of 1,3-dihydro-1,3-dioxo-2H-isoindole-2-yl 1,1,2,2-tetrafluoro-4-[(2-methacryloyloxy)ethylcarbamoyloxy]butanesulfonate <sup>1</sup>H NMR (measurement solvent: deuterated chloroform, reference material: tetramethylsilane): δ=7.98 (s, 4H; aromatic ring), 6.09 (s, 1H; =CH<sub>2</sub>), 5.54 (t, J=1.6 Hz, 1H; =CH<sub>2</sub>), 4.37 (t, J=15.0 Hz, 2H; NHCO<sub>2</sub>CH<sub>2</sub>), 4.17 (t, J=5.4 Hz, 2H; CH<sub>2</sub>=C(CH<sub>3</sub>)CCO<sub>2</sub>CH<sub>2</sub>), 3.46 (q, J=5.3 Hz, 2H; NHCH<sub>2</sub>), 2.74 (tt, J=19.6 Hz, 6.6 Hz, 2H; CH<sub>2</sub>CF<sub>2</sub>), 1.88 (t, J=1.1 Hz, 3H; CH<sub>3</sub>).

<sup>19</sup>F NMR (measurement solvent: deuterated chloroform, reference material: trichlorofluoromethane): δ=−107.6 (s, 2F), −109.6 (m, 2F).

[Production of Resins]

The structures and abbreviations of the compounds used in the following polymerization examples, working examples and comparative examples are indicated below.

(PAG-1)

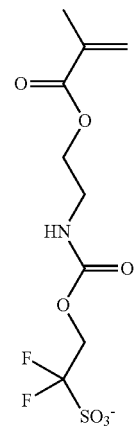
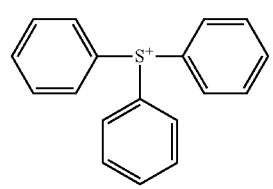

(PAG-2)

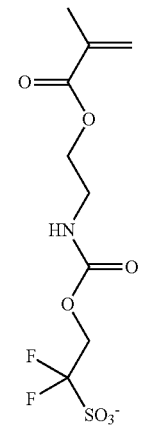
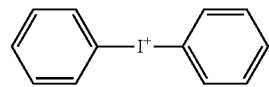

(PAG-C1)

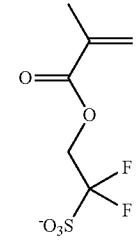
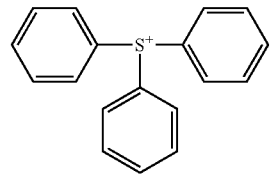

(PAG-C2)
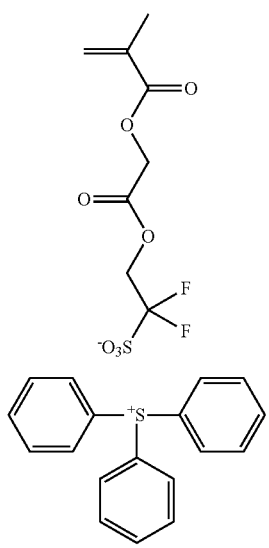
(PAG-3)
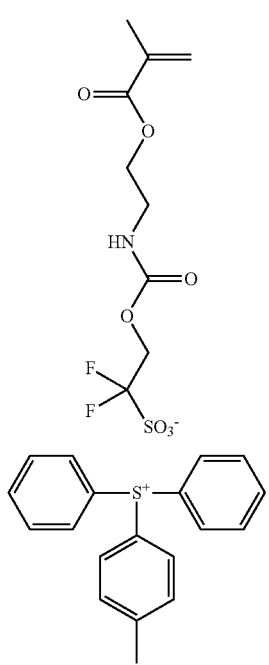
(PAG-4)
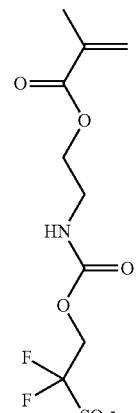
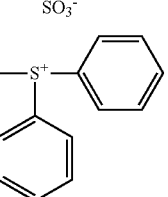
(PAG-5)
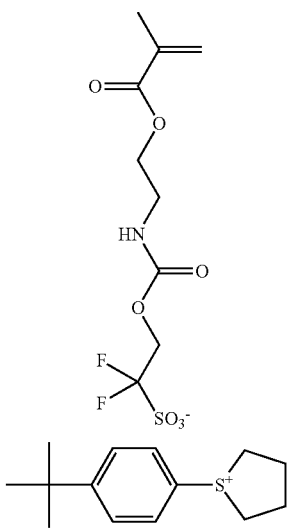

(PAG-6)
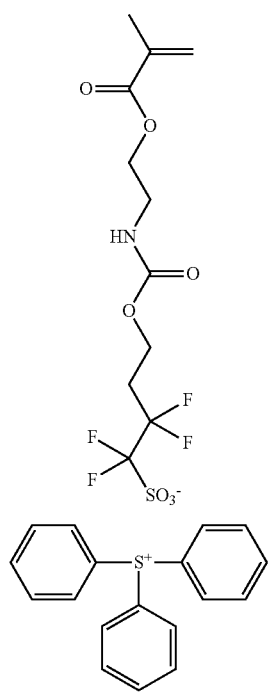
(PAG-7)
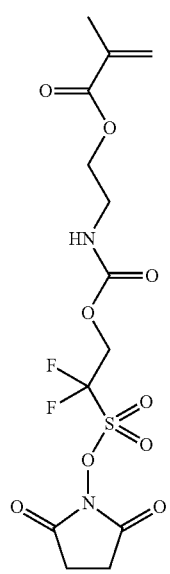
(PAG-8)
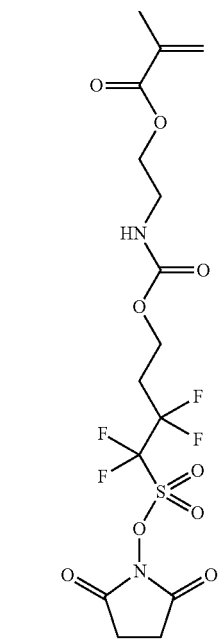
(A-1)
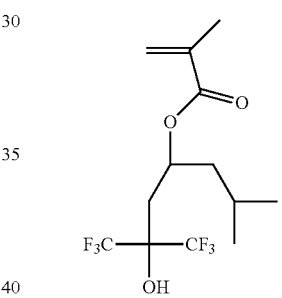
(A-2)
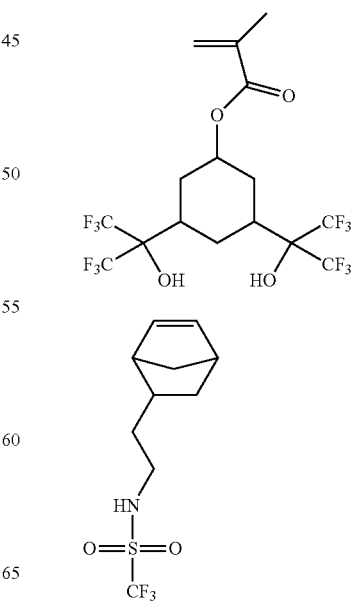
(A-3)

(A-4) 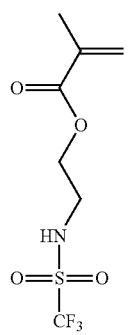
(A-5) 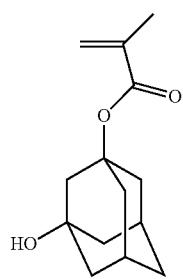
(A-6) 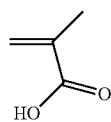
(B-1) 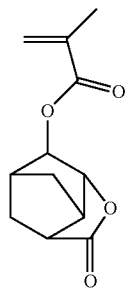
(B-2) 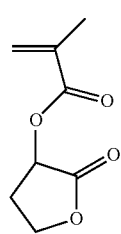
(C-1) 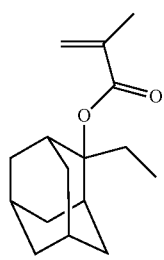
(C-2) 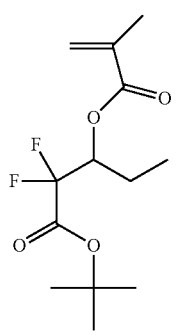
(D-1) 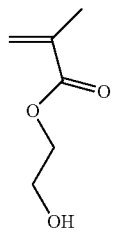
Polymerization Example P-1
[PAG-1]
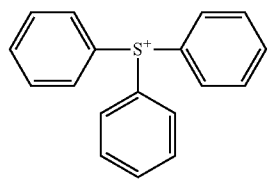
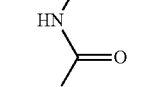
[B-1]
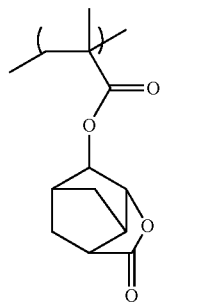

-continued

[C-1]

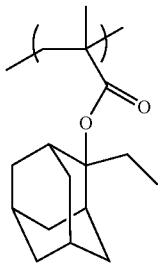

A monomer solution was prepared by dissolving 30.0 g (15 mol %) of compound (PAG-1), 34.5 g (45 mol %) of compound (B-1) and 34.3 g (40 mol %) of compound (C-1) in 300 g of 2-butanone and adding thereto 3.40 g of dimethyl 2,2'-azobis(2-methylpropionate). On the other hand, a 1000-ml three-neck flask was charged with 100 g of 2-butanone, purged with nitrogen for 30 minutes and heated to 80° C. while stirring the content of the flask. The previously prepared monomer solution was dropped into the flask by means of a dropping funnel over 3 hours. The polymerization was performed for 6 hours, assuming the initiation of the dropping as a polymerization initiation time. After the completion of the polymerization, the polymerization solution was cooled by water to about 25° C. and put into 2 kg of methanol to precipitate a white powdery substance. The white powdery substance was filtered out of the solution, washed twice with 400 g of methanol in slurry form, filtered, and then, dried at 50° C. for 15 hours. With this, a polymer was obtained as a white powder (83.2 g). The mass-average molecular weight (Mw) of the polymer was 8,500. Further, it was confirmed by $^{13}$C-NMR analysis that the polymer was in the form of a copolymer having repeating units derived from the compounds (PAG-1), (B-1) and (C-1) at a content ratio of 14.1:45.6:40.3 (mol %). The thus-obtained copolymer was named as "Resin (P-1)".

Polymerization Example P-2

[PAG-2]

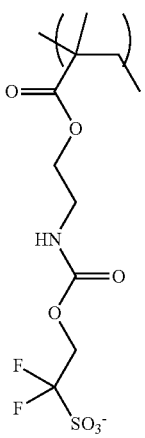
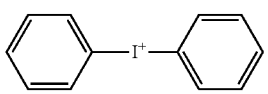

-continued

[B-1]

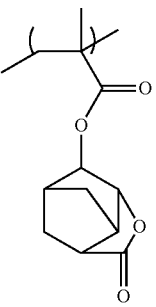

[C-1]

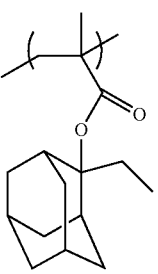

A monomer solution was prepared by dissolving 30.0 g (15 mol %) of compound (PAG-2), 33.5 g (45 mol %) of compound (B-1) and 33.3 g (40 mol %) of compound (C-1) in 300 g of 2-butanone and adding thereto 3.40 g of dimethyl 2,2'-azobis(2-methylpropionate). On the other hand, a 1000-ml three-neck flask was charged with 100 g of 2-butanone, purged with nitrogen for 30 minutes and heated to 80° C. while stirring the content of the flask. The previously prepared monomer solution was dropped into the flask by means of a dropping funnel over 3 hours. The polymerization was performed for 6 hours, assuming the initiation of the dropping as a polymerization initiation time. After the completion of the polymerization, the polymerization solution was cooled by water to about 25° C. and put into 2 kg of methanol to precipitate a white powdery substance. The white powdery substance was filtered out of the solution, washed twice with 400 g of methanol in slurry form, filtered, and then, dried at 50° C. for 18 hours. With this, a polymer was obtained as a white powder (79.3 g). The mass-average molecular weight (Mw) of the polymer was 8,900. Further, it was confirmed by $^{13}$C-NMR analysis that the polymer was in the form of a copolymer having repeating units derived from the compounds (PAG-2), (B-1) and (C-1) at a content ratio of 15.5:44.5:40.0 (mol %). The thus-obtained copolymer was named as "Resin P-2".

Polymerization Examples P-3 to P-25, X-1 to X-10, N-1 to N-10 and PG-1 to PG-9

Resins (P-3 to P-25, X-1 to X-10, N-1 to N-10 and PG-1 to PG-9) were produced in the same manner as in Polymerization Example P-1 or P-2.

The kinds and contents of the copolymerization monomers, the mole ratio of the repeating units derived from the respective monomers and the mass-average molecular weight (Mw) of the produced resins are indicated in TABLES 1 and 2.

TABLE 1

| Polymerization Example Resin | Raw material composition | | | | | | | |
|---|---|---|---|---|---|---|---|---|
| | Monomer 1 | | Monomer 2 | | Monomer 3 | | Monomer 4 | |
| | Kind | mol % | Kind | mol % | Kind | mol % | Kind | mol % |
| P-1  | PAG-1 | 15 | —   | —  | B-1 | 45 | C-1 | 40 |
| P-2  | PAG-2 | 15 | —   | —  | B-1 | 45 | C-1 | 40 |
| P-3  | PAG-1 | 15 | A-1 | 20 | B-1 | 35 | C-1 | 30 |
| P-4  | PAG-1 | 15 | A-2 | 15 | B-1 | 35 | C-1 | 35 |
| P-5  | PAG-1 | 15 | A-3 | 5  | B-1 | 35 | C-1 | 45 |
| P-6  | PAG-1 | 15 | A-4 | 20 | B-1 | 35 | C-1 | 30 |
| P-7  | PAG-2 | 15 | A-1 | 20 | B-1 | 35 | C-1 | 30 |
| P-8  | PAG-2 | 15 | A-2 | 15 | B-1 | 35 | C-1 | 35 |
| P-9  | PAG-2 | 15 | A-3 | 5  | B-1 | 35 | C-1 | 45 |
| P-10 | PAG-2 | 15 | A-4 | 20 | B-1 | 35 | C-1 | 30 |
| P-11 | PAG-1 | 20 | A-5 | 30 | —   | —  | C-1 | 50 |
| P-12 | PAG-1 | 20 | A-5 | 25 | B-1 | 25 | C-1 | 30 |
| P-13 | PAG-2 | 15 | A-5 | 25 | B-1 | 25 | C-1 | 35 |
| P-14 | PAG-1 | 15 | A-5 | 25 | B-2 | 30 | C-1 | 30 |
| P-15 | PAG-1 | 20 | A-5 | 20 | B-2 | 30 | C-2 | 30 |
| P-16 | PAG-1 | 5  | —   | —  | B-1 | 50 | C-1 | 45 |
| P-17 | PAG-2 | 5  | A-2 | —  | B-1 | 50 | C-1 | 45 |
| P-18 | PAG-3 | 15 | A-1 | 20 | B-1 | 30 | C-1 | 35 |
| P-19 | PAG-4 | 15 | A-1 | 20 | B-1 | 30 | C-1 | 35 |
| P-20 | PAG-5 | 15 | A-2 | 20 | B-1 | 30 | C-1 | 35 |
| P-21 | PAG-6 | 15 | A-2 | 20 | B-1 | 30 | C-1 | 35 |
| P-22 | PAG-7 | 20 | A-1 | 20 | B-1 | 30 | C-1 | 30 |
| P-23 | PAG-7 | 20 | A-2 | 20 | B-1 | 30 | C-1 | 30 |
| P-24 | PAG-8 | 20 | A-1 | 20 | B-1 | 30 | C-1 | 30 |
| P-25 | PAG-8 | 20 | A-2 | 20 | B-1 | 30 | C-1 | 30 |

| Polymerization Example Resin | Mole ratio of repeating units in resin | | | | Molecular weight Mw |
|---|---|---|---|---|---|
| | Monomer 1 | Monomer 2 | Monomer 3 | Monomer 4 | |
| P-1  | 14 | —  | 46 | 40 | 8,500 |
| P-2  | 15 | —  | 45 | 40 | 8,900 |
| P-3  | 14 | 18 | 37 | 31 | 8,600 |
| P-4  | 14 | 14 | 36 | 36 | 8,300 |
| P-5  | 15 | 4  | 37 | 44 | 7,800 |
| P-6  | 14 | 19 | 37 | 30 | 8,100 |
| P-7  | 14 | 18 | 36 | 32 | 8,500 |
| P-8  | 14 | 14 | 35 | 37 | 8,300 |
| P-9  | 15 | 5  | 37 | 43 | 7,600 |
| P-10 | 14 | 19 | 36 | 31 | 7,900 |
| P-11 | 17 | 29 | —  | 54 | 9,600 |
| P-12 | 19 | 25 | 27 | 29 | 7,400 |
| P-13 | 14 | 24 | 28 | 34 | 9,300 |
| P-14 | 14 | 25 | 32 | 29 | 9,700 |
| P-15 | 18 | 20 | 33 | 29 | 8,100 |
| P-16 | 4  | —  | 54 | 44 | 7,100 |
| P-17 | 4  | —  | 53 | 43 | 6,800 |
| P-18 | 14 | 21 | 32 | 33 | 8,200 |
| P-19 | 13 | 22 | 31 | 34 | 9,300 |
| P-20 | 16 | 19 | 29 | 36 | 8,800 |
| P-21 | 15 | 23 | 30 | 32 | 7,900 |
| P-22 | 19 | 19 | 32 | 30 | 9,000 |
| P-23 | 18 | 18 | 32 | 32 | 9,200 |
| P-24 | 17 | 19 | 32 | 32 | 9,100 |
| P-25 | 18 | 18 | 32 | 32 | 9,300 |

Monomer 1: Polymrizable fluorine-containing sulfonic acid onium salt
Monomer 2, 3: Auxiliary monomer
Monomer 4: monomr ontaining acid labile group or cross-linking site

TABLE 2

| Polymerization Example Resin | Raw material composition | | | | | | | |
|---|---|---|---|---|---|---|---|---|
| | Monomer 1 | | Monomer 2 | | Monomer 3 | | Monomer 4 | |
| | Kind | mol % | Kind | mol % | Kind | mol % | Kind | mol % |
| X-1 | PAG-1 | 100 | —   | —  | — | — | — | — |
| X-2 | PAG-2 | 100 | —   | —  | — | — | — | — |
| X-3 | PAG-1 | 30  | A-1 | 70 | — | — | — | — |

TABLE 2-continued

| | | | | | | | | |
|---|---|---|---|---|---|---|---|---|
| X-4 | PAG-1 | 5 | A-2 | 50 | B-1 | 45 | — | — |
| N-1 | PAG-1 | 15 | — | — | B-1 | 10 | A-6 | 40 |
| | | | | | | | D-1 | 35 |
| N-2 | PAG-2 | 15 | A-1 | 60 | B-2 | 5 | A-5 | 20 |
| N-3 | PAG-1 | 15 | A-1 | 20 | A-2 | 40 | D-1 | 25 |
| N-4 | PAG-2 | 15 | — | — | A-2 | 50 | A-5 | 35 |
| PG-1 | PAG-1 | 10 | B-1 | 40 | C-1 | 40 | PAG-C1 | 10 |
| PG-2 | PAG-1 | 10 | B-1 | 40 | C-1 | 40 | PAG-C2 | 10 |
| X-5 | PAG-3 | 10 | A-2 | 50 | B-1 | 40 | — | — |
| X-6 | PAG-4 | 10 | A-2 | 50 | B-1 | 40 | — | — |
| X-7 | PAG-5 | 10 | A-1 | 50 | B-1 | 40 | — | — |
| X-8 | PAG-6 | 10 | A-2 | 50 | B-1 | 40 | — | — |
| N-5 | PAG-3 | 15 | A-1 | 20 | B-1 | 40 | D-1 | 25 |
| N-6 | PAG-4 | 15 | A-1 | 20 | B-1 | 40 | D-1 | 25 |
| N-7 | PAG-5 | 15 | — | — | B-1 | 60 | A-5 | 25 |
| N-8 | PAG-6 | 15 | — | — | B-1 | 60 | A-5 | 25 |
| PG-3 | PAG-3 | 10 | B-1 | 40 | C-1 | 40 | PAG-C2 | 10 |
| PG-4 | PAG-4 | 10 | B-1 | 40 | C-1 | 40 | PAG-C1 | 10 |
| PG-5 | PAG-5 | 10 | B-1 | 40 | C-1 | 40 | PAG-C1 | 10 |
| PG-6 | PAG-6 | 10 | B-1 | 40 | C-1 | 40 | PAG-C2 | 10 |
| X-9 | PAG-7 | 20 | A-1 | 40 | B-1 | 40 | — | — |
| X-10 | PAG-8 | 20 | A-1 | 40 | B-1 | 40 | — | — |
| N-9 | PAG-7 | 20 | A-1 | 20 | B-1 | 40 | D-1 | 20 |
| N-10 | PAG-8 | 20 | A-1 | 20 | B-1 | 40 | A-5 | 20 |
| PG-7 | PAG-7 | 15 | B-1 | 35 | C-1 | 40 | PAG-C1 | 10 |
| PG-8 | PAG-8 | 15 | B-1 | 35 | C-1 | 40 | PAG-C2 | 10 |
| PG-9 | PAG-1 | 15 | B-1 | 35 | C-1 | 40 | PAG-7 | 10 |

| Polymerization Example Resin | Mole ratio of repeating units in resin | | | | Molecular weight Mw |
|---|---|---|---|---|---|
| | Monomer 1 | Monomer 2 | Monomer 3 | Monomer 4 | |
| X-1 | 100 | — | — | — | 6,900 |
| X-2 | 100 | — | — | — | 6,100 |
| X-3 | 29 | 71 | — | — | 8,900 |
| X-4 | 5 | 53 | 42 | — | 9,100 |
| N-1 | 15 | — | 9 | 39 | 8,800 |
| | | | | 37 | |
| N-2 | 15 | 62 | 5 | 18 | 8,500 |
| N-3 | 15 | 21 | 41 | 23 | 7,200 |
| N-4 | 14 | — | 53 | 33 | 9,900 |
| PG-1 | 9 | 39 | 44 | 8 | 9,600 |
| PG-2 | 8 | 38 | 45 | 9 | 9,000 |
| X-5 | 8 | 52 | 40 | — | 7,800 |
| X-6 | 9 | 51 | 40 | — | 7,200 |
| X-7 | 9 | 53 | 38 | — | 8,400 |
| X-8 | 8 | 50 | 42 | — | 7,500 |
| N-5 | 15 | 22 | 41 | 22 | 9,300 |
| N-6 | 15 | 21 | 43 | 21 | 9,100 |
| N-7 | 14 | — | 62 | 24 | 8,300 |
| N-8 | 14 | — | 60 | 26 | 9,700 |
| PG-3 | 8 | 39 | 44 | 9 | 9,400 |
| PG-4 | 8 | 38 | 46 | 8 | 8,700 |
| PG-5 | 9 | 41 | 42 | 8 | 9,100 |
| PG-6 | 9 | 40 | 42 | 9 | 8,900 |
| X-9 | 17 | 41 | 42 | — | 8,600 |
| X-10 | 18 | 40 | 42 | — | 9,000 |
| N-9 | 17 | 19 | 43 | 21 | 9,400 |
| N-10 | 18 | 18 | 42 | 22 | 9,600 |
| PG-7 | 14 | 36 | 42 | 8 | 9,500 |
| PG-8 | 13 | 37 | 42 | 8 | 9,800 |
| PG-9 | 15 | 36 | 41 | 9 | 9,900 |

Monomer 1: Polymrizable fluorine-containing sulfonic acid onium salt
Monomer 2, 3: Auxiliary monomer
Monomer 4: monomr ontaining acid labile group or cross-linking site

Examples 1 to 53

Preparation of Resist Compositions

Resist compositions were each prepared by mixing the above-produced resin with a solvent and other additive compounds. The component ratios of the prepared resist compositions are indicated in TABLES 3 and 4. The resist compositions were filtrated with 0.2-μm membrane filters, respectively, thereby obtaining resist solutions. The kinds of the solvent, the additive (basic compound) and the cross-linking agent used in each example are indicated below.

S-1: Propylene glycol monomethyl ether acetate (PGMEA)
S-2: γ-Butyrolactone
S-3: Ethyl lactate
S-4: Cyclohexanone
O-1: N,N-Dibutylaniline
O-2: 2,6-Diisopropylaniline
O-3: Diazabicyclo[4.3.0]nonene
O-4: 2,4,5-Triphenylimidazole
O-5: Ttrioctylamine
Cross-linking agent: NIKALAC MX-270 (glycoluril-based cross-linking agent, manufactured by Sanwa Chemical Co., Ltd.)

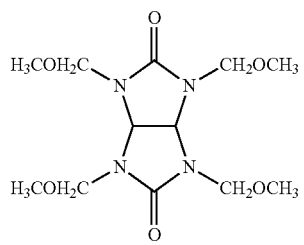

[Pattern Formation]

Each of the above-obtained resist solutions was spin-coated on a silicon wafer substrate to form a resist film of 250 nm thickness. The resist film was prebaked at 110° C., exposed to 248-nm ultraviolet radiation through a photomask, and then, subjected to post exposure baking treatment at 120° C. After that, the resist film was developed with 2.38 mass % aqueous tetramethylammoniumhydroxide solution for 1 minute at 23° C. It was possible to obtain a high-resolution pattern from each of the resist compositions. There were seen no failures such as poor substrate adhesion, poor film formation, development failure and poor etching resistance. The component ratio and evaluation results of the resist compositions are indicated in TABLES 3 and 4.

TABLE 3

| | Resin 1 | | Resin 2 | |
|---|---|---|---|---|
| Example | Kind | parts by mass | Kind | parts by mass |
| 1 | P-1 | 40 | none | — |
| 2 | P-3 | 40 | none | — |
| 3 | P-4 | 14 | P'-3 | 26 |
| 4 | P-5 | 40 | none | — |
| 5 | P-6 | 40 | none | — |
| 6 | P-2 | 40 | none | — |
| 7 | P-7 | 14 | P'-3 | 26 |
| 8 | P-8 | 40 | none | — |
| 9 | P-9 | 40 | none | — |
| 10 | P-10 | 40 | none | — |
| 11 | P-11 | 20 | P'-1 | 20 |
| 12 | P-12 | 20 | P'-2 | 20 |
| 13 | P-13 | 20 | P'-1 | 20 |
| 14 | P-14 | 20 | P'-2 | 20 |
| 15 | P-15 | 20 | P'-2 | 20 |
| 16 | P-16 | 40 | none | — |
| 17 | P-17 | 40 | none | — |
| 18 | P-18 | 40 | none | — |
| 19 | P-19 | 20 | P'-1 | 20 |
| 20 | P-20 | 40 | none | — |
| 21 | P-21 | 40 | none | — |
| 22 | P-22 | 40 | none | — |
| 23 | P-23 | 40 | none | — |
| 24 | P-24 | 40 | none | — |
| 25 | P-25 | 20 | P'-1 | 20 |

| | | | Solvent | |
|---|---|---|---|---|
| Example | Additive | Kind | parts by mass | Pattern shape |
| 1 | O-1 | S-1 | 400 | clean rectangular shape |
| 2 | O-2 | S-1 | 400 | clean rectangular shape |
| 3 | O-3 | S-1 | 400 | clean rectangular shape |
| 4 | O-3 | S-1 | 400 | clean rectangular shape |
| 5 | O-3 | S-1 | 400 | clean rectangular shape |
| 6 | O-1 | S-1 | 400 | clean rectangular shape |
| 7 | O-4 | S-4 | 400 | clean rectangular shape |
| 8 | O-5 | S-1 | 400 | clean rectangular shape |
| 9 | O-5 | S-1 | 400 | clean rectangular shape |
| 10 | O-5 | S-1 | 400 | clean rectangular shape |
| 11 | O-1 | S-1 | 400 | clean rectangular shape |
| 12 | O-1 | S-1 | 400 | clean rectangular shape |
| 13 | O-5 | S-1 | 400 | clean rectangular shape |
| 14 | O-3 | S-2 | 400 | clean rectangular shape |
| 15 | O-5 | S-1 | 400 | clean rectangular shape |
| 16 | O-5 | S-3 | 400 | clean rectangular shape |
| 17 | O-2 | S-1 | 400 | clean rectangular shape |
| 18 | O-3 | S-1 | 400 | clean rectangular shape |
| 19 | O-5 | S-1 | 400 | clean rectangular shape |
| 20 | O-5 | S-1 | 400 | clean rectangular shape |
| 21 | O-2 | S-1 | 400 | clean rectangular shape |
| 22 | O-5 | S-1 | 400 | clean rectangular shape |
| 23 | O-1 | S-1 | 400 | clean rectangular shape |
| 24 | O-2 | S-1 | 400 | clean rectangular shape |
| 25 | O-5 | S-2 | 400 | clean rectangular shape |

Additive (0.15 parts by mass)
O-1: N,N-Dibutylaniline
O-2: 2,6-Diisopropylaniline
O-3: Diazabicyclo[4.3.0]nonene
O-4: 2,4,5-Triphenylimidazole
O-5: Trioctylamine
Solvent
S-1: Propylene glycol monomethyl ether acetate (PGMEA)
S-2: γ-Butyrolactone
S-3: Ethyl lactate
S-4: Cyclohexanone

TABLE 4

| | Resin 1 | | Resin 2 | |
|---|---|---|---|---|
| Example | Kind | parts by mass | Kind | parts by mass |
| 26 | X-1 | 2 | P'-1 | 40 |
| 27 | X-1 | 4 | P'-2 | 40 |
| 28 | X-2 | 6 | P'-1 | 40 |
| 29 | X-2 | 1 | P'-2 | 40 |
| 30 | X-3 | 12 | P'-3 | 32 |
| 31 | X-4 | 30 | P'-4 | 19 |
| 32 | X-2 | 6 | P'-5 | 40 |
| 33 | N-1 | 40 | — | — |
| 34 | N-1 | 20 | N-4 | 20 |
| 35 | N-2 | 40 | — | — |
| 36 | N-3 | 40 | — | — |
| 37 | N-4 | 40 | — | — |
| 38 | PG-1 | 40 | — | — |
| 39 | PG-2 | 40 | — | — |
| 40 | X-5 | 5 | P'-2 | 40 |

TABLE 4-continued

| | | | | |
|---|---|---|---|---|
| 41 | X-6 | 5 | P'-3 | 40 |
| 42 | X-7 | 4 | P'-4 | 40 |
| 43 | X-8 | 7 | P'-5 | 40 |
| 44 | N-5 | 40 | — | — |
| 45 | N-6 | 40 | — | — |
| 46 | N-7 | 40 | — | — |
| 47 | N-8 | 40 | — | — |
| 48 | PG-3 | 40 | — | — |
| 49 | PG-4 | 40 | — | — |
| 50 | PG-5 | 40 | — | — |
| 51 | PG-6 | 40 | — | — |
| 52 | X-9 | 10 | P'-2 | 35 |
| 53 | X-10 | 12 | P'-3 | 32 |
| 54 | N-9 | 40 | — | — |
| 55 | N-10 | 40 | — | — |
| 56 | PG-7 | 40 | — | — |
| 57 | PG-8 | 40 | — | — |
| 58 | PG-9 | 40 | — | — |

| Example | Additive compounds | Solvent Kind | parts by mass | Pattern shape |
|---|---|---|---|---|
| 26 | O-5 | S-1 | 400 | clean rectangular shape |
| 27 | O-5 | S-1 | 400 | clean rectangular shape |
| 28 | O-5 | S-4 | 400 | clean rectangular shape |
| 29 | O-5 | S-1 | 400 | clean rectangular shape |
| 30 | O-1 | S-1 | 400 | clean rectangular shape |
| 31 | O-1 | S-1 | 400 | clean rectangular shape |
| 32 | O-5 | S-1 | 400 | clean rectangular shape |
| 33 | cross-linking agent, O-5 | S-1 | 400 | clean rectangular shape |
| 34 | cross-linking agent, O-5 | S-1 | 400 | clean rectangular shape |
| 35 | cross-linking agent, O-1 | S-1 | 400 | clean rectangular shape |
| 36 | cross-linking agent, O-4 | S-2 | 400 | clean rectangular shape |
| 37 | cross-linking agent, O-5 | S-3 | 400 | clean rectangular shape |
| 38 | O-1 | S-1 | 400 | clean rectangular shape |
| 39 | O-1 | S-1 | 400 | clean rectangular shape |
| 40 | O-5 | S-1 | 400 | clean rectangular shape |
| 41 | O-1 | S-1 | 400 | clean rectangular shape |
| 42 | O-1 | S-1 | 400 | clean rectangular shape |
| 43 | O-5 | S-1 | 400 | clean rectangular shape |
| 44 | cross-linking agent, O-1 | S-1 | 400 | clean rectangular shape |
| 45 | cross-linking agent, O-1 | S-4 | 400 | clean rectangular shape |
| 46 | cross-linking agent, O-5 | S-2 | 400 | clean rectangular shape |
| 47 | cross-linking agent, O-5 | S-1 | 400 | clean rectangular shape |
| 48 | O-1 | S-1 | 400 | clean rectangular shape |
| 49 | O-2 | S-1 | 400 | clean rectangular shape |
| 50 | O-4 | S-3 | 400 | clean rectangular shape |
| 51 | O-5 | S-4 | 400 | clean rectangular shape |
| 52 | O-5 | S-1 | 400 | clean rectangular shape |
| 53 | O-5 | S-1 | 400 | clean rectangular shape |
| 54 | cross-linking agent, O-5 | S-4 | 400 | clean rectangular shape |
| 55 | cross-linking agent, O-1 | S-1 | 400 | clean rectangular shape |
| 56 | O-1 | S-1 | 400 | clean rectangular shape |
| 57 | O-2 | S-4 | 400 | clean rectangular shape |
| 58 | O-5 | S-4 | 400 | clean rectangular shape |

Cross-linking agent (3 pats by mass) NIKALAC MX-270 (glycoluril-based cross-linking agent, manufactured by Sanwa Chemical Co., Ltd.)

Additive (15 parts by mass)

O-1: N,N-Dibutylaniline,

O-4: 2,4,5-Triphenylimidazole,

O-5: Trioctylamine Solvent

S-1: Propylene glycol monomethyl ether acetate (PGMEA),

S-2: γ-Butyrolactone,

S-3: Ethyl lactate,

S-4: Cyclohexanone

Reference Polymerization Examples 1 to 5

Using various monomers as shown in TABLE 5, sulfonate-free resins (P-1' to P-5') were produced in the same manner as in Polymerization Example 1 or 2. The mole ratio of the repeating units and the weight-average molecular weight (Mw) of the produced resins are indicated in TABLE 5.

TABLE 5

| Polymerization | Raw material composition | | | | | |
|---|---|---|---|---|---|---|
| Example | Monomer 1 | | Monomer 2 | | Monomer 3 | |
| Resin | Kind | mol % | Kind | mol % | Kind | mol % |
| P-1' | A-1 | 25 | B-1 | 45 | C-1 | 30 |
| P-2' | A-2 | 20 | B-1 | 45 | C-1 | 35 |
| P-3' | A-3 | 10 | B-1 | 45 | C-1 | 45 |
| P-4' | A-4 | 10 | B-1 | 45 | C-1 | 45 |
| P-5' | A-1 | 25 | B-1 | 45 | C-2 | 30 |

| Polymerization Example | Mole ratio of repeating units in resin | | | Molecular weight |
|---|---|---|---|---|
| Resin | Monomer 1 | Monomer 2 | Monomer 3 | Mw |
| P-1' | 24 | 44 | 32 | 9,200 |
| P-2' | 19 | 44 | 37 | 8,500 |
| P-3' | 9 | 45 | 46 | 8,100 |
| P-4' | 10 | 46 | 44 | 9,700 |
| P-5' | 23 | 44 | 33 | 8,900 |

Reference Polymerization Examples 6 to 9

Using conventional onium salt monomers (PAG-C1, PAG-C2), in place of the polymerizable fluorine-containing sulfonic acid onium salts (monomers) according to the present invention, as shown in TABLE 6, resins (P-C1 to P-C4) were produced in the same manner as in Polymerization Example 1 or 2. The mole ratio of the repeating units and the weight-average molecular weight (Mw) of the produced resins are indicated in TABLE 6.

TABLE 6

| Polymerization Example | Raw material composition | | | | | | | |
|---|---|---|---|---|---|---|---|---|
| | Monomer 1 | | Monomer 2 | | Monomer 3 | | Monomer 4 | |
| Resin | Kind | mol % | Kind | mol % | Kind | mol % | Kind | mol % |
| P-C1 | PAG-C1 | 15 | — | — | B-1 | 45 | C-1 | 40 |
| P-C2 | PAG-C2 | 15 | — | — | B-1 | 45 | C-1 | 40 |
| P-C3 | PAG-C3 | 20 | A-5 | 30 | — | — | C-1 | 50 |
| P-C4 | PAG-C4 | 20 | A-5 | 25 | B-1 | 25 | C-1 | 30 |

| Polymerization Example | Mole ratio of repeating units in resin | | | | Molecular weight |
|---|---|---|---|---|---|
| Resin | Monomer 1 | Monomer 2 | Monomer 3 | Monomer 3 | Mw |
| P-C1 | 13 | — | 46 | 41 | 7,500 |
| P-C2 | 14 | — | 45 | 41 | 7,900 |
| P-C3 | 18 | 28 | — | 54 | 9,300 |
| P-C4 | 17 | 27 | 26 | 30 | 7,100 |

Comparative Examples 1 to 12

Resist compositions were prepared, in the same manner as in Examples 1 to 58, by mixing the conventional onium salt monomer resins produced in Reference Polymerization Examples 6 to 9 with a solvent and other additive compounds. However, many of the resins were difficult to dissolve in propylene glycol monomethyl ether acetate (PGMEA) so that it was impossible to completely dissolve these resins even in twice as much volume of PGMEA. In the case of using cyclohexanone as the solvent, some of the resins were dissolved in the solvent. The thus-prepared resist compositions were subjected to pattern formation in the same manner as in Examples 1 to 58. The component ratio and evaluation results of the resist compositions are indicated in TABLE 7.

TABLE 7

| Comparative Example | Resin 1 | | Cross-linking agent, Additive | Solvent | | Pattern shape |
|---|---|---|---|---|---|---|
| | Kind | Parts by mass | | Kind | Parts by mass | |
| 1 | P-C1 | 40 | O-1 | S-1 | 400 | slightly distorted rectangular shape |
| 2 | P-C1 | 40 | O-1 | S-1 | 800 | slightly distorted rectangular shape |
| 3 | P-C1 | 40 | O-1 | S-4 | 400 | slightly distorted rectangular shape |
| 4 | P-C2 | 40 | O-1 | S-1 | 400 | slightly distorted rectangular shape |
| 5 | P-C2 | 40 | O-1 | S-1 | 800 | slightly distorted rectangular shape |
| 6 | P-C2 | 40 | O-1 | S-4 | 400 | slightly distorted rectangular shape |
| 7 | P-C3 | 40 | cross-linking agent, O-1 | S-1 | 400 | slightly distorted rectangular shape |
| 8 | P-C3 | 40 | cross-linking agent, O-1 | S-1 | 800 | slightly distorted rectangular shape |
| 9 | P-C3 | 40 | cross-linking agent, O-1 | S-4 | 400 | slightly distorted rectangular shape |
| 10 | P-C4 | 40 | cross-linking agent, O-1 | S-1 | 400 | slightly distorted rectangular shape |
| 11 | P-C4 | 40 | cross-linking agent, O-1 | S-1 | 800 | slightly distorted rectangular shape |
| 12 | P-C4 | 40 | cross-linking agent, O-1 | S-4 | 400 | slightly distorted rectangular shape |

Cross-linking agent (3 pats by mas): NIKALAC MX-270 (glycoluril-based cross-linking agent, manufactured by Sanwa Chemical Co., Ltd.)
Additive (0.15 parts by mass)
O-1: N,N-Dibutylaniline
Solvent
S-1: Propylene glycol monomethyl ether acetate (PGMEA)
S-4: Cyclohexanone

Examples 59 to 66

Using the resin P'-1 produced in Reference Polymerization Example 1 as a base resin and the polymerizable fluorine-containing sulfonic acid onium salt according to the present invention as a photoacid generator, resist compositions were prepared in the same manner as in Examples 1 to 53. The prepared resist compositions were subjected to pattern formation and observed in the same manner as in the other examples. It was possible to obtain a high-resolution pattern from each of the resist compositions. There were seen no failures such as poor substrate adhesion, poor film formation, development failure and poor etching resistance. The component ratio and evaluation results of the resist compositions are indicated in TABLE 8.

TABLE 8

| Example | Resin | | PAG | | Basic compound | Solvent | | Pattern shape |
|---|---|---|---|---|---|---|---|---|
| | Kind | parts by mass | Kind | parts by mass | | Kind | parts by mass | |
| 59 | P'-1 | 40 | PAG-1 | 4 | O-1 | S-1 | 400 | clean rectangular shape |
| 60 | P'-1 | 40 | PAG-2 | 4 | O-1 | S-1 | 400 | clean rectangular shape |

TABLE 8-continued

| Example | Resin Kind | Resin parts by mass | PAG Kind | PAG parts by mass | Basic compound Kind | Solvent Kind | Solvent parts by mass | Pattern shape |
|---|---|---|---|---|---|---|---|---|
| 61 | P'-1 | 40 | PAG-3 | 4 | O-1 | S-1 | 400 | clean rectangular shape |
| 62 | P'-1 | 40 | PAG-4 | 4 | O-1 | S-1 | 400 | clean rectangular shape |
| 63 | P'-1 | 40 | PAG-5 | 4 | O-1 | S-1 | 400 | clean rectangular shape |
| 64 | P'-1 | 40 | PAG-6 | 4 | O-1 | S-1 | 400 | clean rectangular shape |
| 65 | P'-1 | 40 | PAG-7 | 4 | O-1 | S-1 | 400 | clean rectangular shape |
| 66 | P'-1 | 40 | PAG-8 | 4 | O-1 | S-1 | 400 | clean rectangular shape |

Basic compound (0.15 parts by mass)
O-1: N,N-Dibutylaniline
Solvent
S-1: Propylene glycol monomethyl ether acetate (PGMEA)

Examples 67 and 68

Resist compositions were prepared using the resin P-1 or P-22 indicated in TABLE 1 as a base resin in combination with a conventional photoacid generator (PAG): notafluorobutane sulfonic acid triphenylsulfonate salt (PAG-C3). The prepared resist compositions were subjected to pattern formation and observed in the same manner as in the other examples. It was possible to obtain a high-resolution pattern from each of the resist compositions. There were seen no failures such as poor substrate adhesion, poor film formation, development failure and poor etching resistance. The component ratio and evaluation results of the resist compositions are indicated in TABLE 9.

TABLE 9

| Example | Resin Kind | Resin parts by mass | PAG Kind | PAG parts by mass | Basic compound Kind | Solvent Kind | Solvent parts by mass | Pattern shape |
|---|---|---|---|---|---|---|---|---|
| 67 | P-1 | 40 | PAG-C3 | 4 | O-1 | S-1 | 400 | clean rectangular shape |
| 68 | P-22 | 40 | PAG-C3 | 4 | O-1 | S-1 | 400 | clean rectangular shape |

Basic compound (0.15 parts by mass)
O-1: N,N-Dibutylaniline
Solvent
S-1: Propylene glycol monomethyl ether acetate (PGMEA)

INDUSTRIAL APPLICABILITY

The resin of the present invention can be used as a photoacid generator for a photoresist material or can be used in itself as a positive or negative resist resin. The monomer of such a resin is also useful as a raw material for production of other compounds.

The invention claimed is:
1. A fluorine-containing sulfonate resin comprising a repeating unit of the following general formula (4):

$$\text{(4)}$$

where X each independently represent a hydrogen atom or a fluorine atom;
n represents an integer of 1 to 7;
R represents a hydrogen atom, a halogen atom or a $C_1$-$C_3$ alkyl or fluorine-containing alkyl group;
J represents a divalent linking group selected from the group consisting of a substituted or unsubstituted methylene group, a substituted or unsubstituted divalent alicyclic hydrocarbon group, a substituted or unsubstituted divalent aromatic hydrocarbon group, a substituted or unsubstituted heterocyclic group, and a divalent linking group formed by a combination of
  a group selected from the group consisting of a substituted or unsubstituted methylene group, a substituted or unsubstituted divalent alicyclic hydrocarbon group, a substituted or unsubstituted divalent aromatic hydrocarbon group or a substituted or unsubstituted heterocyclic group
  and one or more kinds of linking groups selected from an ether bond, a thioether bond, a carbonyl group, an ester group, an oxycarbonyl group, an amide group, a sulfoneamide group, an urethane group and an urea group;
any number of hydrogen atoms bonded to carbon atoms of J may be substituted with a fluorine atom;
any carbon atoms of J may form a ring with or without a substituent; and
$Q^+$ represents either:
  a sulfonium cation selected from the group consisting of triphenylsulfonium, (4-tert-butylphenyl)diphenylsulfonium, (4-tert-butoxyphenyl)diphenylsulfonium, tris(4-tert-butylphenyl)sulfonium, (4-tert-butoxycarbonylmethyloxyphenyl)diphenylsulfonium, 5-phenyldibenzothiophenium, 5-(4-methylphenyl)dibenzothiophenium, 5-(4-methoxyphenyl)dibenzothiophenium, 5-(4-fluorophenyl)dibenzothiophenium, tolyldiphenylsulfonium and (4-tert-butylphenyl)tetramethylene sulfide; or
  a iodonium cation selected from the group consisting of diphenyliodonium, bis(4-methylphenyl)iodonium, bis(4-ethylphenyl)iodonium, bis(4-tert-butylphenyl)iodonium, bis(4-(1,1-dimethylpropyl)phenyl)iodonium, (4-methoxyphenyl)phenyliodonium, (4-tert-butoxyphenyl)phenyliodonium, (4-acryloyloxy)phenylphenyliodonium and (4-methacryloyloxy)phenylphenyliodonium.

2. The fluorine-containing sulfonate resin according to claim 1, further comprising one kind or more kinds selected from the group consisting of repeating units formed respectively by cleavage of polymerizable double bonds of olefins, fluorine-containing olefins, acrylic acid esters, methacrylic acid esters, fluorine-containing acrylic acid esters, fluorine-containing methacrylic acid esters, norbornene compounds, fluorine-containing norbornene compounds, styrenic compounds, fluorine-containing styrenic compounds, vinyl ethers and fluorine-containing vinyl ethers.

3. The fluorine-containing sulfonate resin according to claim 1, further comprising any of repeating units of the following general formulas (6), (9), (10), (11), (12) and (16):

(6)

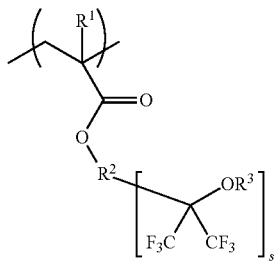

where $R^1$ represents a hydrogen atom, a halogen atom or a $C_1$-$C_3$ alkyl or fluorine-containing alkyl group; $R^2$ represents a substituted or unsubstituted aliphatic hydrocarbon group, a substituted or unsubstituted aromatic group or a divalent organic group formed by combination of a plurality thereof; any number of hydrogen atoms of $R^2$ may be substituted with a fluorine atom; $R^2$ may contain an ether bond or a carbonyl group; $R^3$ represents a hydrogen atom, a substituted or unsubstituted $C_1$-$C_{25}$ aliphatic hydrocarbon group or a substituted or unsubstituted $C_1$-$C_{25}$ aromatic hydrocarbon group; any number of hydrogen atoms of $R^3$ may be substituted with a fluorine atom; $R^3$ may contain an ether bond or a carbonyl group; and s represents an integer of 2 to 8;

(9)

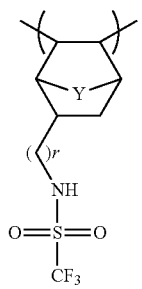

where Y represents either —$CH_2$—, —O— or —S—; and r represents an integer of 2 to 6;

(10)

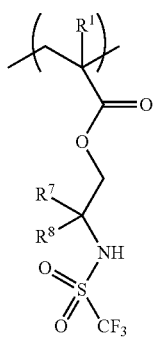

where $R^1$ has the same definition as in the general formula (6); and $R^7$ and $R^8$ each independently represent a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an ether bond or a carbonyl group;

(11)

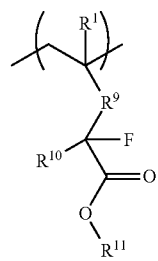

where $R^1$ has the same definition as in the general formula (6); $R^9$ represents a divalent linking group; $R^{10}$ represents a hydrogen atom, a fluorine atom or a fluorine-containing alkyl group; and $R^{11}$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an ether bond or a carbonyl group;

(12)

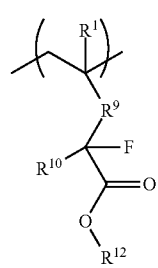

where $R^1$ has the same definition as in the general formula (6); $R^9$ and $R^{10}$ have the same definitions as in the general formula (11); and $R^{12}$ represents an acid labile group; and (16)

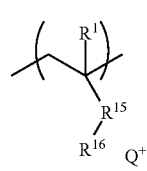

where $R^1$ has the same definition as in the general formula (6); $R^{15}$ represents a divalent linking group; $R^{16}$ represents either —$SO_3^-$, —$CO_2^-$ or —$N^-HSO_3$; and $Q^+$ represents either a sulfonium cation or an iodonium cation.

4. The fluorine-containing sulfonate resin according to claim 3, wherein the repeating unit of the general formula (6) is a repeating unit of the following general formula (7) or (8):

(7)

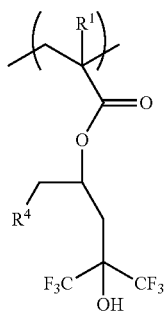

where $R^1$ has the same definition as in the general formula (6); and $R^4$ represents a hydrogen atom or a $C_1$-$C_4$ alkyl or fluorine-containing alkyl group; and (8)

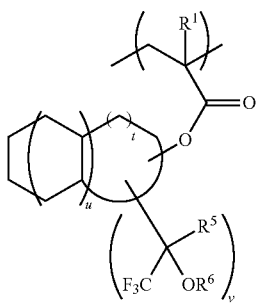

where $R^1$ has the same definition as in the general formula (6); $R^5$ represents a methyl group or a trifluoromethyl group; $R^6$ represents a hydrogen atom, a substituted or unsubstituted $C_1$-$C_{25}$ aliphatic hydrocarbon group or a substituted or unsubstituted $C_1$-$C_{25}$ aromatic hydrocarbon group, a part of which may contain a fluorine atom, an ether bond or a carbonyl group; u represents an integer of 0 to 2; t and v represent an integer of 1 to 8 and satisfy a relationship of v≤t+2; and, in the case where v is an integer of 2 to 8, $R^5$ and $R^6$ may be the same or different.

5. A resist composition comprising at least the fluorine-containing sulfonate resin according to claim 1 and a solvent.

6. The resist composition according to claim 5, wherein the fluorine-containing sulfonate resin has an acid labile group so that the resist composition serves as a chemically amplified positive resist composition.

7. The resist composition according to claim 5, further comprising an acid labile group-containing resin.

8. A pattern formation method, comprising: applying the resist composition according to claim 5 to a substrate; heat treating the applied resist composition and exposing the heat treated resist composition to high energy radiation of 300 nm or less wavelength through a photomask; and, after optionally heat treating the exposed resist composition, developing the exposed resist composition with a developer.

9. The pattern formation method according to claim 8, wherein said developing is performed by liquid immersion lithography in which water or any liquid medium other than water, having a higher refractive index than air, is inserted between the substrate to which the resist composition has been applied and a projection lens.

10. A polymerizable fluorine-containing sulfonate comprising a structure of the following general formula (2):

(2)

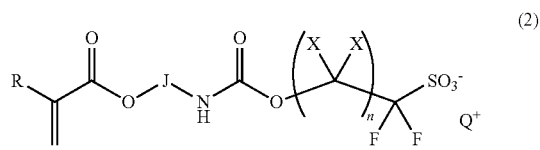

where X each independently represents a hydrogen atom or a fluorine atom;

n represents an integer of 1 to 7;

R represents a hydrogen atom, a halogen atom or a $C_1$-$C_3$ alkyl or fluorine-containing alkyl group;

J represents a divalent linking group selected from the group consisting of a substituted or unsubstituted methylene group, a substituted or unsubstituted divalent alicyclic hydrocarbon group, a substituted or unsubstituted divalent aromatic hydrocarbon group, a substituted or unsubstituted heterocyclic group, and a divalent linking group formed by a combination of a group selected from the group consisting of a substituted or unsubstituted methylene group, a substituted or unsubstituted divalent alicyclic hydrocarbon group, a substituted or unsubstituted divalent aromatic hydrocarbon group and a substituted or unsubstituted heterocyclic group and one or more kinds of linking groups selected from an ether bond, a thioether bond, a carbonyl group, an ester group, an oxycarbonyl group, an amide group, a sulfoneamide group, an urethane group and an urea group;

any number of hydrogen atoms bonded to carbon atoms of J may be substituted with a fluorine atom;

any carbon atoms of J may form a ring with or without a substituent; and $Q^+$ represents either: a sulfonium cation selected from the group consisting of triphenylsulfonium, (4-tert-butylphenyl)diphenylsulfonium, (4-tert-butoxyphenyl)diphenylsulfonium, tris(4-tert-butylphenyl)sulfonium, (4-tert-butoxycarbonylmethyloxyphenyl)diphenylsulfonium, 5-phenyldibenzothiophenium, 5-(4-methylphenyl)dibenzothiophenium, 5-(4-methoxyphenyl)dibenzothiophenium, 5-(4-fluorophenyl)dibenzothiophenium, tolyldiphenylsulfonium and (4-tert-butylphenyl)tetramethylene sulfide; or a iodonium cation selected from the group consisting of diphenyliodonium, bis(4-methylphenyl)iodonium, bis(4-ethylphenyl)iodonium, bis(4-tert-butylphenyl)iodonium, bis(4-(1,1-dimethylpropyl)phenyl)iodonium, (4-methoxyphenyl)phenyliodonium, (4-tert-butoxyphenyl)phenyliodonium, (4-acryloyloxy)phenylphenyliodonium or (4-methacryloyloxy)phenylphenyliodonium.

* * * * *